(12) United States Patent
Komori et al.

(10) Patent No.: US 11,814,393 B2
(45) Date of Patent: Nov. 14, 2023

(54) SUBSTITUTED GUANIDINE COMPOUNDS

(71) Applicant: UBE CORPORATION, Ube (JP)

(72) Inventors: Ken-Ichi Komori, Ube (JP); Akishi Ninomiya, Ube (JP); Masaru Shinohara, Ube (JP); Koji Ito, Ube (JP); Tetsuo Kawaguchi, Ube (JP); Hiroyoshi Kawada, Ube (JP); Tomio Kimura, Tokyo (JP)

(73) Assignee: UBE CORPORATION, Ube (JP)

( * ) Notice: Subject to any disclaimer, the term of this patent is extended or adjusted under 35 U.S.C. 154(b) by 0 days.

(21) Appl. No.: 17/841,815

(22) Filed: Jun. 16, 2022

(65) Prior Publication Data

US 2022/0315599 A1    Oct. 6, 2022

Related U.S. Application Data

(63) Continuation of application No. 16/474,339, filed as application No. PCT/JP2017/046898 on Dec. 27, 2017, now Pat. No. 11,396,514.

(30) Foreign Application Priority Data

Dec. 28, 2016 (JP) ................... 2016-255567

(51) Int. Cl.
*C07D 401/04* (2006.01)
*C07D 491/107* (2006.01)
*C07D 405/12* (2006.01)

(52) U.S. Cl.
CPC ....... *C07D 491/107* (2013.01); *C07D 401/04* (2013.01); *C07D 405/12* (2013.01)

(58) Field of Classification Search
CPC .......................... C07D 401/04; C07D 491/107
USPC ........................ 514/343; 546/276.4
See application file for complete search history.

(56) References Cited

U.S. PATENT DOCUMENTS

| 8,716,470 B2 * | 5/2014 | Yoshihara ............... A61P 11/16 544/122 |
| 8,802,679 B2 | 8/2014 | Yoshihara et al. |
| 8,999,989 B2 | 4/2015 | Matsukawa et al. |
| 2007/0254931 A1 | 11/2007 | Inoue et al. |
| 2012/0184520 A1 | 7/2012 | Yoshihara et al. |
| 2013/0143860 A1 | 6/2013 | Yoshihara et al. |
| 2019/0152953 A1 | 5/2019 | Komori et al. |

FOREIGN PATENT DOCUMENTS

| RU | 2526256 C2 | 8/2014 |
| WO | 2010149684 A1 | 12/2010 |
| WO | 2011034078 | 3/2011 |
| WO | 2012124696 | 9/2012 |
| WO | 2017022861 | 5/2018 |

OTHER PUBLICATIONS

International Search Report (PCT/ISA/210) issued in PCT/JP2017/046898, dated Apr. 3, 2018.
Weston et al., "Vascular adhesion protein-1 promotes liver inflammation and drives hepatic fibrosis," The Journal of Clinical Investigation, Feb. 2015, vol. 125, No. 2, pp. 501-520.
Yu et al., "Aminoguanidine inhibits semicarbazide-sensitive amine oxidase activity: implications for advanced glycation and diabetic complications," Diabetologia, 1997, vol. 40, pp. 1243-1250.
Yu et al., "Involvement of semicarbazide-sensitive amine oxidase-mediated deamination in atherogenesis in KKAy diabetic mice fed with high cholesterol diet," Diabetologia, 2002, vol. 45, pp. 1255-1262.
Wuts PGM, Greene TW. Greene's Protectie Groups in Organic Synthesis. 4th ed. Hoboken (NJ): John Wiley & Sons, Inc; c2007. 1082p.

* cited by examiner

*Primary Examiner* — Niloofar Rahmani
(74) *Attorney, Agent, or Firm* — Jianjie Hu

(57) ABSTRACT

The present invention provides a compound of general formula (I) (wherein X is as described in the present description and claims), or a pharmacologically acceptable salt thereof, and a pharmaceutical composition containing that compound.

6 Claims, No Drawings

SUBSTITUTED GUANIDINE COMPOUNDS

CROSS-REFERENCE TO RELATED APPLICATIONS

This application is a continuation of U.S. application Ser. No. 16/474,339, filed Jun. 27, 2019, which is a 35 U.S.C. § 371 National Stage application of International Application PCT/JP2017/046898 (WO 2018/124179), filed Dec. 27, 2017, which claims priority to Japanese Patent Application 2016-255567, filed Dec. 28, 2016; the contents of which are incorporated herein by reference.

TECHNICAL FIELD

The present invention relates to substituted guanidine compounds, a pharmaceutical composition containing the same, and particularly substituted guanidine compounds and a pharmaceutical composition containing the same for treating diseases prevented, alleviated and/or treated by inhibiting VAP-1.

PRIOR ART

Type 2 diabetes is a type of lifestyle disease for which the number of patients with this disease has continued to increase in recent years. A prolonged hyperglycemic state gradually destroys microvessels throughout the body, resulting in the risk of causing serious damage to various organs including the oculus and kidney. These types of serious damage are referred to as diabetic complications, and among these, preventing the onset and inhibiting the progression of the three major diabetic complications consisting of diabetic neuropathy, diabetic retinopathy and diabetic nephropathy are becoming important issues.

Although the prevention of onset and inhibition of progression of diabetic complications are foremost based on the control of blood glucose level, increases in the activity of VAP-1 (vascular adhesion protein-1, also referred to as semicarbazide-sensitive amine oxidase (SSAO)) in blood and the correlation thereof with plasma glycosylated hemoglobin levels have been observed in diabetes patients in recent years. This enzyme, which is selectively located in vascular tissue, catalyzes deamination of methylamine and aminoacetone, respectively producing formaldehyde and methylglyoxal in addition to $H_2O_2$ and ammonia. Since each of these substances has cytotoxicity, increases in VAP-1 activity in blood are attracting attention as one of the causes of the onset of inflammatory diseases or diabetic complications (see, for example, Non-Patent Documents 1 and 2).

Various VAP-1 enzyme inhibitors have been reported thus far. A compound of the following formula:

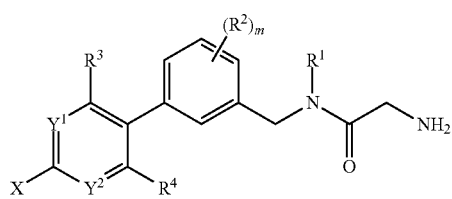

is described to have VAP-1 inhibitory activity and be useful for the prevention and/or treatment of VAP-1-associated diseases including various types of inflammatory diseases and diabetic complications, and particularly diabetic nephropathy or diabetic macular edema (see, for example, Patent Document 1).

Moreover, a compound of the following formula:

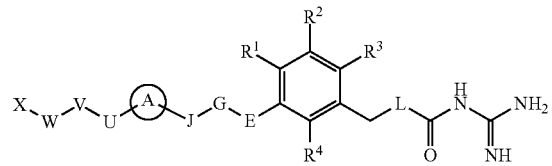

is described to have VAP-1 inhibitory activity and be useful for the prevention and/or treatment of VAP-1-associated diseases including various types of inflammatory diseases and diabetic complications, and particularly diabetic nephropathy or diabetic macular edema (see, for example, Patent Document 2).

On the other hand, it has also been reported that expression of VAP-1 increases in the liver of patients with chronic liver disease, that soluble VAP-1 concentration in serum and expression of VAP-1 in the liver of patients with non-alcoholic fatty liver disease increase in comparison with those of patients not having non-alcoholic fatty liver disease, and that there is a correlation between soluble VAP-1 concentration in serum and the severity of fibrosis based on liver biopsies performed on patients with non-alcoholic fatty liver disease (see, for example, Non-Patent Document 3). On the basis thereof, in addition to the aforementioned diabetic complications, non-alcoholic fatty liver disease, and particularly non-alcoholic steatohepatitis, is expected to be prevented, alleviated and/or treated by inhibiting VAP-1.

PRIOR ART DOCUMENTS

Patent Documents

Patent Document 1: International Publication No. WO 2011/034078
Patent Document 2: International Publication No. WO 2012/124696

Non-Patent Documents

Non-Patent Document 1: Diabetologia (1997), 40: 1243-1250
Non-Patent Document 2: Diabetologia (2002), 45: 1255-1262
Non-Patent Document 3: The Journal of Clinical Investigation (2015), 2: 501-520

SUMMARY OF INVENTION

Problem to be Solved by the Invention

The present invention provides a useful novel compound for treating diseases prevented, alleviated and/or treated by inhibiting VAP-1, and a pharmaceutical composition containing the same.

Means for Solving the Problem

As a result of conducting extensive research on compounds having VAP-1 inhibitory activity, the present inventors found that a series of substituted guanidine compounds, or salts thereof, having a fluoropyridine ring at a specific position in the molecule has superior VAP-1 inhibitory activity and is useful for the treatment of diseases prevented, alleviated and/or treated by inhibiting VAP-1, and particularly diabetic nephropathy and non-alcoholic steatohepatitis, thereby leading to completion of the present invention.

The present invention provides the following [1] to [20].
[1] A compound of general formula (I):

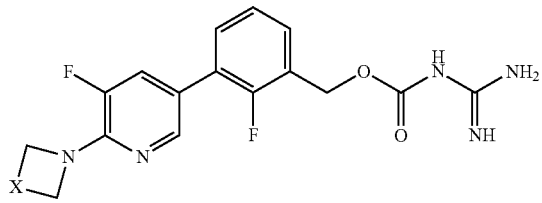

wherein,
X is a $CR^1R^2$, a carbonyl group or a group of formula (Ia):

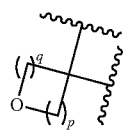

$R^1$ and $R^2$, independently of each other, are a hydrogen atom, halogen atom, hydroxy group, protected hydroxy group, optionally substituted $C_1$-$C_6$ alkyl group or optionally substituted $C_1$-$C_6$ alkoxy group, where the term "substituted" refers to being substituted with at least one substituent selected from the group consisting of a deuterium atom, halogen atom, hydroxy group and $C_1$-$C_6$ alkoxy group,
p and q, independently of each other, are integers from 0 to 3, provided that the sum of p and q is 2 or more,
or a pharmacologically acceptable salt thereof.
[2] The compound described in [1] or a pharmacologically acceptable salt thereof, wherein $R^1$ is a hydrogen atom, halogen atom, hydroxy group, optionally substituted $C_1$-$C_6$ alkyl group or optionally substituted $C_1$-$C_6$ alkoxy group, and $R^2$ is a hydrogen atom, halogen atom or $C_1$-$C_3$ alkyl group.
[3] The compound described in [2] or a pharmacologically acceptable salt thereof, wherein $R^1$ is a halogen atom, hydroxy group, $C_1$-$C_6$ alkoxy group or $C_1$-$C_6$ alkoxy group substituted with at least one deuterium atom.
[4] The compound described in [1] or a pharmacologically acceptable salt thereof, wherein p and q, independently of each other, are integers from 1 to 2.
[5] The compound described in [1] or a pharmacologically acceptable salt thereof, wherein the compound is:
2-fluoro-3-[5-fluoro-6-(3-methoxyazetidin-1-yl)pyridin-3-yl]benzyl carbamimidoylcarbamate,
2-fluoro-3-{5-fluoro-6-[3-(methoxy-d₃)azetidin-1-yl]pyridin-3-yl}benzyl carbamimidoylcarbamate,
3-[6-(3-ethoxyazetidin-1-yl)-5-fluoropyridin-3-yl]-2-fluorobenzyl carbamimidoylcarbamate,
2-fluoro-3-{5-fluoro-6-[3-(2-fluoroethoxy)azetidin-1-yl]pyridin-3-yl}benzyl carbamimidoylcarbamate,
2-fluoro-3-[5-fluoro-6-(3-propoxyazetidin-1-yl)pyridin-3-yl]benzyl carbamimidoylcarbamate,
2-fluoro-3-[5-fluoro-6-(3-isopropoxyazetidin-1-yl)pyridin-3-yl]benzyl carbamimidoylcarbamate,
2-fluoro-3-(5-fluoro-6-{3-[(tetrahydropyran-2-yl)oxy]azetidin-1-yl}pyridin-3-yl)benzyl carbamimidoylcarbamate,
2-fluoro-3-[5-fluoro-6-(3-hydroxyazetidin-1-yl)pyridin-3-yl]benzyl carbamimidoylcarbamate,
3-[6-(azetidin-1-yl)-5-fluoropyridin-3-yl]-2-fluorobenzyl carbamimidoylcarbamate,
2-fluoro-3-[5-fluoro-6-(3-fluoroazetidin-1-yl)pyridin-3-yl]benzyl carbamimidoylcarbamate,
3-[6-(3,3-difluoroazetidin-1-yl)-5-fluoropyridin-3-yl]-2-fluoro-benzyl carbamimidoylcarbamate,
2-fluoro-3-[5-fluoro-6-(3-methylazetidin-1-yl)pyridin-3-yl]benzyl carbamimidoylcarbamate,
3-[6-(3,3-dimethylazetidin-1-yl)-5-fluoropyridin-3-yl]-2-fluorobenzyl carbamimidoylcarbamate,
2-fluoro-3-(5-fluoro-6-{3-methyl-3-[(tetrahydropyran-2-yl)oxy]azetidin-1-yl}pyridin-3-yl)benzyl carbamimidoylcarbamate,
2-fluoro-3-[5-fluoro-6-(3-hydroxy-3-methylazetidin-1-yl)pyridin-3-yl]benzyl carbamimidoylcarbamate or
2-fluoro-3-[5-fluoro-6-(2-oxa-6-azaspiro[3.3]heptan-6-yl)pyridin-3-yl]benzyl carbamimidoylcarbamate.
[6] The compound described in [1] or a pharmacologically acceptable salt thereof, wherein the compound is:
2-fluoro-3-[5-fluoro-6-(3-methoxyazetidin-1-yl)pyridin-3-yl]benzyl carbamimidoylcarbamate.
[7] The compound described in [1] or a pharmacologically acceptable salt thereof, wherein the compound is:
2-fluoro-3-{5-fluoro-6-[3-(methoxy-d₃)azetidin-1-yl]pyridin-3-yl}benzyl carbamimidoylcarbamate.
[8] The compound described in [1] or a pharmacologically acceptable salt thereof, wherein the compound is:
2-fluoro-3-[5-fluoro-6-(3-hydroxyazetidin-1-yl)pyridin-3-yl]benzyl carbamimidoylcarbamate.
[9] The compound described in [1] or a pharmacologically acceptable salt thereof, wherein the compound is:
2-fluoro-3-[5-fluoro-6-(3-fluoroazetidin-1-yl)pyridin-3-yl]benzyl carbamimidoylcarbamate.
[10] The compound described in [1] or a pharmacologically acceptable salt thereof, wherein the compound is:
2-fluoro-3-[5-fluoro-6-(3-hydroxy-3-methylazetidin-1-yl)pyridin-3-yl]benzyl carbamimidoylcarbamate.
[11] The compound described in [1] or a pharmacologically acceptable salt thereof, wherein the compound is:
2-fluoro-3-[5-fluoro-6-(2-oxa-6-azaspiro[3.3]heptan-6-yl)pyridin-3-yl]benzyl carbamimidoylcarbamate.
[12] The compound described in any of [1] to [11] or a pharmacologically acceptable salt thereof, wherein the pharmacologically acceptable salt is a salt of an organic acid.
[13] The compound described in any of [1] to [11] or a pharmacologically acceptable salt thereof, wherein the pharmacologically acceptable salt is a salt of a dicarboxylic acid.
[14] A pharmaceutical composition comprising the compound described in any of [1] to [13], or a pharmacologically acceptable salt thereof, and at least one type of pharmacologically acceptable additive.
[15] The pharmaceutical composition described in [14] for treating a disease prevented, alleviated and/or treated by inhibiting VAP-1.
[16] The pharmaceutical composition described in [15], wherein the disease is diabetic nephropathy.
[17] The pharmaceutical composition described in [15], wherein the disease is non-alcoholic steatohepatitis.

[18] The compound described in any of [1] to [13] or a pharmacologically acceptable salt thereof, for use in treating a disease prevented, alleviated and/or treated by inhibiting VAP-1.

[19] Use of the compound described in any of [1] to [13] or a pharmacologically acceptable salt thereof, for producing a medicament for treating a disease prevented, alleviated and/or treated by inhibiting VAP-1.

[20] A method for treating a disease prevented, alleviated and/or treated by inhibiting VAP-1, comprising: administering a therapeutically effective amount of the compound described in any of [1] to [13] or a pharmacologically acceptable salt thereof, to a patient in need thereof.

Effects of the Invention

Since the compound of general formula (I) of the present invention, or a pharmacologically acceptable salt thereof, has high VAP-1 inhibitory activity and superior pharmacokinetic properties, it is useful in treating a disease prevented, alleviated and/or treated by inhibiting VAP-1, and typically non-alcoholic fatty liver diseases such as non-alcoholic steatohepatitis, inflammatory diseases such as atopic dermatitis or psoriasis, diabetic complications such as diabetic neuropathy, diabetic retinopathy (and particularly, diabetic macular edema) or diabetic nephropathy, vascular diseases such as atherosclerosis, heart diseases such as myocardial infarction, and metabolic diseases such as obesity.

DESCRIPTION OF THE PREFERRED EMBODIMENTS

The meanings of terms used in the present description and claims are as explained below. Terms used in the present description and claims have the meanings indicated below unless specifically indicated otherwise.

In the present description, numerical ranges indicated using the symbol "-" indicate a range that includes values indicated before and after the "-" symbol as the minimum and maximum values, respectively, of that range.

In the present invention, the compound of general formula (I) includes isotopic isomers thereof. Namely, all or a portion of the atoms of the compound of general formula (I) may be substituted with isotopic atoms corresponding respectively thereto. An isotopic atom refers to an atom having a different mass number from the mass number found in nature. Examples of such isotopic atoms include hydrogen atoms ($^{2}H$, $^{3}H$), carbon atoms ($^{13}C$, $^{14}C$), nitrogen atoms ($^{15}N$), and oxygen atoms ($^{17}O$, $^{18}O$). Deuterium atoms ($^{2}H$) in particular may be represented with a "D". In such cases, in the compound of general formula (I), all of the hydrogen atoms at specific locations indicated by D are substituted by deuterium atoms, and the molecular weight differs from the molecular weight calculated from the mass numbers found in nature.

"Halogen atom" or "halo" refers to a fluorine atom, chlorine atom, bromine atom or iodine atom either alone or in combination with other groups.

A "$C_1$-$C_6$ alkyl group" refers to a monovalent group of linear or branched, saturated aliphatic hydrocarbon having 1 to 6 carbon atoms either alone or in combination with other groups. Examples of $C_1$-$C_6$ alkyl groups include a methyl group, ethyl group, propyl group, butyl group, pentyl group and hexyl group (including various isomers thereof). A preferable aspect of a $C_1$-$C_6$ alkyl group is a $C_1$-$C_4$ alkyl group, and examples thereof include a methyl group, ethyl group, propyl group, isopropyl group, butyl group, isobutyl group, sec-butyl group and tert-butyl group. A more preferable aspect is a $C_1$-$C_3$ alkyl group.

A "$C_1$-$C_6$ alkoxy group" refers to a group of —O—R' (wherein, R' represents the aforementioned $C_1$-$C_6$ alkyl group) either alone or in combination with other groups. Examples of $C_1$-$C_6$ alkoxy groups include a methoxy group, ethoxy group, propoxy group, butyloxy group, pentyloxy group and hexyloxy group (including various isomers thereof). A preferable aspect of a $C_1$-$C_6$ alkoxy group is a $C_1$-$C_4$ alkoxy group, and examples thereof include a methoxy group, ethoxy group, propoxy group, isopropoxy group, butyloxy group, isobutyloxy group, sec-butyloxy group and tert-butyloxy group. A more preferable aspect is a $C_1$-$C_3$ alkoxy group.

An "aryl group" refers to a monovalent group of aromatic hydrocarbon having 6 to 10 carbon atoms. Examples of aryl groups include a phenyl group, 1-naphthyl group and 2-naphthyl group.

A "$C_1$-$C_7$ acyl group" refers to a group of —CO—R" (wherein, R" represents a hydrogen atom, the aforementioned $C_1$-$C_6$ alkyl group or a phenyl group). Examples of a $C_1$-$C_7$ acyl group include a formyl group, acetyl group, propionyl group, butyryl group, isobutyryl group, valeryl group, isovaleryl group, pivaloyl group, hexanoyl group and benzoyl group.

A "protected hydroxy group" refers to a hydroxy group protected with an appropriate protecting group. The protecting group can be arbitrarily selected by a person with ordinary skill in the art from among hydroxyl group protecting groups described in the known art such as Protective Groups in Organic Synthesis, 4th Edition, T. W. Greene and P. G. M. Wuts, ed., John Wiley & Sons Inc. (2006). Examples of protecting groups of a hydroxyl group include acyl-based protecting groups such as $C_1$-$C_7$ acyl groups (such as a formyl group, acetyl group, propionyl group, butyryl group, isobutyryl group, valeryl group, isovaleryl group, pivaloyl group, hexanoyl group or benzoyl group), acetal-based protecting groups such as a methoxymethyl group, 1-ethoxyethyl group, methylthiomethyl group, benzyloxymethyl group or tetrahydropyranyl group, silyl-based protecting groups such as a tri($C_1$-$C_4$ alkyl)silyl group (such as a trimethylsilyl group, triethylsilyl group, triisopropylsilyl group, dimethylisopropylsilyl group or tert-butyldimethylsilyl group), a ($C_1$-$C_4$ alkyl)diarylsilyl group (such as a tert-butyldiphenylsilyl group or diphenylmethylsilyl group), a triarylsilyl group (such as a triphenylsilyl group), or a tribenzylsilyl group, and benzyl-based protecting groups such as a benzyl group, p-methoxybenzyl group or triphenylmethyl group. Examples of preferable aspects of protecting groups include a $C_1$-$C_7$ acyl group, tetrahydropyranyl group, tri($C_1$-$C_4$ alkyl)silyl group, benzyl group, p-methoxybenzyl group and triphenylmethyl group. That is, a preferable aspect of a "protected hydroxy group" is, for example, a $C_1$-$C_7$ acyloxy group, a tetrahydropyranyloxy group, a tri($C_1$-$C_4$ alkyl)silyloxy group, a benzyloxy group, p-methoxybenzyloxy group or a triphenylmethyloxy group.

In the present invention, the phrase "optionally substituted" refers to a certain group being not substituted or being substituted with at least one substituent selected from a group of given substituents such as the group consisting of a deuterium atom, halogen atom, hydroxy group and $C_1$-$C_6$ alkoxy group.

In the present invention, a preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom, halogen atom, hydroxy group and $C_1$-$C_6$ alkoxy group. A more preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom, halogen atom and hydroxy group. An even more preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom and halogen atom. A particularly preferable aspect of an "optionally substituted $C_1$-$C_6$ alkyl group" is an (unsubstituted) $C_1$-$C_6$ alkyl group or $C_1$-$C_6$ alkyl group substituted with at least one substituent selected from the group consisting of a deuterium atom and fluorine atom.

In the present invention, a preferable aspect of an "optionally substituted $C_1$-$C_6$ alkoxy group" is an (unsubstituted) $C_1$-$C_6$ alkoxy group or $C_1$-$C_6$ alkoxy group substituted with at least one substituent selected from the group consisting of a deuterium atom, halogen atom, hydroxy group and $C_1$-$C_6$ alkoxy group. A more preferable aspect of an "optionally substituted $C_1$-$C_6$ alkoxy group" is an (unsubstituted) $C_1$-$C_6$ alkoxy group or $C_1$-$C_6$ alkoxy group substituted with at least one substituent selected from the group consisting of a deuterium atom, halogen atom and hydroxy group. An even more preferable aspect of an "optionally substituted $C_1$-$C_6$ alkoxy group" is an (unsubstituted) $C_1$-$C_6$ alkoxy group or $C_1$-$C_6$ alkoxy group substituted with at least one substituent selected from the group consisting of a deuterium atom and halogen atom. A particularly preferable aspect of an "optionally substituted $C_1$-$C_6$ alkoxy group" is an (unsubstituted) $C_1$-$C_6$ alkoxy group or $C_1$-$C_6$ alkoxy group substituted with at least one substituent selected from the group consisting of a deuterium atom and fluorine atom.

The compound of general formula (I) of the present invention includes stereoisomers thereof (if such stereoisomers exist). Stereoisomers refer to isomers having different spatial configurations of atoms, and examples thereof include optical isomers such as diastereomers and enantiomers, and geometric isomers. For example, in the case the compound of general formula (I) of the present invention has one or more chiral centers, the compound of general formula (I) of the present invention can be present in the form of optically pure enantiomers, a mixture of enantiomers such as racemates, optically pure diastereomers, a mixture of diastereomers, racemates of diastereomers or a mixture of racemates of diastereomers.

Examples of pharmacologically acceptable salts of the compound of general formula (I) of the present invention include inorganic acid salts such as hydrochlorides, hydrobromides, hydroiodides, nitrates, sulfates or phosphates, and organic acid salts such as acetates, trifluoroacetates, benzoates, oxalates, malonates, succinates, maleates, fumarates, tartrates, citrates, methanesulfonates, ethanesulfonates, trifluoromethanesulfonates, benzenesulfonates, p-toluenesulfonates, glutamates or aspartates. Preferable aspects of organic acid salts consist of salts of dicarboxylic acids such as oxalates, malonates, succinates, maleates, fumarates and tartrates.

Other examples of pharmacologically acceptable salts of the compound of general formula (I) of the present invention include metal salts such as sodium salts, potassium salts, calcium salts or magnesium salts, inorganic salts such as ammonium salts, and organic amine salts such as triethylamine salts or guanidine salts.

The compound of general formula (I) of the present invention, or a pharmacologically acceptable salt thereof, may be a pharmacologically acceptable solvate. A preferable aspect of a solvate is a hydrate. The hydrate may be a product of moisture absorption by the compound of general formula (I) of the present invention or a pharmacologically acceptable salt thereof.

The compound of general formula (I) of the present invention or a pharmacologically acceptable salt thereof may exhibit crystal polymorphism in the case of being a crystal. Crystal polymorphism refers to the same substance having different crystal structures. Each crystal or a mixture thereof at any arbitrary ratio is included in the present invention.

The following provides a detailed explanation of embodiments of the present invention.

The present invention relates to a compound of general formula (I):

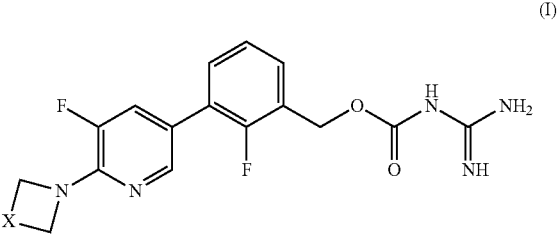

wherein,
X is a $CR^1R^2$, a carbonyl group or a group of formula (Ia):

$R^1$ and $R^2$, independently of each other, are a hydrogen atom, halogen atom, hydroxy group, protected hydroxy group, optionally substituted $C_1$-$C_6$ alkyl group or optionally substituted $C_1$-$C_6$ alkoxy group, where the term "substituted" refers to being substituted with at least one substituent selected from the group consisting of a deuterium atom, halogen atom, hydroxy group and $C_1$-$C_6$ alkoxy group, and p and q, independently of each other, are integers from 0 to 3, provided that the sum of p and q is 2 or more, or to a pharmacologically acceptable salt thereof.

In a specific embodiment, the present invention relates to the compound of general formula (I) according to the present invention, or a pharmacologically acceptable salt thereof, wherein X is $CR^1R^2$. Specifically, such a compound is represented by general formula (II) below:

General formula (II)

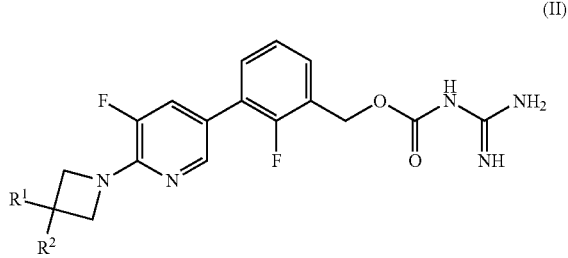

In general formula (II), $R^1$ and $R^2$ are the same as defined in general formula (I).

In a specific embodiment, the present invention relates to the compound of general formula (I) or (II) according to the present invention, or a pharmacologically acceptable salt thereof, wherein $R^1$ and $R^2$ are each independently a hydrogen atom, halogen atom, hydroxy group, optionally substituted $C_1$-$C_6$ alkyl group or optionally substituted $C_1$-$C_6$ alkoxy group. Here, the "substituted $C_1$-$C_6$ alkyl group" or "substituted $C_1$-$C_6$ alkoxy group" is substituted with at least one substituent selected from the group consisting of a deuterium atom, halogen atom, hydroxy group and $C_1$-$C_6$ alkoxy group, is preferably substituted with at least one substituent selected from the group consisting of a deuterium atom, halogen atom and hydroxy group, is more preferably substituted with at least one substituent selected from the group consisting of a deuterium atom and halogen atom, and is even more preferably substituted with at least one substituent selected from the group consisting of a deuterium atom and fluorine atom.

In a specific embodiment, the present invention relates to the compound of general formula (I) or (II) according to the present invention, or a pharmacologically acceptable salt thereof, wherein $R^1$ is a hydrogen atom, halogen atom, hydroxy group, optionally substituted $C_1$-$C_6$ alkyl group or optionally substituted $C_1$-$C_6$ alkoxy group.

In a specific embodiment, the present invention relates to the compound of general formula (I) or (II) according to the present invention, or a pharmacologically acceptable salt thereof, wherein $R^1$ is a halogen atom, hydroxy group, $C_1$-$C_6$ alkoxy group or $C_1$-$C_6$ alkoxy group substituted with at least one deuterium atom.

In a specific embodiment, the present invention relates to the compound of general formula (I) or (II) according to the present invention, or a pharmacologically acceptable salt thereof, wherein $R^2$ is a hydrogen atom, halogen atom or $C_1$-$C_3$ alkyl group.

The "substituted $C_1$-$C_6$ alkyl group" or "substituted $C_1$-$C_6$ alkoxy group" represented by $R^1$ and $R^2$ is substituted with at least one substituent selected from the group consisting of a deuterium atom, halogen atom, hydroxy group and $C_1$-$C_6$ alkoxy group, is preferably substituted with at least one substituent selected from the group consisting of a deuterium atom, halogen atom and hydroxy group, is more preferably substituted with at least one substituent selected from the group consisting of a deuterium atom and halogen atom, and is even more preferably substituted with at least one substituent selected from the group consisting of a deuterium atom and fluorine atom.

In a specific embodiment, the present invention relates to the compound of general formula (I) or (II) according to the present invention, or a pharmacologically acceptable salt thereof, wherein $R^1$ is a hydrogen atom, halogen atom, hydroxy group, optionally substituted $C_1$-$C_6$ alkyl group or optionally substituted $C_1$-$C_6$ alkoxy group, $R^2$ is a hydrogen atom, halogen atom or $C_1$-$C_3$ alkyl group, and the "substituted $C_1$-$C_6$ alkyl group" or "substituted $C_1$-$C_6$ alkoxy group" is substituted with at least one substituent selected from the group consisting of a deuterium atom and halogen atom (preferably fluorine atom).

In a specific embodiment, the present invention relates to the compound of general formula (I) or (II) according to the present invention, or a pharmacologically acceptable salt thereof, wherein $R^1$ is a halogen atom, hydroxy group, $C_1$-$C_6$ alkoxy group or $C_1$-$C_6$ alkoxy group substituted with at least one deuterium atom, and $R^2$ is a hydrogen atom, halogen atom or $C_1$-$C_3$ alkyl group.

In a specific embodiment, the present invention relates to the compound of general formula (I) or (II) according to the present invention, or a pharmacologically acceptable salt thereof, wherein $R^1$ and $R^2$ are each independently a hydrogen atom; fluorine atom, chlorine atom, bromine atom, iodine atom; hydroxy group; acetyloxy group, pivaloyloxy group, tetrahydropyran-2-yloxy group, tert-butyldimethylsilyloxy group, benzyloxy group, p-methoxybenzyloxy group, triphenylmethyloxy group; methyl group, ethyl group, isopropyl group, propyl group, butyl group, pentyl group, hexyl group; methoxy group, ethoxy group, propoxy group, isopropoxy group, butyloxy group, pentyloxy group, hexyloxy group; deuterated methyl group; 2-fluoroethyl group, 2,2-difluoroethyl group, 2,2,2-trifluoroethyl group, 3-fluoropropyl group; hydroxymethyl group, 2-hydroxyethyl group, 2-hydroxypropyl group, 3-hydroxypropyl group, 3-hydroxy-2-methylpropyl group, 4-hydroxybutyl group, 3-hydroxy-3-methylbutyl group, 3-hydroxy-2,2-dimethyl-propyl group, 2,3-dihydroxypropyl group, 3-hydroxy-2-(hydroxymethyl)-propyl group, 3-hydroxy-2-(hydroxymethyl)-2-methyl-propyl group, 3,4-dihydroxybutyl group; methoxymethyl group, ethoxymethyl group, propoxymethyl group, butyloxymethyl group, pentyloxymethyl group, hexyloxymethyl group, methoxyethyl group, ethoxyethyl group, propoxyethyl group, butyloxyethyl group, pentyloxyethyl group, hexyloxyethyl group, methoxypropyl group, ethoxypropyl group, propoxypropyl group, butoxybutyl group; 3-fluoro-2-(hydroxymethyl)propyl group, 2-fluoro-3-hydroxypropyl group; 2-hydroxy-3-methoxypropyl group, 3-hydroxy-2-methoxypropyl group, 3-hydroxy-2-(methoxymethyl)propyl group, 4-hydroxy-3-methoxybutyl group, 2-methoxy-3-(trityloxy)propyl group, 2-acetyloxy-3-methoxypropyl group; deuterated methoxy group; 2-fluoroethoxy group, 2,2-difluoroethoxy group, 2,2,2-trifluoroethoxy group, 3-fluoropropoxy group; hydroxymethoxy group, 2-hydroxyethoxy group, 2-hydroxypropoxy group, 3-hydroxypropoxy group, 3-hydroxy-2-methylpropoxy group, 4-hydroxybutoxy group, 3-hydroxy-3-methylbutoxy group, 3-hydroxy-2,2-dimethyl-propoxy group, 2,3-dihydroxypropoxy group, 3-hydroxy-2-(hydroxymethyl)-propoxy group, 3-hydroxy-2-(hydroxymethyl)-2-methyl-propoxy group, 3,4-dihydroxybutyloxy group; methoxymethoxy group, ethoxymethoxy group, propoxymethoxy group, butyloxymethoxy group, pentyloxymethoxy group, hexyloxymethoxy group, methoxyethoxy group, ethoxyethoxy group, propoxyethoxy group, butyloxyethoxy group, pentyloxyethoxy group, hexyloxyethoxy group, methoxypropoxy group, ethoxypropoxy group, propoxypropoxy group, butyloxybutyloxy group; 3-fluoro-2-(hydroxymethyl)propoxy group, 2-fluoro-3-hydroxypropoxy group; or 2-hydroxy-3-methoxypropoxy group, 3-hydroxy-2-methoxypropoxy group, 3-hydroxy-2-(methoxymethyl)propoxy group, 4-hydroxy-3-methoxybutyloxy group, 2-methoxy-3-(trityloxy)propoxy group or 2-acetyloxy-3-methoxypropoxy group.

In a specific embodiment, the present invention relates to the compound of general formula (I) or (II) according to the present invention, or a pharmacologically acceptable salt thereof, wherein $R^1$ and $R^2$ are each independently a hydrogen atom; fluorine atom, chlorine atom, bromine atom, iodine atom; hydroxy group; tetrahydropyran-2-yloxy group; methyl group, ethyl group, isopropyl group, propyl group, butyl group; methoxy group, ethoxy group, propoxy group, isopropoxy group, butyloxy group; deuterated methyl group; 2-fluoroethyl group, 2,2-difluoroethyl group, 2,2,2-trifluoroethyl group; hydroxymethyl group, 2-hydroxyethyl group; methoxymethyl group, methoxyethyl group; deuterated methoxy group; 2-fluoroethoxy group, 2,2-difluoroethoxy group, 2,2,2-trifluoroethoxy group; hydroxymethoxy group, 2-hydroxyethoxy group; or methoxymethoxy group or methoxyethoxy group.

In a specific embodiment, the present invention relates to the compound of general formula (I) or (II) according to the present invention, or a pharmacologically acceptable salt thereof, wherein $R^1$ and $R^2$ are each independently a hydrogen atom; fluorine atom; hydroxy group; tetrahydropyran-2-yloxy group; methyl group; methoxy group, ethoxy group, propoxy group, isopropoxy group; deuterated methoxy group; or 2-fluoroethoxy group.

In a specific embodiment, the present invention relates to the compound of general formula (I) or (II) according to the present invention, or a pharmacologically acceptable salt thereof, wherein $R^1$ is a fluorine atom; hydroxy group; methoxy group, ethoxy group, propoxy group, isopropoxy group; or deuterated methoxy group, and $R^2$ is a hydrogen atom; fluorine atom; or methyl group.

In another embodiment, the present invention relates to the compound of general formula (I) according to the present invention, or a pharmacologically acceptable salt thereof, wherein X is a carbonyl group. Specifically, such a compound is represented by general formula (III) below:

General formula (III)

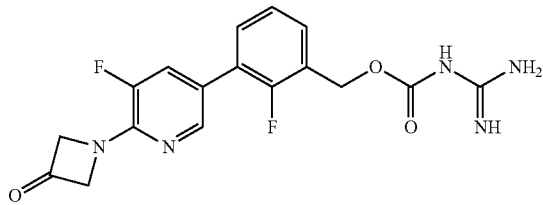

(III)

In another embodiment, the present invention relates to the compound of general formula (I) according to the present invention, or a pharmacologically acceptable salt thereof, wherein X is a group of formula (Ia). Specifically, such a compound is represented by general formula (IV) below:

General formula (IV)

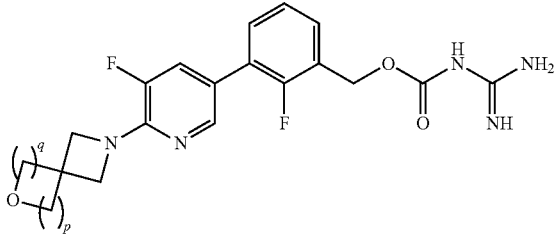

(IV)

In general formula (IV), p and q are the same as defined in general formula (I).

In another embodiment, the present invention relates to the compound of general formula (I) or (IV) according to the present invention, or a pharmacologically acceptable salt thereof, wherein p and q are each 1.

In another embodiment, the present invention relates to the compound of general formula (I) or (IV) according to the present invention, or a pharmacologically acceptable salt thereof, wherein p is 0 and q is 2 (or p is 2 and q is 0).

In another embodiment, the present invention relates to the compound of general formula (I) or (IV) according to the present invention, or a pharmacologically acceptable salt thereof, wherein p is 1 and q is 2 (or p is 2 and q is 1).

In another embodiment, the present invention relates to the compound of general formula (I) or (IV) according to the present invention, or a pharmacologically acceptable salt thereof, wherein p is 0 and q is 3 (or p is 3 and q is 0).

In another embodiment, the present invention relates to the compound of general formula (I) or (IV) according to the present invention, or a pharmacologically acceptable salt thereof, wherein p and q are each 2.

In another embodiment, the present invention relates to the compound of general formula (I) or (IV) according to the present invention, or a pharmacologically acceptable salt thereof, wherein p is 1 and q is 3 (or p is 3 and q is 1).

In another embodiment, the present invention relates to the compound of general formula (I) or (IV) according to the present invention, or a pharmacologically acceptable salt thereof, wherein p is 2 and q is 3 (or p is 3 and q is 2).

In a specific embodiment, the present invention relates to the compound of general formula (I), or a pharmacologically acceptable salt thereof, wherein the compound is:

2-fluoro-3-[5-fluoro-6-(3-methoxyazetidin-1-yl)pyridin-3-yl]benzyl carbamimidoylcarbamate (I-1), 2-fluoro-3-{5-fluoro-6-[3-(methoxy-$d_3$)azetidin-1-yl]pyridin-3-yl}benzyl carbamimidoylcarbamate (I-2), 3-[6-(3-ethoxyazetidin-1-yl)-5-fluoropyridin-3-yl]-2-fluorobenzyl carbamimidoylcarbamate (I-3), 2-fluoro-3-{5-fluoro-6-[3-(2-fluoroethoxy)azetidin-1-yl]pyridin-3-yl}benzyl carbamimidoylcarbamate (I-4), 2-fluoro-3-[5-fluoro-6-(3-propoxyazetidin-1-yl)pyridin-3-yl]benzyl carbamimidoylcarbamate (I-5), 2-fluoro-3-[5-fluoro-6-(3-isopropoxyazetidin-1-yl)pyridin-3-yl]benzyl carbamimidoylcarbamate (I-6), 3-[6-(3-butyloxyazetidin-1-yl)-5-fluoropyridin-3-yl]-2-fluorobenzyl carbamimidoylcarbamate (I-7), 3-{6-[3-(2,2-difluoroethoxy)azetidin-1-yl]-5-fluoropyridin-3-yl}-2-fluorobenzyl carbamimidoylcarbamate (I-8), 2-fluoro-3-{5-fluoro-6-[3-(2,2,2-trifluoroethoxy)azetidin-1-yl]-pyridin-3-yl}benzyl carbamimidoylcarbamate (I-9), 2-fluoro-3-{5-fluoro-6-[3-(2-hydroxyethoxy)azetidin-1-yl]-pyridin-3-yl}benzyl carbamimidoylcarbamate (I-10), 2-fluoro-3-{5-fluoro-6-[3-(2-methoxyethoxy)azetidin-1-yl]-pyridin-3-yl}benzyl carbamimidoylcarbamate (I-11), 2-fluoro-3-[5-fluoro-6-(3-hydroxyazetidin-1-yl)pyridin-3-yl]benzyl carbamimidoylcarbamate (I-12), 3-[6-(azetidin-1-yl)-5-fluoropyridin-3-yl]-2-fluorobenzyl carbamimidoylcarbamate (I-13), 2-fluoro-3-[5-fluoro-6-(3-fluoroazetidin-1-yl)pyridin-3-yl]benzyl carbamimidoylcarbamate (I-14), 3-[6-(3-chloroazetidin-1-yl)-5-fluoropyridin-3-yl]-2-fluorobenzyl carbamimidoylcarbamate (I-15), 3-[6-(3-bromoazetidin-1-yl)-5-fluoropyridin-3-yl]-2-fluorobenzyl carbamimidoylcarbamate (I-16), 2-fluoro-3-[5-fluoro-6-(3-iodoazetidin-1-yl)pyridin-3-yl]benzyl carbamimidoylcarbamate (I-17), 3-[6-(3,3-difluoroazetidin-1-yl)-5-fluoropyridin-3-yl]-2-fluoro-benzyl carbamimidoylcarbamate (I-18), 3-[6-(3-chloro-3-fluoroazetidin-1-yl)-5-fluoropyridin-3-yl]-2-fluorobenzyl carbamimidoylcarbamate (I-19), 2-fluoro-3-[5-fluoro-6-(3-methylazetidin-1-yl)pyridin-3-yl] benzyl carbamimidoylcarbamate (I-20), 3-[6-(3-ethylazetidin-1-yl)-5-fluoropyridin-3-yl]-2-fluorobenzyl carbamimidoylcarbamate (I-21), 2-fluoro-3-[5-fluoro-6-(3-propylazetidin-1-yl)pyridin-3-yl]benzyl carbamimidoylcarbamate (1-22),
2-fluoro-3-[5-fluoro-6-(3-isopropylazetidin-1-yl)pyridin-3-yl]benzyl carbamimidoylcarbamate (1-23),
2-fluoro-3-{5-fluoro-6-[3-(hydroxymethyl)azetidin-1-yl]pyridin-3-yl}benzyl carbamimidoylcarbamate (1-24),
2-fluoro-3-{5-fluoro-6-[3-(methoxymethyl)azetidin-1-yl]pyridin-3-yl}benzyl carbamimidoylcarbamate (I-25),
3-[6-(3,3-dimethylazetidin-1-yl)-5-fluoropyridin-3-yl]-2-fluorobenzyl carbamimidoylcarbamate (1-26),
3-[6-(3-ethyl-3-methylazetidin-1-yl)-5-fluoropyridin-3-yl]-2-fluorobenzyl carbamimidoylcarbamate (I-27),
2-fluoro-3-[5-fluoro-6-(3-methoxy-3-methylazetidin-1-yl)pyridin-3-yl]benzyl carbamimidoylcarbamate (1-28),
2-fluoro-3-{5-fluoro-6-[3-(methoxy-$d_3$)-3-methylazetidin-1-yl]pyridin-3-yl}benzyl carbamimidoylcarbamate (1-29),
2-fluoro-3-[5-fluoro-6-(3-hydroxy-3-methylazetidin-1-yl)pyridin-3-yl]benzyl carbamimidoylcarbamate (I-30),
3-[6-(3-ethyl-3-hydroxyazetidin-1-yl)-5-fluoropyridin-3-yl]-2-fluorobenzyl carbamimidoylcarbamate (1-31),
2-fluoro-3-[5-fluoro-6-(3-fluoro-3-methylazetidin-1-yl)pyridin-3-yl]benzyl carbamimidoylcarbamate (1-32),
2-fluoro-3-[5-fluoro-6-(3-oxoazetidin-1-yl)pyridin-3-yl]benzyl carbamimidoylcarbamate (1-33),
3-[6-(3,3-dihydroxyazetidin-1-yl)-5-fluoropyridin-3-yl]-2-fluorobenzyl carbamimidoylcarbamate (1-34),
2-fluoro-3-{5-fluoro-6-[3-hydroxy-3-methoxyazetidin-1-yl]pyridin-3-yl}benzyl carbamimidoylcarbamate (1-35),
3-[6-(3,3-dimethoxyazetidin-1-yl)-5-fluoropyridin-3-yl]-2-fluorobenzyl carbamimidoylcarbamate (1-36),
3-[6-(3-ethoxy-3-hydroxyazetidin-1-yl)-5-fluoropyridin-3-yl]-2-fluorobenzyl carbamimidoylcarbamate (1-37),
3-[6-(3-ethoxy-3-methoxyazetidin-1-yl)-5-fluoropyridin-3-yl]-2-fluorobenzyl carbamimidoylcarbamate (1-38),
3-[6-(3,3-diethoxyazetidin-1-yl)-5-fluoropyridin-3-yl]-2-fluorobenzyl carbamimidoylcarbamate (1-39),
2-fluoro-3-(5-fluoro-6-{3-[(tetrahydropyran-2-yl)oxy]azetidin-1-yl}pyridin-3-yl)benzyl carbamimidoylcarbamate (I-40),
2-fluoro-3-(5-fluoro-6-{3-methyl-3-[(tetrahydropyran-2-yl)oxy]azetidin-1-yl}pyridin-3-yl)benzyl carbamimidoylcarbamate (I-41),
2-fluoro-3-[5-fluoro-6-(2-oxa-6-azaspiro[3.3]heptan-6-yl)pyridin-3-yl]benzyl carbamimidoylcarbamate (1-42),
2-fluoro-3-[5-fluoro-6-(1-oxa-6-azaspiro[3.3]heptan-6-yl)pyridin-3-yl]benzyl carbamimidoylcarbamate (1-43),
2-fluoro-3-[5-fluoro-6-(6-oxa-2-azaspiro[3.4]octan-2-yl)pyridin-3-yl]benzyl carbamimidoylcarbamate (1-44),
2-fluoro-3-[5-fluoro-6-(5-oxa-2-azaspiro[3.4]octan-2-yl)pyridin-3-yl]benzyl carbamimidoylcarbamate (I-45),
2-fluoro-3-[5-fluoro-6-(7-oxa-2-azaspiro[3.5]nonan-2-yl)pyridin-3-yl]benzyl carbamimidoylcarbamate (1-46),
2-fluoro-3-[5-fluoro-6-(6-oxa-2-azaspiro[3.5]nonan-2-yl)pyridin-3-yl]benzyl carbamimidoylcarbamate (1-47), or
2-fluoro-3-[5-fluoro-6-(7-oxa-2-azaspiro[3.6]decan-2-yl)pyridin-3-yl]benzyl carbamimidoylcarbamate (1-48).

In a specific embodiment, the present invention relates to the compound of general formula (I), or a pharmacologically acceptable salt thereof, wherein the compound is:

2-fluoro-3-[5-fluoro-6-(3-methoxyazetidin-1-yl)pyridin-3-yl]benzyl carbamimidoylcarbamate,
2-fluoro-3-{5-fluoro-6-[3-(methoxy-$d_3$)azetidin-1-yl]pyridin-3-yl}benzyl carbamimidoylcarbamate,
3-[6-(3-ethoxyazetidin-1-yl)-5-fluoropyridin-3-yl]-2-fluorobenzyl carbamimidoylcarbamate,
2-fluoro-3-{5-fluoro-6-[3-(2-fluoroethoxy)azetidin-1-yl]pyridin-3-yl}benzyl carbamimidoylcarbamate,
2-fluoro-3-[5-fluoro-6-(3-propoxyazetidin-1-yl)pyridin-3-yl]benzyl carbamimidoylcarbamate,
2-fluoro-3-[5-fluoro-6-(3-isopropoxyazetidin-1-yl)pyridin-3-yl]benzyl carbamimidoylcarbamate,
2-fluoro-3-(5-fluoro-6-{3-[(tetrahydropyran-2-yl)oxy]azetidin-1-yl}pyridin-3-yl)benzyl carbamimidoylcarbamate,
2-fluoro-3-[5-fluoro-6-(3-hydroxyazetidin-1-yl)pyridin-3-yl]benzyl carbamimidoylcarbamate,
3-[6-(azetidin-1-yl)-5-fluoropyridin-3-yl]-2-fluorobenzyl carbamimidoylcarbamate,
2-fluoro-3-[5-fluoro-6-(3-fluoroazetidin-1-yl)pyridin-3-yl]benzyl carbamimidoylcarbamate,
3-[6-(3,3-difluoroazetidin-1-yl)-5-fluoropyridin-3-yl]-2-fluoro-benzyl carbamimidoylcarbamate,
2-fluoro-3-[5-fluoro-6-(3-methylazetidin-1-yl)pyridin-3-yl]benzyl carbamimidoylcarbamate,
3-[6-(3,3-dimethylazetidin-1-yl)-5-fluoropyridin-3-yl]-2-fluorobenzyl carbamimidoylcarbamate,
2-fluoro-3-(5-fluoro-6-{3-methyl-3-[(tetrahydropyran-2-yl)oxy]azetidin-1-yl}pyridin-3-yl)benzyl carbamimidoylcarbamate,
2-fluoro-3-[5-fluoro-6-(3-hydroxy-3-methylazetidin-1-yl)pyridin-3-yl]benzyl carbamimidoylcarbamate or
2-fluoro-3-[5-fluoro-6-(2-oxa-6-azaspiro[3.3]heptan-6-yl)pyridin-3-yl]benzyl carbamimidoylcarbamate.

In a specific embodiment, the present invention relates to 2-fluoro-3-[5-fluoro-6-(3-methoxyazetidin-1-yl)pyridin-3-yl]benzyl carbamimidoylcarbamate, or a pharmacologically acceptable salt thereof.

In a specific embodiment, the present invention relates to 2-fluoro-3-{5-fluoro-6-[3-(methoxy-$d_3$)azetidin-1-yl]pyridin-3-yl}benzyl carbamimidoylcarbamate, or a pharmacologically acceptable salt thereof.

In a specific embodiment, the present invention relates to 2-fluoro-3-[5-fluoro-6-(3-hydroxyazetidin-1-yl)pyridin-3-yl]benzyl carbamimidoylcarbamate, or a pharmacologically acceptable salt thereof.

In a specific embodiment, the present invention relates to 2-fluoro-3-[5-fluoro-6-(3-fluoroazetidin-1-yl)pyridin-3-yl]benzyl carbamimidoylcarbamate, or a pharmacologically acceptable salt thereof.

In a specific embodiment, the present invention relates to 2-fluoro-3-[5-fluoro-6-(3-hydroxy-3-methylazetidin-1-yl)pyridin-3-yl]benzyl carbamimidoylcarbamate, or a pharmacologically acceptable salt thereof.

In a specific embodiment, the present invention relates to 2-fluoro-3-[5-fluoro-6-(2-oxa-6-azaspiro[3.3]heptan-6-yl)pyridin-3-yl]benzyl carbamimidoylcarbamate, or a pharmacologically acceptable salt thereof.

Examples of the compounds of general formula (I) of the present invention are listed in [Table 1] to [Table 4]. In the following formulae I-1 to 1-48, D denotes a deuterium atom.

TABLE 1
| Compound No. | |
|---|---|
| I-1 | 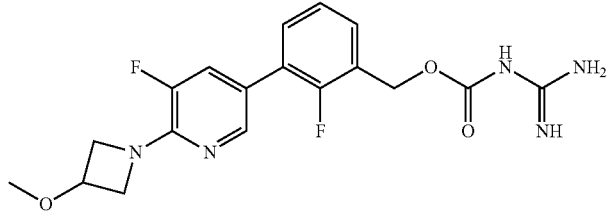 [SMILES: COC1CN(c2ncc(-c3cccc(COC(=O)NC(=N)N)c3F)cc2F)C1] |
| I-2 | 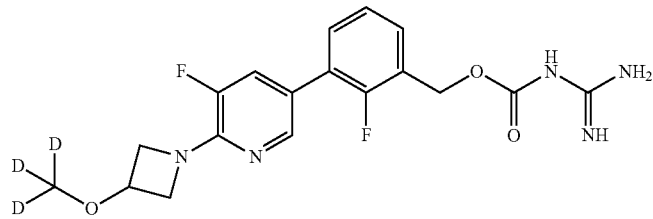 [SMILES: [2H]C([2H])([2H])OC1CN(c2ncc(-c3cccc(COC(=O)NC(=N)N)c3F)cc2F)C1] |
| I-3 | 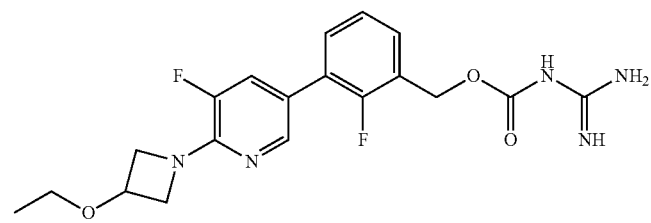 [SMILES: CCOC1CN(c2ncc(-c3cccc(COC(=O)NC(=N)N)c3F)cc2F)C1] |
| I-4 | 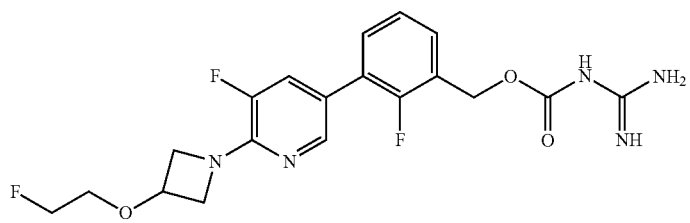 [SMILES: N=C(N)NC(=O)OCc1cccc(-c2cnc(N3CC(OCCF)C3)c(F)c2)c1F] |
| I-5 | 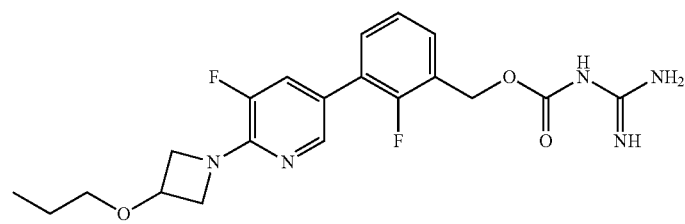 [SMILES: CCCOC1CN(c2ncc(-c3cccc(COC(=O)NC(=N)N)c3F)cc2F)C1] |
| I-6 | 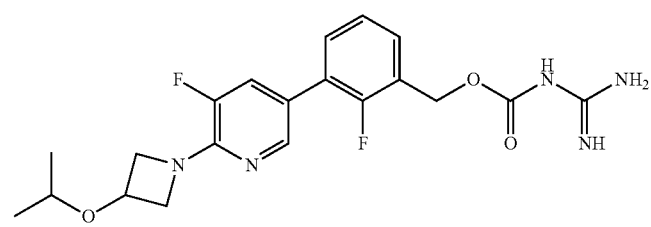 [SMILES: CC(C)OC1CN(c2ncc(-c3cccc(COC(=O)NC(=N)N)c3F)cc2F)C1] |
| I-7 | 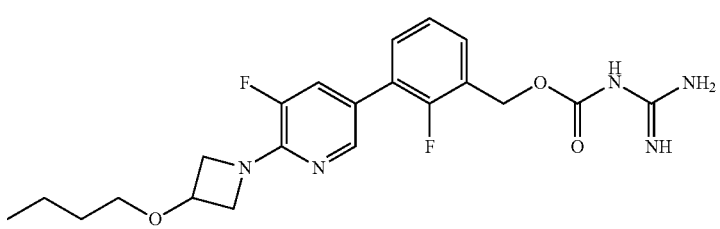 [SMILES: CCCCOC1CN(c2ncc(-c3cccc(COC(=O)NC(=N)N)c3F)cc2F)C1] |

TABLE 1-continued
| Compound No. | |
|---|---|
| I-8 | 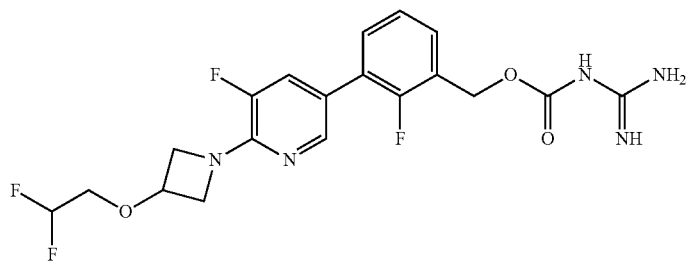 [SMILES: N=C(N)NC(=O)OCc1cccc(-c2cnc(N3CC(OCC(F)F)C3)c(F)c2)c1F] |
| I-9 | 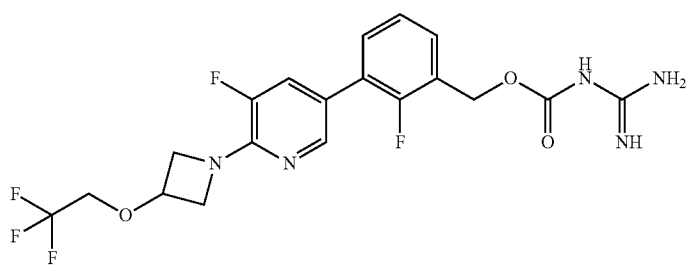 [SMILES: N=C(N)NC(=O)OCc1cccc(-c2cnc(N3CC(OCC(F)(F)F)C3)c(F)c2)c1F] |
| I-10 | 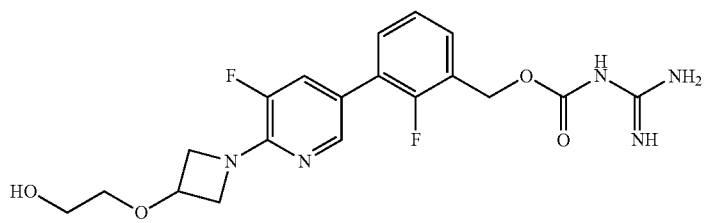 [SMILES: N=C(N)NC(=O)OCc1cccc(-c2cnc(N3CC(OCCO)C3)c(F)c2)c1F] |
| I-11 | 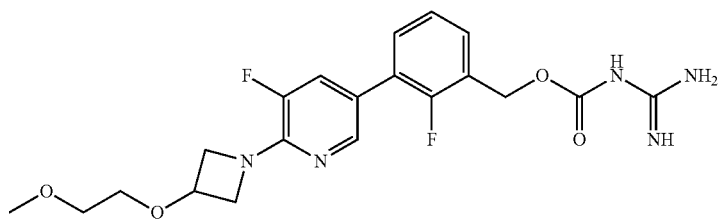 [SMILES: COCCOC1CN(c2ncc(-c3cccc(COC(=O)NC(=N)N)c3F)cc2F)C1] |
| I-12 | 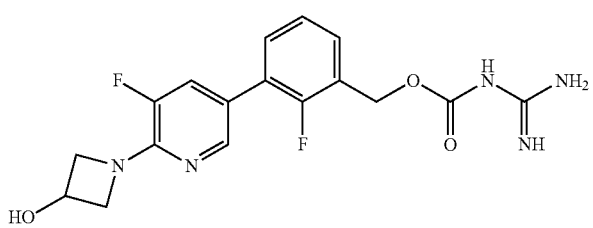 [SMILES: N=C(N)NC(=O)OCc1cccc(-c2cnc(N3CC(O)C3)c(F)c2)c1F] |

TABLE 2
| Compound No. | |
|---|---|
| I-13 | 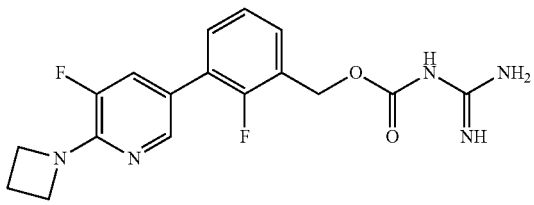 [SMILES: N=C(N)NC(=O)OCc1cccc(-c2cnc(N3CCC3)c(F)c2)c1F] |
| I-14 | 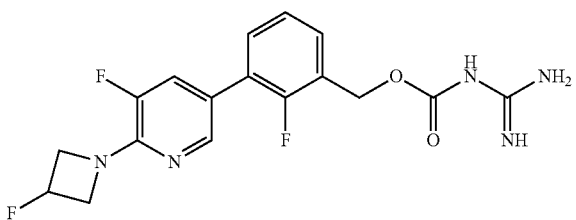 [SMILES: N=C(N)NC(=O)OCc1cccc(-c2cnc(N3CC(F)C3)c(F)c2)c1F] |
| I-15 | 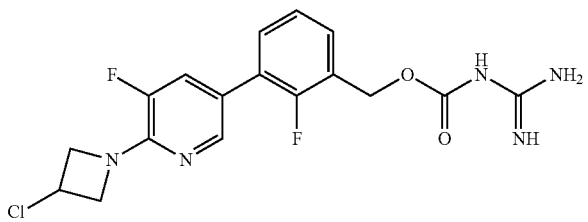 [SMILES: N=C(N)NC(=O)OCc1cccc(-c2cnc(N3CC(Cl)C3)c(F)c2)c1F] |
| I-16 | 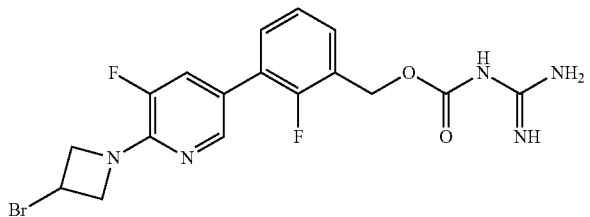 |
| I-17 | 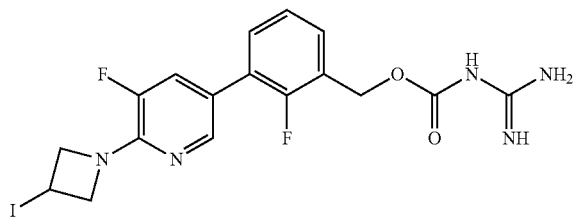 [SMILES: N=C(N)NC(=O)OCc1cccc(-c2cnc(N3CC(I)C3)c(F)c2)c1F] |
| I-18 | 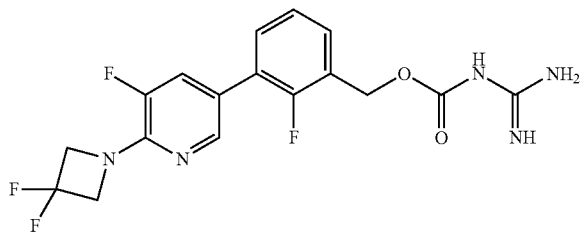 [SMILES: N=C(N)NC(=O)OCc1cccc(-c2cnc(N3CC(F)(Cl)C3)c(F)c2)c1F] |

TABLE 2-continued

| Compound No. |
|---|
| I-19 |
| I-20 |
| I-21 |
| I-22 |
| I-23 |
| I-24 |

TABLE 3
| Compound No. | |
|---|---|
| I-25 | 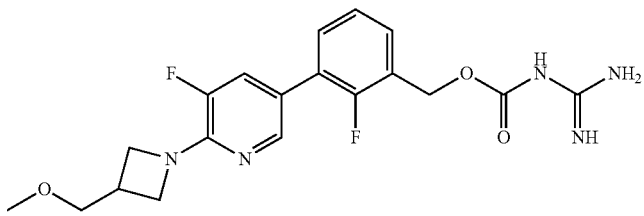 [SMILES: COCC1CN(c2ncc(-c3cccc(COC(=O)NC(=N)N)c3F)cc2F)C1] |
| I-26 | 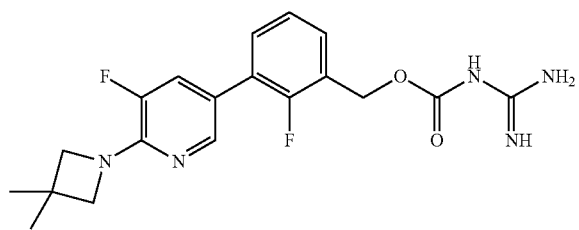 [SMILES: CC1(C)CN(c2ncc(-c3cccc(COC(=O)NC(=N)N)c3F)cc2F)C1] |
| I-27 | 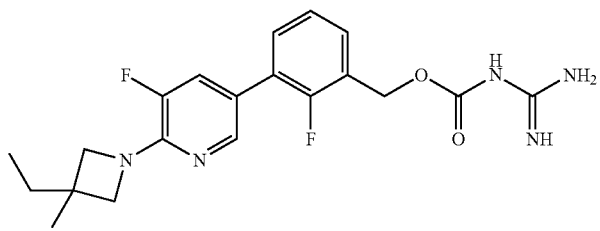 [SMILES: CCC1(C)CN(c2ncc(-c3cccc(COC(=O)NC(=N)N)c3F)cc2F)C1] |
| I-28 | 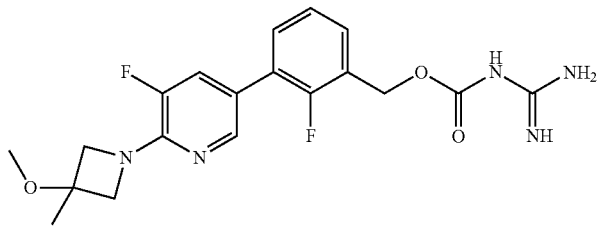 |
| I-29 | 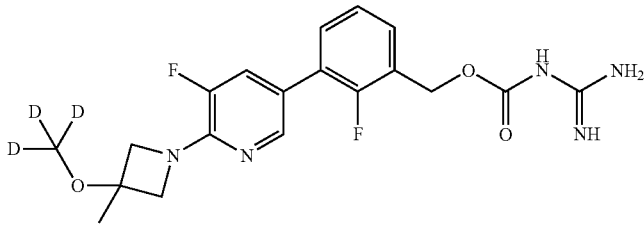 [SMILES: [2H]C([2H])([2H])OC1(C)CN(c2ncc(-c3cccc(COC(=O)NC(=N)N)c3F)cc2F)C1] |
| I-30 | 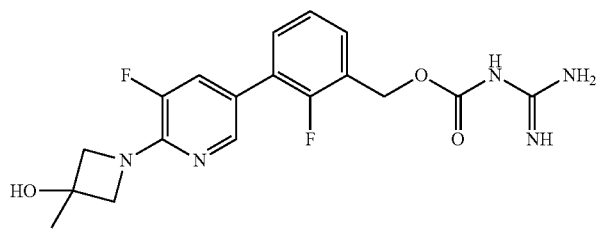 [SMILES: CC1(O)CN(c2ncc(-c3cccc(COC(=O)NC(=N)N)c3F)cc2F)C1] |

TABLE 3-continued
| Compound No. | |
|---|---|
| I-31 | 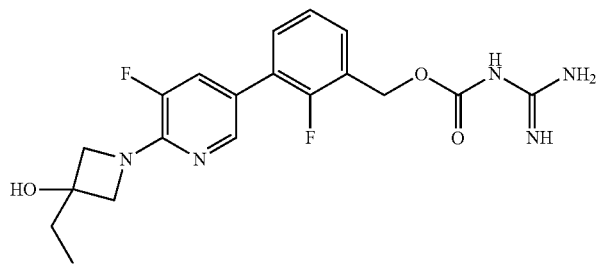 |
| I-32 | 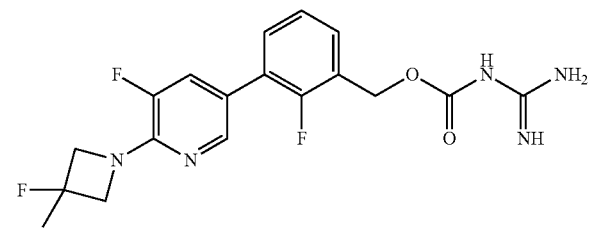 [SMILES: CC1(F)CN(c2ncc(-c3cccc(COC(=O)NC(=N)N)c3F)cc2F)C1] |
| I-33 | 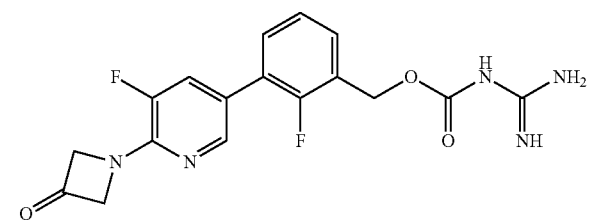 [SMILES: N=C(N)NC(=O)OCc1cccc(-c2cnc(N3CC(=O)C3)c(F)c2)c1F] |
| I-34 | 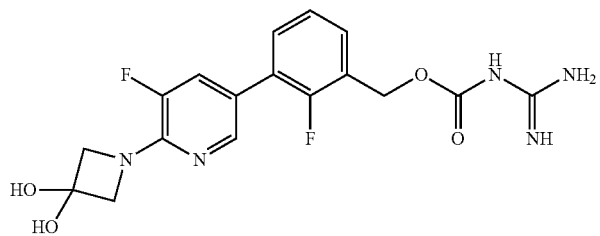 [SMILES: N=C(N)NC(=O)OCc1cccc(-c2cnc(N3CC(O)(O)C3)c(F)c2)c1F] |
| I-35 | 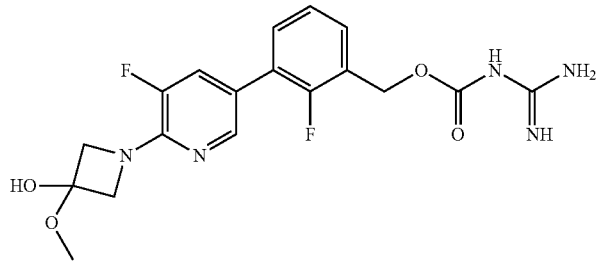 |
| I-36 | 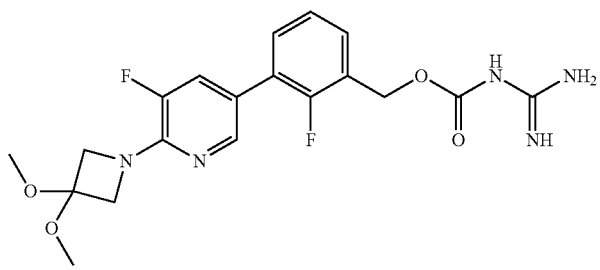 [SMILES: COC1(OC)CN(c2ncc(-c3cccc(COC(=O)NC(=N)N)c3F)cc2F)C1] |

TABLE 4
| Compound No. | |
|---|---|
| I-37 | 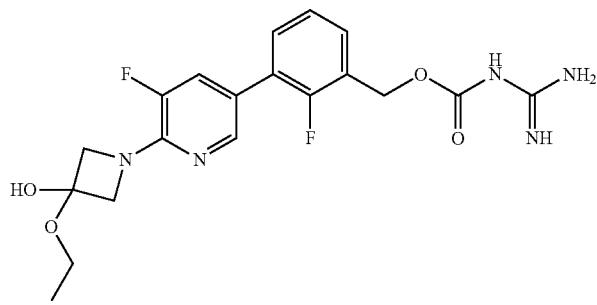 [SMILES: CCOC1(O)CN(c2ncc(-c3cccc(COC(=O)NC(=N)N)c3F)cc2F)C1] |
| I-38 | 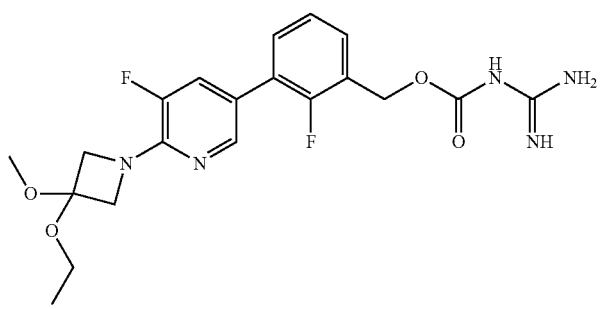 [SMILES: CCOC1(OC)CN(c2ncc(-c3cccc(COC(=O)NC(=N)N)c3F)cc2F)C1] |
| I-39 | 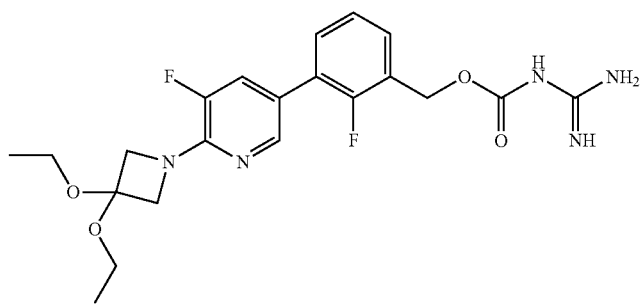 [SMILES: CCOC1(OCC)CN(c2ncc(-c3cccc(COC(=O)NC(=N)N)c3F)cc2F)C1] |
| I-40 | 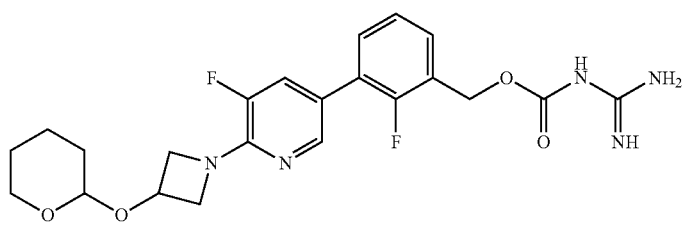 [SMILES: N=C(N)NC(=O)OCc1cccc(-c2cnc(N3CC(OC4CCCCO4)C3)c(F)c2)c1F] |
| I-41 | 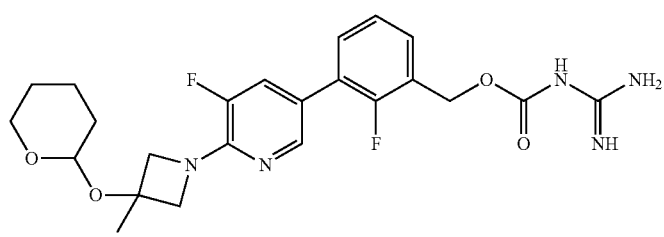 [SMILES: CC1(OC2CCCCO2)CN(c2ncc(-c3cccc(COC(=O)NC(=N)N)c3F)cc2F)C1] |

TABLE 4-continued
| Compound No. | |
|---|---|
| I-42 | 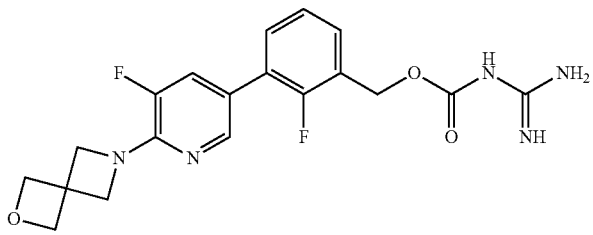 [SMILES: N=C(N)NC(=O)OCc1cccc(-c2cnc(N3CC4(COC4)C3)c(F)c2)c1F] |
| I-43 | 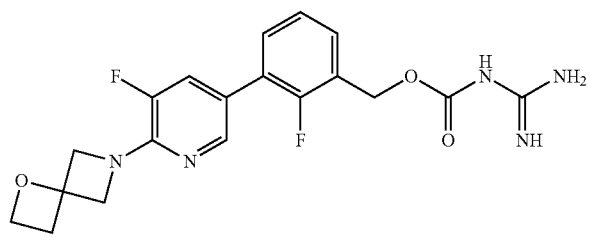 [SMILES: N=C(N)NC(=O)OCc1cccc(-c2cnc(N3CC4(CCO4)C3)c(F)c2)c1F] |
| I-44 | 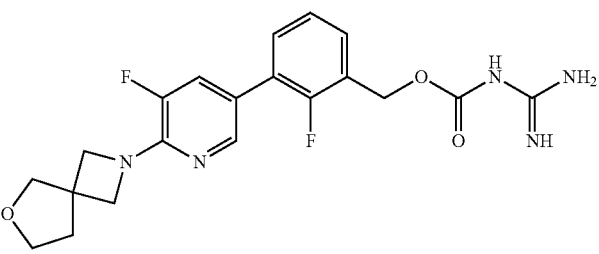 [SMILES: N=C(N)NC(=O)OCc1cccc(-c2cnc(N3CC4(CCOC4)C3)c(F)c2)c1F] |
| I-45 | 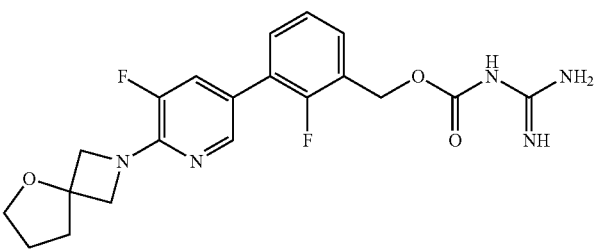 [SMILES: N=C(N)NC(=O)OCc1cccc(-c2cnc(N3CC4(CCCO4)C3)c(F)c2)c1F] |
| I-46 | 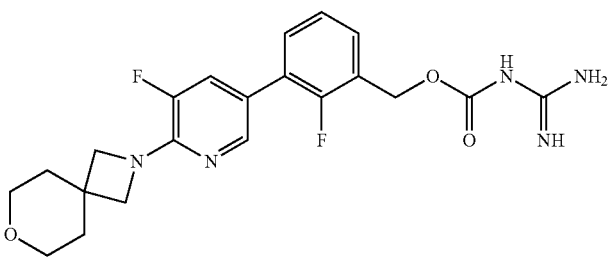 [SMILES: N=C(N)NC(=O)OCc1cccc(-c2cnc(N3CC4(CCOCC4)C3)c(F)c2)c1F] |
| I-47 | 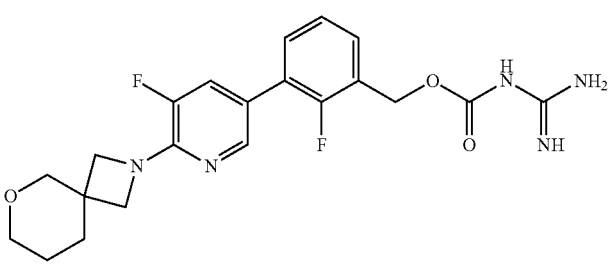 [SMILES: N=C(N)NC(=O)OCc1cccc(-c2cnc(N3CC4(CCCOC4)C3)c(F)c2)c1F] |

TABLE 4-continued

| Compound No. | |
|---|---|
| I-48 | 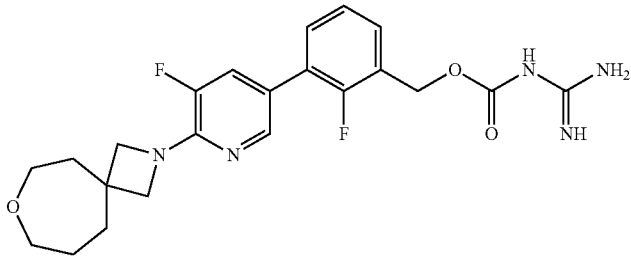 [SMILES: N=C(N)NC(=O)OCc1cccc(-c2cnc(N3CC4(CCCOCC4)C3)c(F)c2)c1F] |

The following indicates a typical method for producing a compound of general formula (I) of the present invention, or a pharmacologically acceptable salt thereof. Furthermore, the compound of the present invention, or a pharmacologically acceptable salt thereof, is not limited to a compound, or pharmacologically acceptable salt thereof, produced according to the production method indicated below.

In the production method indicated below, in the case the compound contains a partial structure (such as a hydroxyl group) that inhibits a desired reaction or is susceptible to side reaction, the desired reaction can be carried out by introducing a protecting group into that partial structure and the target compound can be obtained by subsequently removing the protecting group. Reactions for introducing and removing protecting groups can be carried out according to methods routinely used in synthetic organic chemistry (such as the method described in Protective Groups in Organic Synthesis, 4th Edition, T. W. Greene and P. G. M. Wuts, ed., John Wiley & Sons Inc. (2006)). In addition, specific production methods for individual compounds of the present invention are explained later in Examples.

(Production Method 1)

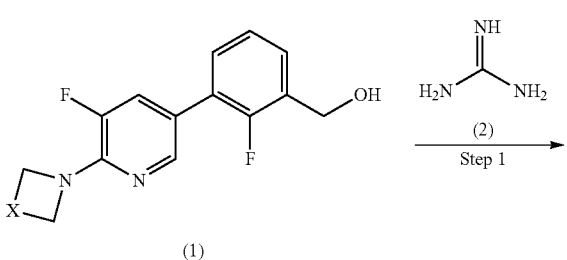

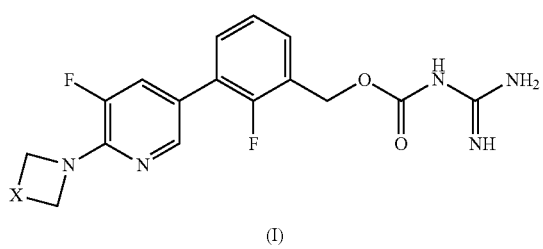

X is a $CR^1R^2$, a carbonyl group or a group of formula (Ia):

$R^1$ and $R^2$, independently of each other, are a hydrogen atom, halogen atom, hydroxy group, protected hydroxy group, optionally substituted $C_1$-$C_6$ alkyl group or optionally substituted $C_1$-$C_6$ alkoxy group, where the term "substituted" refers to being substituted with at least one substituent selected from the group consisting of a deuterium atom, halogen atom, hydroxy group and $C_1$-$C_6$ alkoxy group, and p and q, independently of each other, are integers from 0 to 3, with the proviso that the sum of p and q is 2 or more.

Step 1 of Production Method 1 is a step for reacting Compound (1) and guanidine or a guanidine acid salt as Compound (2) in a solvent in the presence of 1,1'-carbonyldiimidazole to produce a compound of general formula (I).

Compound (1) can be produced according to Syntheses 1 to 3 described later and Reference Examples of the present description.

Examples of guanidine acid salts as Compounds (2) include guanidine hydrochloride, guanidine sulfate and guanidine carbonate.

Compound (2) is known and is available from a reagent supplier such as Tokyo Chemical Industry Co., Ltd. The amount of guanidine or guanidine acid salt used based on 1 mole of Compound (1) is normally 0.9 times to 5 times the molar amount, and preferably 1.1 times to 3 times the molar amount of Compound (1).

There are no particular limitations on the solvent used provided it does not inhibit the reaction and dissolves the raw materials to a certain degree, and examples thereof include aromatic hydrocarbons such as benzene, toluene or xylene, halogenated aliphatic hydrocarbons such as methylene chloride, chloroform or 1,2-dichloroethane, ethers such as tetrahydrofuran, 1,2-dimethoxyethane or 1,4-dioxane, nitriles such as acetonitrile or propionitrile, amides such as N,N-dimethylformamide, N,N-dimethylacetamide or N-methylpyrrolidone, and arbitrarily mixed solvents thereof. N,N-dimethylformamide is used preferably. Although there are no particular limitations thereon, the amount of solvent used is normally 1 time to 20 times, and preferably 2 times to 10 times the mass of Compound (1).

The amount of 1,1'-carbonyldiimidazole used based on 1 mole of Compound (1) is normally 0.9 times to 5 times the molar amount, and preferably 1.1 times to 3 times the molar amount of Compound (1).

Although variable according to such factors as the types and amounts used of the raw materials, solvent and the like, the reaction temperature is normally −20° C. to 150° C. and preferably 0° C. to 40° C.

Although variable according to such factors as the reaction temperature, the reaction time is normally 1 minute to 48 hours and preferably 1 hour to 24 hours.

Although the reaction pressure may be suitably set as necessary and the reaction may be carried out under increased pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

In the case a protecting group is present in Compound (1), Compound (1) can be further subjected to a deprotection step as necessary.

In the case Compound (1) has at least two different types of protecting groups, only one type of protecting group can be selectively removed by selecting the deprotection conditions.

Deprotection conditions can be suitably selected according to a method routinely used in synthetic organic chemistry (such as the method described in Protective Groups in Organic Synthesis, 4th Edition, T. W. Greene and P. G. M. Wuts, ed., John Wiley & Sons Inc. (2006)) or Examples of the present description.

The aforementioned Compound (1) can be suitably prepared according to, for example, the following Syntheses 1 to 3 and Reference Examples of the present description.
(Synthesis 1)

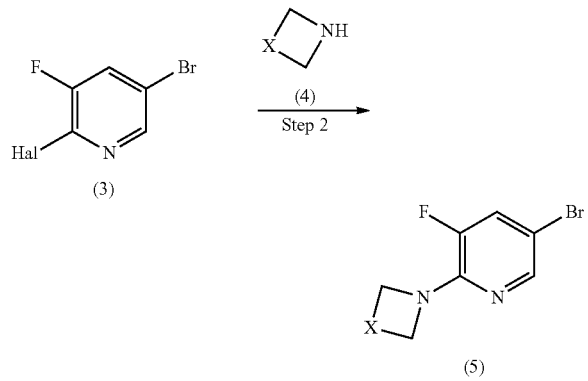

X is as previously described and Hal represents a halogen atom.

Step 2 of Synthesis 1 is a step for obtaining Compound (5) by reacting Compound (3) and Compound (4) in a solvent and in the presence of a base.

Compound (3) is known and is available from reagent suppliers. Examples of such compounds include 5-bromo-2,3-difluoropyridine. Alternatively, Compound (3) can be produced from known compounds according to known methods.

Compound (4) is known and is available from reagent suppliers. Examples of such compounds include azetidine, azetidin-3-ol, 3-methylazetidine, 3,3-dimethylazetidine, 3-fluoroazetidine, 3,3-difluoroazetidine, 2-oxa-6-azaspiro[3,3]heptane, and acid salts thereof. Alternatively, Compound (4) can be produced from known compounds according to known methods.

Examples of acid salts as Compounds (4) include hydrochlorides, sulfates, acetates and oxalates.

The amount of Compound (4) used based on 1 mole of Compound (3) is normally 0.9 times to 5 times the molar amount, and preferably 1.1 times to 3 times the molar amount of Compound (3).

There are no particular limitations on the solvent used provided it does not inhibit the reaction and dissolves the raw materials to a certain degree, and examples thereof include alcohols such as methanol, ethanol, propanol or isopropanol, aromatic hydrocarbons such as benzene, toluene or xylene, halogenated aliphatic hydrocarbons such as methylene chloride, chloroform or 1,2-dichloroethane, ethers such as tetrahydrofuran, 1,2-dimethoxyethane or 1,4-dioxane, nitriles such as acetonitrile or propionitrile, amides such as N,N-dimethylformamide, N,N-dimethylacetamide or N-methylpyrrolidone, sulfoxides such as dimethylsulfoxide, and arbitrarily mixed solvents thereof. Alcohols such as ethanol, amides such as N,N-dimethylformamide or N-methylpyrrolidone, or sulfoxides such as dimethylsulfoxide are used preferably.

Although there are no particular limitations thereon, the amount of solvent used is normally 1 time to 50 times, and preferably 5 times to 20 times the mass of Compound (3).

Examples of base used include alkali metal acetates such as sodium acetate or potassium acetate, alkali metal carbonates such as sodium carbonate, potassium carbonate or cesium carbonate, and organic bases such as triethylamine or diisopropylethylamine, with potassium carbonate, cesium carbonate, triethylamine or diisopropylethylamine being preferable. The amount of base used based on 1 mole of Compound (3) is normally 0.9 times to 10 times the molar amount, and preferably 1 time to 5 times the molar amount of Compound (3).

Although variable according to such factors as the types and amounts used of the raw materials, solvent and the like, the reaction temperature is normally 0° C. to 150° C. and preferably 40° C. to 120° C.

Although variable according to such factors as the reaction temperature, the reaction time is normally 1 minute to 48 hours and preferably 0.5 hours to 24 hours.

Although the reaction pressure may be suitably set as necessary and the reaction may be carried out under increased pressure, reduced pressure or atmospheric pressure, the reaction pressure is preferably atmospheric pressure. Although the reaction can be carried out in an atmosphere suitably selected as necessary, the reaction atmosphere is preferably an air atmosphere or an inert gas atmosphere such as that of nitrogen or argon.

In the case a functional group (such as a halogen atom, hydroxy group or carbonyl group) is present in Compound (5), Compound (5) can be further converted into the desired form by reacting the functional group with an appropriate reagent in accordance with a known method (see, for example, Reference Examples 2-1 to 2-5, 8, 9, and 12 to 14).
(Synthesis 2)

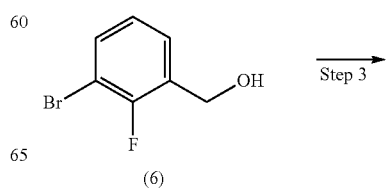

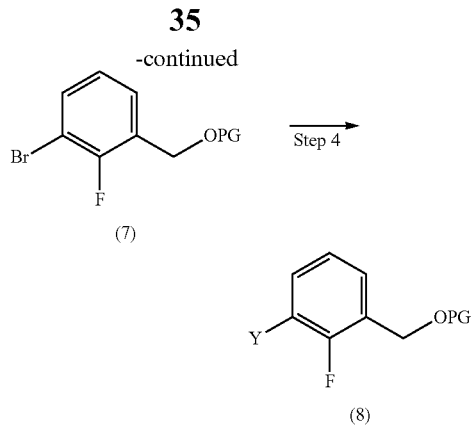

PG represents a protecting group, and Y represents a boronic acid group or boronate ester substituent. Examples of the boronate ester substituent Y include a diisopropyl boronate group, pinacol boronate group, neopentyl glycol boronate group and catechol boronate group.

Step 3 of Synthesis 2 is a step for obtaining Compound (7) by introducing a protecting group onto the hydroxyl group of Compound (6) in a solvent.

Compound (6), namely (2-bromo-3-fluorophenyl)methanol, is known or can be produced from known compounds according to a known method.

Introduction of a protecting group onto the hydroxyl group can be suitably carried out according to the known art, such as that described in Protective Groups in Organic Synthesis, 4th Edition, T. W. Greene and P. G. M. Wuts, ed., John Wiley & Sons Inc., or Examples of the present description.

Step 4 of Synthesis 2 is a step for obtaining Compound (8) by reacting Compound (7) with a borylation reagent in the presence of a palladium catalyst and base and in a solvent and in an inert gas atmosphere to introduce a boronic acid group or boronate ester substituent.

The borylation reagent is known or can be produced from known compounds according to a known method. Examples of borylation reagents include trimethyl borate, triisopropyl borate, bis(pinacolato)diborane, bis(neopentylglycolato)diborane and bis(catecholato)diborane. The amount of the borylation reagent used based on 1 mole of Compound (7) is normally 0.9 times to 5 times the molar amount, and preferably 1.1 times to 3 times the molar amount of Compound (7).

There are no particular limitations on the solvent used provided it does not inhibit the reaction and dissolves the raw materials, base and catalyst to a certain degree, and examples thereof include aromatic hydrocarbons such as benzene or toluene, ethers such as tetrahydrofuran, 1,2-dimethoxyethane or 1,4-dioxane, alcohols such as methanol, ethanol, propanol or isopropanol, amides such as N,N-dimethylformamide, N,N-dimethylacetamide or N-methylpyrrolidone, sulfoxides such as dimethylsulfoxide, nitriles such as acetonitrile, water, and arbitrarily mixed solvents thereof, with toluene, 1,4-dioxane, N,N-dimethylformamide, dimethylsulfoxide or acetonitrile being preferable.

Examples of the inert gas used include nitrogen, helium and argon.

Examples of the palladium catalyst used include organic palladium complexes such as tetrakis(triphenylphosphine)palladium, bis(triphenylphosphine)palladium dichloride or 1,1'-bis(diphenylphosphino)ferrocene palladium dichloride, with 1,1'-bis(diphenylphosphino)ferrocene palladium (II) dichloride being preferable. The amount of palladium used as catalyst based on 1 mole of Compound (7) is normally 0.0001 time to 1 time the molar amount, and preferably 0.005 times to 0.3 times the molar amount of Compound (7).

Examples of base used include alkali metal acetates such as sodium acetate or potassium acetate, alkali metal carbonates such as sodium carbonate, potassium carbonate or cesium carbonate, and organic bases such as triethylamine or diisopropylethylamine, with sodium acetate, potassium acetate or triethylamine being preferable. The amount of base used based on 1 mole of Compound (7) is normally 1 time to 10 times the molar amount, and preferably 1 time to 5 times the molar amount of Compound (7).

Although variable according to such factors as the types and amounts used of the raw materials, solvent and the like, the reaction temperature is normally 0° C. to 200° C. and preferably 30° C. to 150° C.

Although variable according to such factors as the reaction temperature, the reaction time is normally 10 minutes to 120 hours and preferably 0.5 hours to 48 hours.

Although the reaction pressure may be suitably set as necessary and the reaction may be carried out under increased pressure, reduced pressure or atmospheric pressure, the reaction pressure is preferably atmospheric pressure.

(Synthesis 3)

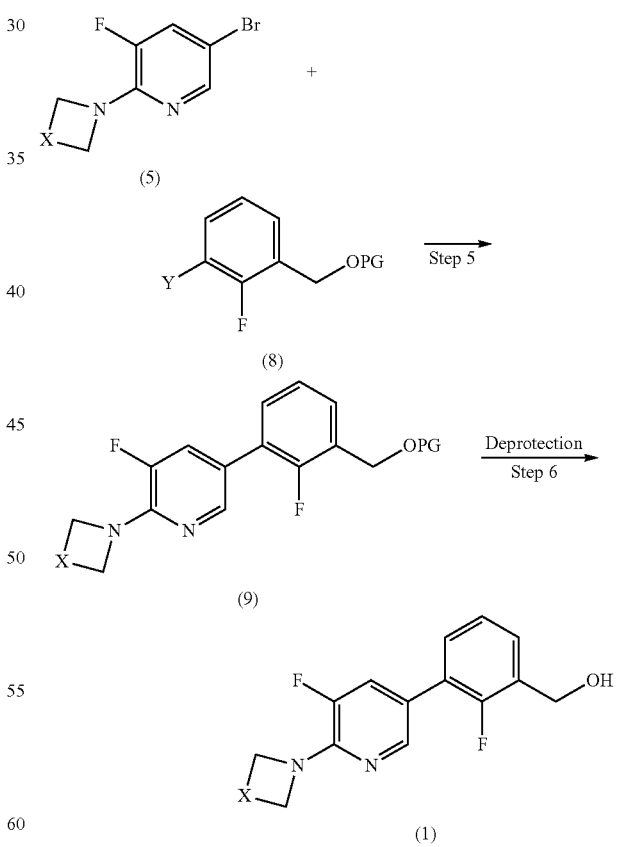

X, Y and PG are as previously described.

Step 5 of Synthesis 3 is a so-called Suzuki reaction for obtaining Compound (9) by reacting Compound (5) and Compound (8) in a solvent and in the presence of a base or fluoride and a palladium catalyst in an inert gas atmosphere.

Compound (5) can be produced according to the aforementioned Synthesis 1. Compound (8) can be produced according to the aforementioned Synthesis 2. The amount of Compound (8) used based on 1 mole of Compound (5) is normally 0.8 times to 3 times the molar amount, and preferably 0.9 times to 1.5 times the molar amount of Compound (5).

There are no particular limitations on the inert solvent used provided it does not inhibit the reaction and dissolves the raw materials, catalyst and base (or fluoride) to a certain degree, and examples thereof include aromatic hydrocarbons such as benzene or toluene, ethers such as tetrahydrofuran, 1,2-dimethoxyethane or 1,4-dioxane, alcohols such as methanol, ethanol, propanol or isopropanol, esters such as methyl acetate or ethyl acetate, amides such as N,N-dimethylformamide, N,N-dimethylacetamide or N-methylpyrrolidone, sulfoxides such as dimethylsulfoxide, nitriles such as acetonitrile, water, and arbitrarily mixed solvents thereof, with 1,2-dimethoxyethane, mixed solvent of 1,2-dimethoxyethane and water, 1,4-dioxane, mixed solvent of 1,4-dioxane and water, toluene, mixed solvent of toluene, ethanol and water, or mixed solvent of toluene and water being preferable.

Examples of the inert gas used include nitrogen, helium and argon.

Examples of the palladium catalyst used include metal palladium catalysts such as palladium-activated carbon or palladium black, organic palladium complexes such as tetrakis(triphenylphosphine)palladium, bis(triphenylphosphine)palladium dichloride, 1,1'-bis(diphenylphosphino)ferrocene palladium dichloride or tris(dibenzylideneacetone)dipalladium, and palladium salts such as palladium chloride or palladium acetate, with tetrakis(triphenylphosphine)palladium or palladium acetate being preferable. The amount of palladium used as catalyst based on 1 mole of Compound (5) is normally 0.0001 time to 1 time the molar amount, and preferably 0.005 times to 0.3 times the molar amount of Compound (5).

In the case of using tris(dibenzylideneacetone)dipalladium, palladium chloride or palladium acetate for the catalyst, it is preferable that an organic phosphine compound also be present. Examples of organic phosphine compounds used include tri-n-butylphosphine, tri-tert-butylphosphine, tricyclohexylphosphine, butyldi-1-adamantylphosphine, triphenylphosphine, tri(o-tolyl)phosphine, 2-dicyclohexylphosphino-2',6'-dimethoxybiphenyl, 1,1'-bis(diphenylphosphino)ferrocene and 1,2,3,4,5-pentaphenyl-1'-(di-tert-butylphosphino)ferrocene, with tricyclohexylphosphine, butyldi-1-adamantylphosphine, triphenylphosphine or 2-dicyclohexylphosphino-2',6'-dimethoxybiphenyl being preferable. The amount of organic phosphine compound used based on 1 mole of palladium is normally 1 time to 5 times the molar amount, and preferably 1.5 times to 2.5 times the molar amount of palladium.

Examples of base or fluoride include alkali metal acetates such as sodium acetate or potassium acetate, alkali metal carbonates such as sodium carbonate, potassium carbonate or cesium carbonate, alkali metal phosphates such as trisodium phosphate or tripotassium phosphate, alkali metal hydroxides such as lithium hydroxide, sodium hydroxide or potassium hydroxide, quaternary ammonium hydroxides such as tetramethylammonium hydroxide, tetraethylammonium hydroxide or tetrabutylammonium hydroxide, and fluorides such as cesium fluoride, tetramethylammonium fluoride, tetraethylammonium fluoride or tetrabutylammonium fluoride, with sodium carbonate or tripotassium phosphate being preferable. The amount of base or fluoride used based on 1 mole of Compound (5) is normally 1 time to 10 times the molar amount, and preferably 1.5 times to 5 times the molar amount of Compound (5).

Although variable according to such factors as the types and amounts used of the raw materials, solvent and the like, the reaction temperature is normally 0° C. to 200° C. and preferably 50° C. to 150° C.

Although variable according to such factors as the reaction temperature, the reaction time is normally 10 minutes to 120 hours and preferably 0.5 hours to 48 hours.

Although the reaction pressure may be suitably set as necessary and the reaction may be carried out under increased pressure, reduced pressure or atmospheric pressure, the reaction pressure is preferably atmospheric pressure.

Step 6 of Synthesis 3 is a step for obtaining Compound (1) by subjecting Compound (9) to deprotection to remove protecting group PG from Compound (9).

Deprotection conditions can be suitably selected according to a method described in the known art, such as the aforementioned Protective Groups in Organic Synthesis, 4th Edition, T. W. Greene and P. G. M. Wuts, ed., John Wiley & Sons Inc., or Examples of the present description.

Furthermore, in the case Compound (9) has a protecting group other than protecting group PG, preferably only protecting group PG is removed by suitably selecting the deprotection conditions.

Compound (1) used in Production Method 1 is obtained according to the aforementioned Syntheses 1 to 3. However, Compound (1) used in the Production Method 1 can also be obtained by a reaction scheme other than that indicated in the aforementioned Syntheses 1 to 3, by interchanging the suitable combinations and/or suitable reaction orders of each of the steps and raw materials indicated in the aforementioned Syntheses 1 to 3 and by introducing and/or removing suitable protecting groups.

Although the compound obtained in each step may be isolated and purified by known means, the compound may also be used in the subsequent step as it is. Isolation and purification can be carried out using ordinary procedures such as filtration, extraction, crystallization and various column chromatography techniques.

In a specific embodiment, the present invention relates to a pharmaceutical composition containing the compound of general formula (I) described in any of the aforementioned specific embodiments, or a pharmacologically acceptable salt thereof, and preferably relates to a pharmaceutical composition containing the compound of general formula (I) described in any of the aforementioned specific embodiments, or a pharmacologically acceptable salt thereof, and at least one type of pharmacologically acceptable additive.

In a specific embodiment, the present invention relates to a pharmaceutical composition containing the compound of general formula (I) described in any of the aforementioned specific embodiments, or a pharmacologically acceptable salt thereof, for treating a disease prevented, alleviated and/or treated by inhibiting VAP-1, and preferably relates to a pharmaceutical composition containing the compound of general formula (I) described in any of the aforementioned specific embodiments, or a pharmacologically acceptable salt thereof, and at least one type of pharmacologically acceptable additive, for treating a disease prevented, alleviated and/or treated by inhibiting VAP-1.

In a specific embodiment, the present invention relates to a pharmaceutical composition containing the compound of general formula (I) described in any of the aforementioned specific embodiments, or a pharmacologically acceptable salt thereof, for treating diabetic nephropathy, and preferably relates to a pharmaceutical composition containing the compound of general formula (I) described in any of the aforementioned specific embodiments, or a pharmacologically acceptable salt thereof, and at least one type of pharmacologically acceptable additive, for treating diabetic nephropathy.

In a specific embodiment, the present invention relates to a pharmaceutical composition containing the compound of general formula (I) described in any of the aforementioned specific embodiments, or a pharmacologically acceptable salt thereof, for treating non-alcoholic steatohepatitis, and preferably relates to a pharmaceutical composition containing the compound of general formula (I) described in any of the aforementioned specific embodiments, or a pharmacologically acceptable salt thereof, and at least one type of pharmacologically acceptable additive, for treating non-alcoholic steatohepatitis.

The pharmaceutical composition containing the compound of general formula (I), or a pharmaceutically acceptable salt thereof, can be in the form of the compound per se (in the form of a bulk powder), or can be in the form of a preparation, such as a tablet, capsule, powder, syrup, granule, grain, pill, suspension, emulsion, percutaneous agent, suppository, ointment, lotion, inhalant, ophthalmic solution or injection, produced by mixing with suitable pharmacologically acceptable additives and the like, and can be administered orally or parenterally (such as by intravenous, intramuscular, intraperitoneal, transdermal, transnasal, transtracheal, transpulmonary, ophthalmic, intradermal or subcutaneous administration).

These preparations are produced by known methods using additives such as excipients, lubricants, binders, disintegrating agents, emulsifiers, stabilizers, correctives, diluents, isotonic agents, buffers, pH adjusters, solubilizers, thickeners, dispersants or preservatives (antiseptics).

Examples of excipients include organic excipients and inorganic excipients. Examples of organic excipients include sugar derivatives such as lactose, sucrose, glucose, mannitol or sorbitol, starch derivatives such as cornstarch, potato starch, α-starch or dextrin, cellulose derivatives such as crystalline cellulose, gum arabic, dextran and pullulan. Examples of inorganic excipients include light anhydrous silicic acid, and sulfates such as calcium sulfate.

Examples of lubricants include stearic acid, metal stearates such as calcium stearate or magnesium stearate, talc, colloidal silica, waxes such as beeswax or spermaceti, boric acid, adipic acid, sulfates such as sodium sulfate, glycol, fumaric acid, sodium benzoate, D,L-leucine, sodium lauryl sulfate, silicic acids such as anhydrous silicic acid or silicic acid hydrate, and starch derivatives listed as examples of the aforementioned excipients.

Examples of binders include hydroxypropyl cellulose, hydroxypropyl methyl cellulose, polyvinylpyrrolidone, macrogol, and compounds listed as examples of the aforementioned excipients.

Examples of disintegrating agents include cellulose derivatives such as low substituted hydroxypropyl cellulose, carboxymethyl cellulose, calcium carboxymethyl cellulose or internally crosslinked calcium carboxymethyl cellulose, crosslinked polyvinylpyrrolidone, and chemically modified starch or cellulose derivatives such as carboxymethyl starch or sodium carboxymethyl starch.

Examples of emulsifiers include colloidal clay such as bentonite or Veegum, anionic surfactants such as sodium lauryl sulfate, cationic surfactants such as benzalkonium chloride, and nonionic surfactants such as polyoxyethylene alkyl ether, polyoxyethylene sorbitan fatty acid ester or sucrose fatty acid ester.

Examples of stabilizers include parahydroxybenzoates such as methyl paraben or propyl paraben, alcohols such as chlorobutanol, benzyl alcohol or phenyl ethyl alcohol, benzalkonium chloride, phenols such as phenol or cresol, thimerosal, acetic anhydride and sorbic acid.

Examples of correctives include sweeteners such as sodium saccharin or aspartame, acidifiers such as citric acid, malic acid or tartaric acid, and aromatics such as menthol, lemon extract or orange extract.

Examples of diluents include usual diluting compounds such as water, lactose, mannitol, glucose, sucrose, calcium sulfate, hydroxypropyl cellulose, microcrystalline cellulose, water, ethanol, polyethylene glycol, propylene glycol, glycerol, starch, polyvinylpyrrolidone and mixtures thereof.

Examples of isotonic agents include glycerin, propylene glycol, sodium chloride, potassium chloride, sorbitol and mannitol.

Examples of buffers include phosphoric acid, phosphates, citric acid, acetic acid and ε-aminocaproic acid.

Examples of pH adjusters include hydrochloric acid, citric acid, phosphoric acid, acetic acid, sodium hydroxide, potassium hydroxide, boric acid, borax, sodium carbonate and sodium bicarbonate.

Examples of solubilizers include Polysorbate 80, polyoxyethylene hydrogenated castor oil 60 and macrogol 4000.

Examples of thickeners and dispersants include cellulose polymers such as hydroxypropyl methyl cellulose or hydroxypropyl cellulose, polyvinyl alcohol and polyvinylpyrrolidone. Examples of stabilizers include edetic acid and sodium edetate.

Examples of preservatives (antiseptics) include general purpose sorbic acid, potassium sorbate, benzalkonium chloride, benzethonium chloride, methyl parahydroxybenzoate, propyl parahydroxybenzoate and chlorobutanol, and these preservatives can also be used in combination.

Other suitable additives can also be used corresponding to the administration form. For example, in the case the compound of general formula (I) of the present invention, or a pharmacologically acceptable salt thereof, is in the form of an aerosol for transnasal or transtracheal administration, carbon dioxide or a chlorofluorocarbon (CFC), such as dichlorodifluoromethane, trichlorofluoromethane or dichlorotetrafluoroethane, can be used for the propellant.

Although variable according to conditions such as the symptoms, age or body weight of a patient, the dosage of the active ingredient of the pharmaceutical composition of the present invention is 0.001 mg/Kg (and preferably 0.01 mg/Kg) as the lower limit and 20 mg/Kg (and preferably 10 mg/Kg) as the upper limit each per administration in the case of oral administration, or is 0.0001 mg/Kg (and preferably 0.0005 mg/Kg) as the lower limit and 10 mg/Kg (and preferably 5 mg/Kg) as the upper limit each per administration in the case of parental administration, administered one to six times per day to an adult corresponding to symptoms.

In a specific embodiment, the present invention relates to the compound of general formula (I) described in any of the aforementioned specific embodiments, or a pharmacologically acceptable salt thereof, for use in treating a disease prevented, alleviated and/or treated by inhibiting VAP-1.

In a specific embodiment, the present invention relates to the use of the compound of general formula (I) described in any of the aforementioned specific embodiments, or a pharmacologically acceptable salt thereof, for producing a medicament for treating a disease prevented, alleviated and/or treated by inhibiting VAP-1.

In a specific embodiment, the present invention relates to a method for treating a disease prevented, alleviated and/or treated by inhibiting VAP-1, which includes administering a therapeutically effective amount of the compound of general formula (I) described in any of the aforementioned specific embodiments, or a pharmacologically acceptable salt thereof, to a patient in need thereof.

In the present invention, the terms "treating" a disease or "treatment" of a disease include (1) preventing a disease, or in other words, not allowing the onset of clinical symptoms of a disease in a subject which, although there is the possibility of having been exposed to the disease or been susceptible to the disease, does not yet have or exhibit symptoms of the disease, (2) suppressing a disease, or in other words, suppressing the onset of a disease or clinical symptoms thereof, or (3) alleviating a disease, or in other words, inducing a temporary or permanent regression of the disease or clinical symptoms thereof.

In the present invention, a "therapeutically effective amount" refers to, in the case of administering to a subject, an amount of the compound of general formula (I) of the present invention that (i) treats or prevents a disease, (ii) relieves, improves or eliminates one or more symptoms of a disease, or (iii) prevents or delays the manifestation of one or more symptoms of a disease. The therapeutically effective amount varies according to the type of the compound of general formula (I) of the present invention used, the clinical condition of the disease being treated, the severity of the disease being treated, the age and relative health status of the subject, the administration route and form, the discretion of the examining physician or veterinarian, and other factors.

EXAMPLES

DIOL silica gel in silica gel column chromatography indicates CHROMATOREX (trade name) DIOL MB 100-40/75 manufactured by Fuji Silysia Chemical Ltd.

Unless otherwise mentioned, $^1$H-NMR is indicated by chemical shifts (δ) relative to tetramethylsilane as the internal standard (0 ppm), and the coupling constants (J values) are indicated in Hz unit. The peak splitting patterns are indicated by the following abbreviations: s: singlet, d: doublet, t: triplet, q: quartet, sext: sextet, sep: septet, br s: broad singlet, m: multiplet.

The abbreviations described in Examples and Reference Examples have general meanings that are usually used in the fields of organic chemistry and pharmaceuticals. Specifically, the abbreviations are understood by skilled artisans as follows.

DMF: N,N-dimethylformamide
DMSO: dimethylsulfoxide
THF: tetrahydrofuran
CDI: 1,1'-carbonyldiimidazole
NMP: N-methylpyrrolidone Example 1

2-Fluoro-3-[5-fluoro-6-(3-methoxyazetidin-1-yl)pyridin-3-yl]benzyl carbamimidoylcarbamate (Compound I-1)

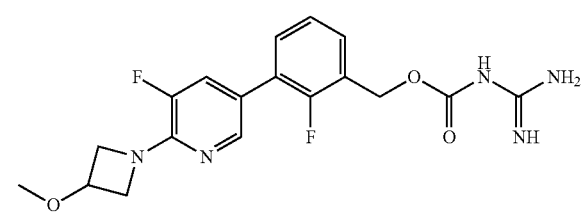 [SMILES: COC1CN(c2ncc(-c3cccc(COC(=O)NC(=N)N)c3F)cc2F)C1]

CDI 300 mg (1.85 mmol) was added to a DMF (6 mL) solution of {2-fluoro-3-[5-fluoro-6-(3-methoxyazetidin-1-yl)pyridin-3-yl-]phenyl}methanol 280 mg (0.914 mmol) synthesized in the same manner as in Reference Example 6-1, and the mixture was stirred at room temperature for 4 hours. Next, guanidine carbonate 331 mg (1.84 mmol) was added, and the mixture was stirred at room temperature for 16 hours. After the completion of the reaction, water was added to the reaction mixture, and the mixture was stirred at room temperature. The precipitated solid was collected by filtration. Ethyl acetate was added to the solid, and the mixture was stirred at 60° C. The solid was then collected by filtration and dried under reduced pressure to give the title compound 262 mg (0.669 mmol, yield 73%) as a white solid.

Mass spectrum (ESI, m/z): 392[M+1]$^+$.
$^1$H-NMR spectrum (400 MHz, DMSO-d$_6$+D$_2$O) δ:8.14-8.09 (m, 1H), 7.71-7.62 (m, 1H), 7.53-7.44 (m, 1H), 7.42-7.35 (m, 1H), 7.30-7.23 (m, 1H), 5.05 (s, 2H), 4.43-4.20 (m, 3H), 4.00-3.87 (m, 2H), 3.26 (s, 3H).

Example 2

2-Fluoro-3-{5-fluoro-6-[3-(methoxy-d$_3$)azetidin-1-yl]pyridin-3-yl}benzyl carbamimidoylcarbamate (Compound I-2)

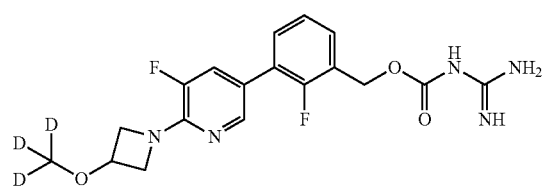 [SMILES: [2H]C([2H])([2H])OC1CN(c2ncc(-c3cccc(COC(=O)NC(=N)N)c3F)cc2F)C1]

CDI 330 mg (2.04 mmol) was added to a DMF (6 mL) solution of (2-fluoro-3-{5-fluoro-6-[3-(methoxy-d$_3$)azetidin-1-yl]pyridin-3-yl}phenyl)methanol 308 mg (0.996 mmol) synthesized in the same manner as in Reference Example 6-2, and the mixture was stirred at room temperature for 3 hours. Next, guanidine carbonate 368 mg (2.04 mmol) was added, and the mixture was stirred at room temperature for 20 hours. After the completion of the reaction, water was added to the reaction mixture, and the mixture was stirred at room temperature. The precipitated solid was collected by filtration and dried under reduced pressure to give the title compound 326 mg (0.827 mmol, yield 83%) as a white solid.

Mass spectrum (ESI, m/z): 395[M+1]⁺.

¹H-NMR spectrum (400 MHz, DMSO-d$_6$+D$_2$O) δ:8.15-8.09 (m, 1H), 7.70-7.61 (m, 1H), 7.51-7.44 (m, 1H), 7.42-7.35 (m, 1H), 7.30-7.24 (m, 1H), 5.05 (s, 2H), 4.37-4.29 (m, 3H), 3.97-3.90 (m, 2H).

Example 3

3-[6-(3-Ethoxyazetidin-1-yl)-5-fluoropyridin-3-yl]-2-fluorobenzyl carbamimidoylcarbamate (Compound I-3)

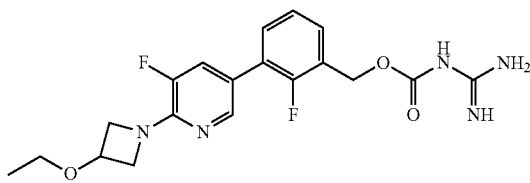 [SMILES: CCOC1CN(c2ncc(-c3cccc(COC(=O)NC(=N)N)c3F)cc2F)C1]

CDI 335 mg (2.07 mmol) was added to a DMF (6 mL) solution of {3-[6-(3-ethoxyazetidin-1-yl)-5-fluoropyridin-3-yl]-2-fluorophenyl}methanol 328 mg (1.02 mmol) synthesized in the same manner as in Reference Example 6-3, and the mixture was stirred at room temperature for 5 hours. Next, guanidine carbonate 369 mg (2.05 mmol) was added, and the mixture was stirred at room temperature for 27 hours. After the completion of the reaction, water was added to the reaction mixture, and the mixture was stirred at room temperature. The precipitated solid was collected by filtration and dried under reduced pressure to give the title compound 375 mg (0.925 mmol, yield 90%) as a white solid.

Mass spectrum (ESI, m/z): 406[M+1]⁺.

¹H-NMR spectrum (400 MHz, DMSO-d$_6$+D$_2$O) δ:8.13-8.09 (m, 1H), 7.70-7.62 (m, 1H), 7.51-7.44 (m, 1H), 7.42-7.36 (m, 1H), 7.31-7.23 (m, 1H), 5.06 (s, 2H), 4.50-4.40 (m, 1H), 4.37-4.29 (m, 2H), 3.98-3.89 (m, 2H), 3.46 (q, J=7.0 Hz, 2H), 1.15 (t, J=7.0 Hz, 3H).

Example 4

2-Fluoro-3-{5-fluoro-6-[3-(2-fluoroethoxy)azetidin-1-yl]pyridin-3-yl}benzyl carbamimidoylcarbamate (Compound I-4)

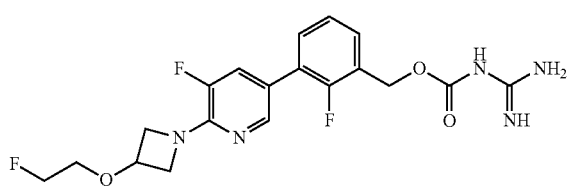 [SMILES: N=C(N)NC(=O)OCc1cccc(-c2cnc(N3CC(OCCF)C3)c(F)c2)c1F]

CDI 150 mg (0.925 mmol) was added to a DMF (8 mL) solution of (2-fluoro-3-{5-fluoro-6-[3-(2-fluoroethoxy)azetidin-1-yl]pyridin-3-yl}phenyl)methanol 156 mg (0.461 mmol) synthesized in the same manner as in Reference Example 6-4, and the mixture was stirred at room temperature for 2 hours. Next, guanidine carbonate 166 mg (0.921 mmol) was added, and the mixture was stirred at room temperature for 20 hours. After the completion of the reaction, water was added to the reaction mixture, and the mixture was stirred at room temperature. The precipitated solid was collected by filtration and dried under reduced pressure to give the title compound 170 mg (0.402 mmol, yield 87%) as a white solid.

Mass spectrum (ESI, m/z): 424[M+1]⁺.

¹H-NMR spectrum (400 MHz, DMSO-d$_6$+D$_2$O) δ:8.14-8.10 (m, 1H), 7.71-7.63 (m, 1H), 7.52-7.44 (m, 1H), 7.42-7.35 (m, 1H), 7.31-7.23 (m, 1H), 5.05 (s, 2H), 4.65-4.59 (m, 1H), 4.54-4.47 (m, 2H), 4.39-4.30 (m, 2H), 4.01-3.91 (m, 2H), 3.76-3.61 (m, 2H).

Example 5

2-Fluoro-3-[5-fluoro-6-(3-propoxyazetidin-1-yl)pyridin-3-yl]benzyl carbamimidoylcarbamate (Compound I-5)

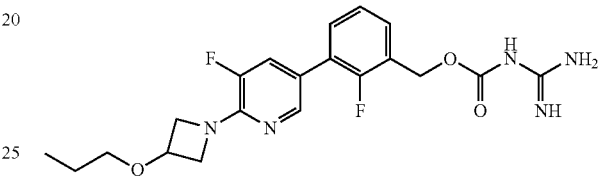

CDI 181 mg (1.12 mmol) was added to a DMF (6 mL) solution of {2-fluoro-3-[5-fluoro-6-(3-propoxyazetidin-1-yl)pyridin-3-yl]phenyl}methanol 187 mg (0.559 mmol) synthesized in the same manner as in Reference Example 6-5, and the mixture was stirred at room temperature for 3 hours. Next, guanidine carbonate 202 mg (1.12 mmol) was added, and the mixture was stirred at room temperature for 16 hours. After the completion of the reaction, water was added to the reaction mixture, and the mixture was stirred at room temperature. The precipitated solid was collected by filtration and dried under reduced pressure to give the title compound 197 mg (0.470 mmol, yield 84%) as a white solid.

Mass spectrum (ESI, m/z): 420[M+1]⁺.

¹H-NMR spectrum (400 MHz, DMSO-d$_6$+D$_2$O) δ:8.13-8.09 (m, 1H), 7.71-7.62 (m, 1H), 7.52-7.44 (m, 1H), 7.43-7.35 (m, 1H), 7.31-7.23 (m, 1H), 5.06 (s, 2H), 4.47-4.41 (m, 1H), 4.36-4.30 (m, 2H), 3.95-3.90 (m, 2H), 3.36 (t, J=6.6 Hz, 2H), 1.59-1.48 (m, 2H), 0.89 (t, J=7.4 Hz, 3H).

Example 6

2-Fluoro-3-[5-fluoro-6-(3-isopropoxyazetidin-1-yl)pyridin-3-yl]benzyl carbamimidoylcarbamate (Compound I-6)

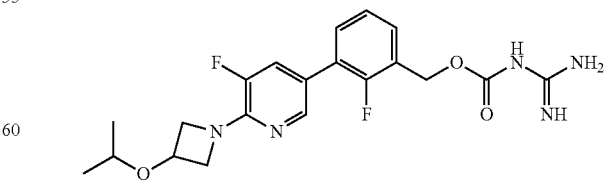

CDI 518 mg (3.19 mmol) was added to a DMF (8 mL) solution of {2-fluoro-3-[5-fluoro-6-(3-isopropoxyazetidin-1-yl)pyridin-3-yl]phenyl}methanol 534 mg (1.60 mmol) synthesized in the same manner as in Reference 6-6, and the mixture was stirred at room temperature for 2 hours. Next, guanidine 573 mg (3.18 mmol) carbonate was added, and the mixture was stirred at room temperature for 21 hours. After the completion of the reaction, water was added to the reaction mixture, and the mixture was stirred at room temperature. The precipitated solid was collected by filtration and dried under reduced pressure to give the title compound 524 mg (1.25 mmol, yield 78%) as a white solid.

Mass spectrum (ESI, m/z): 420[M+1]$^+$.

$^1$H-NMR spectrum (400 MHz, DMSO-d$_6$+D$_2$O) δ:8.14-8.09 (m, 1H), 7.69-7.63 (m, 1H), 7.52-7.44 (m, 1H), 7.42-7.36 (m, 1H), 7.31-7.22 (m, 1H), 5.06 (s, 2H), 4.56-4.50 (m, 1H), 4.38-4.32 (m, 2H), 3.93-3.87 (m, 2H), 3.71-3.61 (m, 1H), 1.12 (d, J=6.1 Hz, 6H).

Example 7

2-Fluoro-3-(5-fluoro-6-{3-[(tetrahydropyran-2-yl)oxy]azetidin-1-yl}pyridin-3-yl)benzyl carbamimidoylcarbamate (Compound I-40)

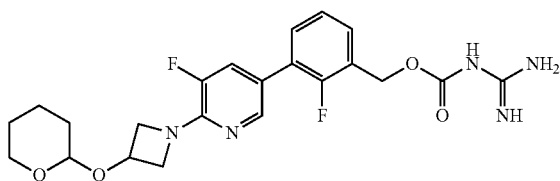 [SMILES: N=C(N)NC(=O)OCc1cccc(-c2cnc(N3CC(OC4CCCCO4)C3)c(F)c2)c1F]

CDI 330 mg (2.04 mmol) was added to a DMF (4 mL) solution of [2-fluoro-3-(5-fluoro-6-{3-[(tetrahydropyran-2-yl)oxy]azetidin-1-yl}pyridin-3-yl)phenyl]methanol 340 mg (0.903 mmol) synthesized in the same manner as in Reference Example 6-7, and the mixture was stirred at room temperature for 1 hour. Next, guanidine carbonate 330 mg (1.83 mmol) was added, and the mixture was stirred at room temperature for 16 hours. After the completion of the reaction, water was added to the reaction mixture, and the mixture was stirred at room temperature. The precipitated solid was collected by filtration. Toluene was added to the solid, and the mixture was concentrated under reduced pressure and dried under reduced pressure to give the title compound 317 mg (0.687 mmol, yield 76%) as a white solid.

$^1$H-NMR spectrum (400 MHz, DMSO-d$_6$+D$_2$O) δ:8.15-8.09 (m, 1H), 7.71-7.62 (m, 1H), 7.52-7.45 (m, 1H), 7.43-7.35 (m, 1H), 7.32-7.23 (m, 1H), 5.06 (s, 2H), 4.71-4.63 (m, 2H), 4.40-4.29 (m, 2H), 4.03-3.96 (m, 2H), 3.86-3.74 (m, 1H), 3.49-3.43 (m, 1H), 1.85-1.39 (m, 6H).

Example 8

2-Fluoro-3-[5-fluoro-6-(3-hydroxyazetidin-1-yl)pyridin-3-yl]benzyl carbamimidoylcarbamate (Compound I-12)

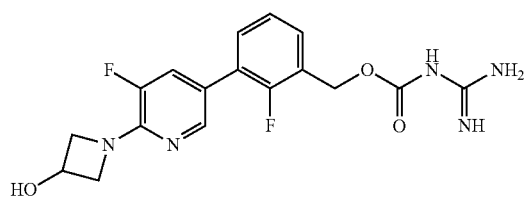 [SMILES: N=C(N)NC(=O)OCc1cccc(-c2cnc(N3CC(O)C3)c(F)c2)c1F]

2 N HCl/ethanol 1.40 mL (2.80 mmol) was added to an ethanol (6 mL) suspension of 2-fluoro-3-(5-fluoro-6-{3-[(tetrahydropyran-2-yl)oxy]azetidin-1-yl}pyridin-3-yl)benzyl carbamimidoylcarbamate 317 mg (0.687 mmol) synthesized in the same manner as in Example 7, and the mixture was stirred at room temperature for 30 minutes. After the completion of the reaction, triethylamine 0.400 mL (2.87 mmol) was added, and the mixture was concentrated under reduced pressure. The concentrated residue was purified by silica gel column chromatography (eluting solvent; dichloroethane:methanol). The fraction including the title compound was concentrated under reduced pressure. Ethyl acetate was added to the concentrated residue, and the mixture was stirred at room temperature. The precipitated solid was collected by filtration and dried under reduced pressure to give the title compound 187 mg (0.496 mmol, yield 72%) as a white solid.

Mass spectrum (ESI, m/z): 378[M+1]$^+$.

$^1$H-NMR spectrum (400 MHz, DMSO-d$_6$+D$_2$O) δ:8.13-8.09 (m, 1H), 7.70-7.61 (m, 1H), 7.53-7.44 (m, 1H), 7.43-7.35 (m, 1H), 7.31-7.23 (m, 1H), 5.06 (s, 2H), 4.64-4.57 (m, 1H), 4.36-4.28 (m, 2H), 3.92-3.83 (m, 2H).

Example 9

3-[6-(Azetidin-1-yl)-5-fluoropyridin-3-yl]-2-fluorobenzyl carbamimidoylcarbamate (Compound I-13)

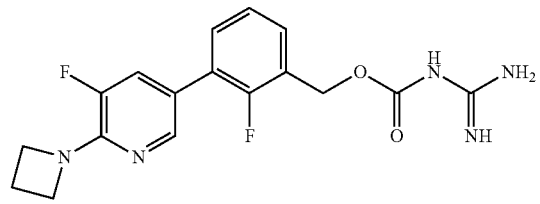 [SMILES: N=C(N)NC(=O)OCc1cccc(-c2cnc(N3CCC3)c(F)c2)c1F]

CDI 302 mg (1.86 mmol) was added to a DMF (6 mL) solution of {3-[6-(azetidin-1-yl)-5-fluoropyridin-3-yl]-2-fluorophenyl}methanol 257 mg (0.930 mmol) synthesized in the same manner as in Reference Example 6-8, and the mixture was stirred at room temperature for 2 hours. Next, guanidine carbonate 335 mg (1.86 mmol) was added, and the mixture was stirred at room temperature for 20 hours. After the completion of the reaction, water was added to the reaction mixture, and the mixture was stirred at room temperature. The precipitated solid was collected by filtration and dried under reduced pressure to give the title compound 306 mg (0.847 mmol, yield 91%) as a white solid.

Mass spectrum (ESI, m/z): 362[M+1]$^+$.

$^1$H-NMR spectrum (400 MHz, DMSO-d$_6$+D$_2$O) δ:8.12-8.08 (m, 1H), 7.67-7.59 (m, 1H), 7.52-7.44 (m, 1H), 7.42-7.34 (m, 1H), 7.30-7.21 (m, 1H), 5.05 (s, 2H), 4.20-4.01 (m, 4H), 2.45-2.24 (m, 2H).

Example 10

2-Fluoro-3-[5-fluoro-6-(3-fluoroazetidin-1-yl)pyridin-3-yl]benzyl carbamimidoylcarbamate (Compound I-14)

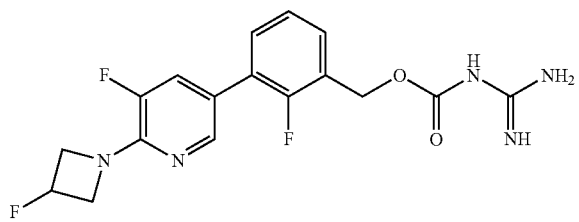 [SMILES: N=C(N)NC(=O)OCc1cccc(-c2cnc(N3CC(F)C3)c(F)c2)c1F]

CDI 180 mg (1.11 mmol) was added to a DMF (6 mL) solution of {2-fluoro-3-[5-fluoro-6-(3-fluoroazetidin-1-yl)pyridin-3-yl]phenyl}methanol 158 mg (0.537 mmol) synthesized in the same manner as in Reference Example 6-9, and the mixture was stirred at room temperature for 2 hours. Next, guanidine carbonate 201 mg (1.12 mmol) was added, and the mixture was stirred at room temperature for 20 hours. After the completion of the reaction, water was added to the reaction mixture, and the mixture was stirred at room temperature. The precipitated solid was collected by filtration and dried under reduced pressure to give the title compound 182 mg (0.480 mmol, yield 89%) as a white solid.

Mass spectrum (ESI, m/z): 380[M+1]$^+$.

$^1$H-NMR spectrum (400 MHz, DMSO-d$_6$+D$_2$O) δ:8.18-8.12 (m, 1H), 7.76-7.66 (m, 1H), 7.53-7.45 (m, 1H), 7.43-7.36 (m, 1H), 7.31-7.24 (m, 1H), 5.69-5.36 (m, 1H), 5.06 (s, 2H), 4.55-4.36 (m, 2H), 4.26-4.09 (m, 2H).

Example 11

3-[6-(3,3-Difluoroazetidin-1-yl)-5-fluoropyridin-3-yl]-2-fluorobenzyl carbamimidoylcarbamate (Compound I-18)

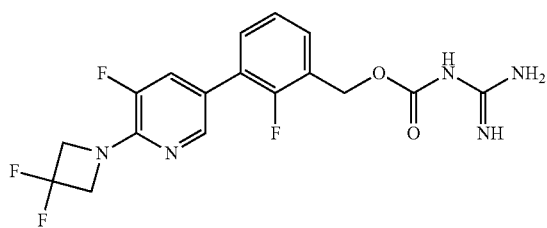 [SMILES: N=C(N)NC(=O)OCc1cccc(-c2cnc(N3CC(F)(F)C3)c(F)c2)c1F]

CDI 163 mg (1.01 mmol) was added to a DMF (6 mL) solution of (3-(6-(3,3-difluoroazetidin-1-yl)-5-fluoropyridin-3-yl)-2-fluorophenyl)methanol 157 mg (0.503 mmol) synthesized in the same manner as in Reference Example 6-10, and the mixture was stirred at room temperature for 2 hours. Next, guanidine carbonate 181 mg (1.01 mmol) was added, and the mixture was stirred at room temperature for 20 hours. After the completion of the reaction, water was added to the reaction mixture, and the mixture was stirred at room temperature. The precipitated solid was collected by filtration and dried under reduced pressure to give the title compound 143 mg (0.360 mmol, yield 72%) as a white solid.

Mass spectrum (ESI, m/z): 398[M+1]$^+$.

$^1$H-NMR spectrum (400 MHz, DMSO-d$_6$+D$_2$O) δ:8.23-8.15 (m, 1H), 7.81-7.75 (m, 1H), 7.54-7.46 (m, 1H), 7.45-7.37 (m, 1H), 7.32-7.25 (m, 1H), 5.06 (s, 2H), 4.66-4.43 (m, 4H).

Example 12

2-Fluoro-3-[5-fluoro-6-(3-methylazetidin-1-yl)pyridin-3-yl]benzyl carbamimidoylcarbamate (Compound I-20)

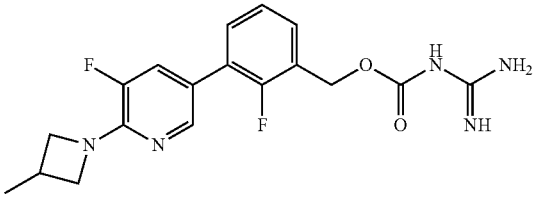 [SMILES: CC1CN(c2ncc(-c3cccc(COC(=O)NC(=N)N)c3F)cc2F)C1]

CDI 285 mg (1.76 mmol) was added to a DMF (6 mL) solution of {2-fluoro-3-[5-fluoro-6-(3-methylazetidin-1-yl)pyridin-3-yl]phenyl}methanol 255 mg (0.878 mmol) synthesized in the same manner as in Reference Example 6-11, and the mixture was stirred at room temperature for 2 hours. Next, guanidine carbonate 317 mg (1.76 mmol) was added, and the mixture was stirred at room temperature for 20 hours. After the completion of the reaction, water was added to the reaction mixture, and the mixture was stirred at room temperature. Next, methylene chloride was added, and the mixture was stirred at room temperature. The precipitated solid was collected by filtration and was dried under reduced pressure to give the title compound 272 mg (0.725 mmol, yield 82%) as a white solid.

Mass spectrum (ESI, m/z): 376[M+1]$^+$.

$^1$H-NMR spectrum (400 MHz, DMSO-d$_6$+D$_2$O) δ:8.12-8.07 (m, 1H), 7.66-7.58 (m, 1H), 7.51-7.34 (m, 1H), 7.41-7.34 (m, 1H), 7.29-7.21 (m, 1H), 5.05 (s, 2H), 4.34-4.15 (m, 2H), 3.81-3.63 (m, 2H), 2.88-2.78 (m, 1H), 1.25 (d, J=6.8 Hz, 3H).

Example 13

3-[6-(3,3-Dimethylazetidin-1-yl)-5-fluoropyridin-3-yl]-2-fluorobenzyl carbamimidoylcarbamate (Compound I-26)

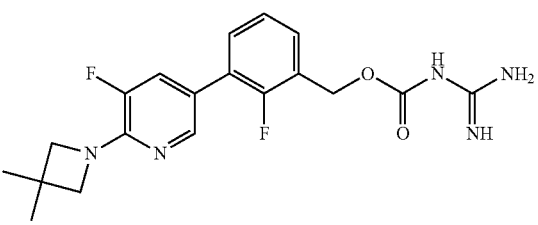 [SMILES: CC1(C)CN(c2ncc(-c3cccc(COC(=O)NC(=N)N)c3F)cc2F)C1]

CDI 279 mg (1.72 mmol) was added to a DMF (6 mL) solution of {3-[6-(3,3-dimethylazetidin-1-yl)-5-fluoropyridin-3-yl]-2-fluorophenyl}methanol 262 mg (0.861 mmol) synthesized in the same manner as in Reference Example 6-12, and the mixture was stirred at room temperature for 2 hours. Next, guanidine carbonate 310 mg (1.72 mmol) was added, and the mixture was stirred at room temperature for 20 hours. After the completion of the reaction, water was added to the reaction mixture and followed by extraction with methylene chloride. The organic layer was washed with water and dried over anhydrous sodium sulfate. The mixture was filtered and the filtrate was concentrated under reduced pressure. The concentrated residue was purified by silica gel column chromatography (DIOL silica gel, eluting solvent; hexane:ethyl acetate) to give the title compound 255 mg (0.655 mmol, yield 76%) as a white solid.

Mass spectrum (ESI, m/z): 390[M+1]$^+$.

$^1$H-NMR spectrum (400 MHz, DMSO-d$_6$+D$_2$O) δ:8.11-8.07 (m, 1H), 7.65-7.59 (m, 1H), 7.50-7.44 (m, 1H), 7.42-7.35 (m, 1H), 7.30-7.23 (m, 1H), 5.05 (s, 2H), 3.86-3.79 (m, 4H), 1.30 (s, 6H).

Example 14

2-Fluoro-3-(5-fluoro-6-{3-methyl-3-[(tetrahydropyran-2-yl)oxy]azetidin-1-yl}pyridin-3-yl)benzyl carbamimidoylcarbamate (Compound I-41)

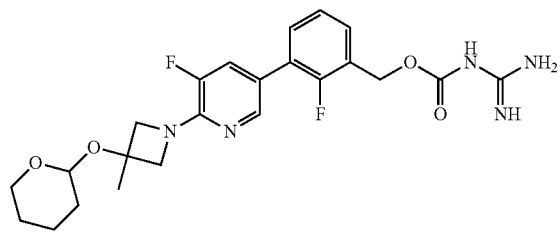 [SMILES: CC1(OC2CCCCO2)CN(c2ncc(-c3cccc(COC(=O)NC(=N)N)c3F)cc2F)C1]

CDI 281 mg (1.73 mmol) was added to a DMF (6 mL) solution of [2-fluoro-3-(5-fluoro-6-{3-methyl-3-[(tetrahydropyran-2-yl)oxy]azetidin-1-yl}pyridin-3-yl)phenyl] methanol 338 mg (0.866 mmol) synthesized in the same manner as in Reference Example 6-13, and the mixture was stirred at room temperature for 2 hours. Next, guanidine carbonate 313 mg (1.74 mmol) was added, and the mixture was stirred at room temperature for 20 hours. After the completion of the reaction, water was added to the reaction mixture, and the mixture was stirred at room temperature. The precipitated solid was collected by filtration and dried under reduced pressure to give the title compound 311 mg (0.654 mmol, yield 76%) as a white solid.

$^1$H-NMR spectrum (400 MHz, DMSO-d$_6$+D$_2$O) δ:8.15-8.08 (m, 1H), 7.72-7.63 (m, 1H), 7.52-7.44 (m, 1H), 7.43-7.35 (m, 1H), 7.31-7.23 (m, 1H), 5.12-5.01 (m, 2H), 4.90-4.81 (m, 1H), 4.22-4.08 (m, 2H), 4.05-3.92 (m, 2H), 3.89-3.79 (m, 1H), 3.60-3.45 (m, 1H), 1.90-1.35 (m, 9H).

Example 15

2-Fluoro-3-[5-fluoro-6-(3-hydroxy-3-methylazetidin-1-yl)pyridin-3-yl]benzyl carbamimidoylcarbamate (Compound I-30)

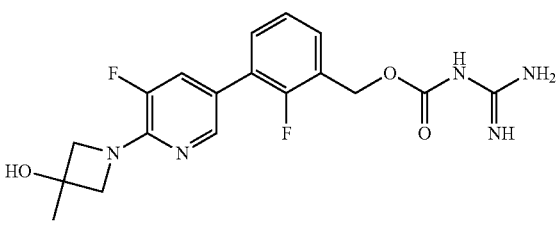 [SMILES: CC1(O)CN(c2ncc(-c3cccc(COC(=O)NC(=N)N)c3F)cc2F)C1]

At 0° C., 2 N HCl/ethanol 1.6 mL (3.20 mmol) was added to an ethanol (4 mL) suspension of 2-fluoro-3-(5-fluoro-6-{3-methyl-3-[(tetrahydropyran-2-yl)oxy]azetidin-1-yl}pyridin-3-yl)benzyl carbamimidoylcarbamate 311 mg (0.654 mmol) synthesized in the same manner as in Example 14, and the mixture was stirred at room temperature for 2 hours. After the completion of the reaction, triethylamine 0.55 mL (3.95 mmol) and water were added, and the mixture was stirred. The precipitated solid was collected by filtration and was dried under reduced pressure to give the title compound 211 mg (0.539 mmol, yield 82%) as a white solid.

Mass spectrum (ESI, m/z): 392[M+1]$^+$.

$^1$H-NMR spectrum (400 MHz, DMSO-d$_6$+D$_2$O) δ:8.13-8.08 (m, 1H), 7.69-7.61 (m, 1H), 7.51-7.44 (m, 1H), 7.42-7.35 (m, 1H), 7.29-7.22 (m, 1H), 5.06 (s, 2H), 4.09-3.85 (m, 4H), 1.47 (s, 3H).

Example 16

2-Fluoro-3-[5-fluoro-6-(2-oxa-6-azaspiro[3.3]heptan-6-yl)pyridin-3-yl]benzyl carbamimidoylcarbamate (Compound I-42)

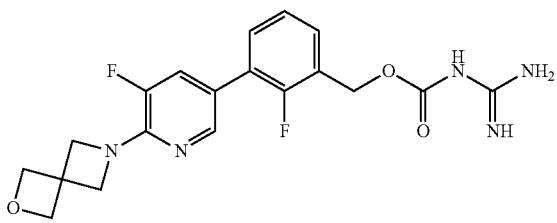 [SMILES: N=C(N)NC(=O)OCc1cccc(-c2cnc(N3CC4(COC4)C3)c(F)c2)c1F]

CDI 104 mg (0.641 mmol) was added to a DMF (6 mL) solution of {2-fluoro-3-[5-fluoro-6-(2-oxa-6-azaspiro[3.3] heptan-6-yl)pyridin-3-yl]phenyl}methanol 102 mg (0.320 mmol) synthesized in the same manner as in Reference Example 6-14, and the mixture was stirred at room temperature for 2 hours. Next, guanidine carbonate 115 mg (0.638 mmol) was added, and the mixture was stirred at room temperature for 20 hours. After the completion of the reaction, water was added to the reaction mixture, and the mixture was stirred at room temperature. The precipitated solid was collected by filtration and dried under reduced pressure to give the title compound 102 mg (0.253 mmol, yield 79%) as a white solid.

Mass spectrum (ESI, m/z): 404[M+1]$^+$.

¹H-NMR spectrum (400 MHz, DMSO-d₆+D₂O) δ:8.13-8.09 (m, 1H), 7.70-7.61 (m, 1H), 7.51-7.43 (m, 1H), 7.43-7.35 (m, 1H), 7.31-7.21 (m, 1H), 5.05 (s, 2H), 4.74 (s, 4H), 4.34-4.26 (m, 4H).

Reference Example 1

1-(5-Bromo-3-fluoropyridin-2-yl)azetidin-3-ol (Reference Compound 1)

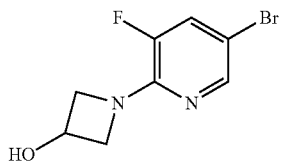

Triethylamine 14 mL (100 mol) was added to an ethanol (70 mL) solution of 5-bromo-2,3-difluoropyridine 7.56 g (39.0 mmol) and azetidin-3-ol hydrochloride 5.00 g (45.6 mol), and the mixture was stirred at 55° C. for 3 hours. After the completion of the reaction, water 70 mL was added to the reaction mixture. The mixture was concentrated under reduced pressure to approximately halve the solvent, and was thereafter stirred at room temperature. The precipitated solid was collected by filtration and was dried under reduced pressure to give the title compound 8.06 g (32.6 mol, yield 84%) as a white solid.

¹H-NMR spectrum (400 MHz, DMSO-d₆) δ:8.03-8.00 (m, 1H), 7.81-7.76 (m, 1H), 5.69 (d, J=6.4 Hz, 1H), 4.67-4.48 (m, 1H), 4.34-4.16 (m, 2H), 3.86-3.68 (m, 2H).

Reference Example 2-1

5-Bromo-3-fluoro-2-(3-methoxyazetidin-1-yl)pyridine (Reference Compound 2-1)

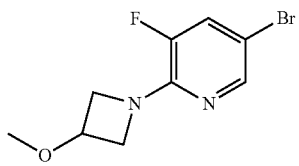

At 0° C., 55% sodium hydride 91 mg (2.09 mmol) was added in portions to a DMF (6 mL) solution of 1-(5-bromo-3-fluoropyridin-2-yl)azetidin-3-ol 300 mg (1.21 mmol) synthesized in the same manner as in Reference Example 1, and the mixture was stirred at 0° C. for 30 minutes. Next, iodomethane 0.15 mL (2.40 mmol) was added at 0° C., and the mixture was stirred at room temperature for 1 hour. After the completion of the reaction, saturated aqueous ammonium chloride solution was added to the reaction mixture, and followed by extraction with ethyl acetate. The organic layer was washed with water and dried over anhydrous sodium sulfate. The mixture was filtered and the filtrate was concentrated under reduced pressure. The concentrated residue was purified by silica gel column chromatography (eluting solvent; hexane:ethyl acetate) to give the title compound 297 mg (1.14 mmol, yield 94%) as a white solid.

¹H-NMR spectrum (400 MHz, DMSO-d₆) δ:8.04-7.99 (m, 1H), 7.83-7.76 (m, 1H), 4.45-4.12 (m, 3H), 3.95-3.77 (m, 2H), 3.24 (s, 3H).

Reference Example 2-2

5-Bromo-3-fluoro-2-[3-(methoxy-d₃)azetidin-1-yl]pyridine (Reference Compound 2-2)

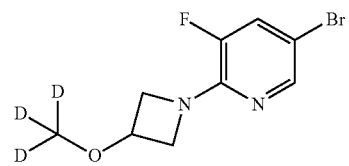 [SMILES: [2H]C([2H])([2H])OC1CN(c2ncc(Br)cc2F)C1]

The reaction was performed by the method described in Reference Example 2-1, except that iodomethane was replaced by iodomethane-d₃. Consequently, the title compound (yield 93%) was obtained as a white solid.

Mass spectrum (ESI, m/z): 264,266[M+1]⁺.

¹H-NMR spectrum (400 MHz, DMSO-d₆) δ:8.06-7.99 (m, 1H), 7.83-7.76 (m, 1H), 4.36-4.20 (m, 3H), 3.91-3.83 (m, 2H).

Reference Example 2-3

5-Bromo-2-(3-ethoxyazetidin-1-yl)-3-fluoropyridine (Reference Compound 2-3)

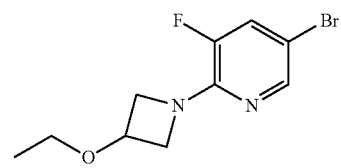

The reaction was performed by the method described in Reference Example 2-1, except that iodomethane was replaced by iodoethane. Consequently, the title compound (yield 91%) was obtained as a white solid.

Mass spectrum (ESI, m/z): 275,277[M+1]⁺.

¹H-NMR spectrum (400 MHz, DMSO-d₆) δ:8.03-8.01 (m, 1H), 7.82-7.77 (m, 1H), 4.45-4.35 (m, 1H), 4.30-4.21 (m, 2H), 3.91-3.81 (m, 2H), 3.44 (q, J=7.0 Hz, 2H), 1.13 (t, J=7.0 Hz, 3H).

Reference Example 2-4

5-Bromo-2-(3-ethoxyazetidin-1-yl)-3-fluoropyridine (Reference Compound 2-4)

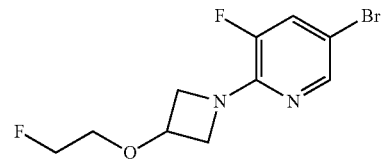 [SMILES: FCCOC1CN(c2ncc(Br)cc2F)C1]

The reaction was performed by the method described in Reference Example 2-1, except that iodomethane was replaced by 2-fluoroethyl methanesulfonate synthesized in the same manner as in Reference Example 7. Consequently, the title compound (yield 47%) was obtained as yellow oil.

Mass spectrum (ESI, m/z): 293,295[M+1]$^+$.

$^1$H-NMR spectrum (400 MHz, DMSO-d$_6$) δ:8.04-8.01 (m, 1H), 7.84-7.78 (m, 1H), 4.64-4.57 (m, 1H), 4.52-4.44 (m, 2H), 4.32-4.20 (m, 2H), 3.94-3.83 (m, 2H), 3.74-3.58 (m, 2H).

Reference Example 2-5

5-Bromo-3-fluoro-2-(3-propoxyazetidin-1-yl)pyridine (Reference Compound 2-5)

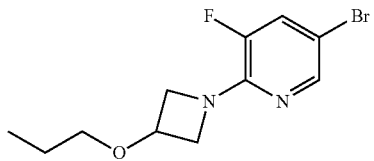 [SMILES: CCCOC1CN(c2ncc(Br)cc2F)C1]

The reaction was performed by the method described in Reference Example 2-1, except that iodomethane was replaced by iodopropane. Consequently, the title compound (yield 53%) was obtained as colorless oil.

Mass spectrum (ESI, m/z): 289,291[M+1]$^+$.

$^1$H-NMR spectrum (400 MHz, DMSO-d$_6$) δ:8.04-8.00 (m, 1H), 7.84-7.76 (m, 1H), 4.46-4.35 (m, 1H), 4.31-4.21 (m, 2H), 3.89-3.82 (m, 2H), 3.37-3.28 (m, 2H), 1.52 (sext, J=7.3 Hz, 2H), 0.88 (t, J=7.3 Hz, 3H).

Reference Example 3

[(3-Bromo-2-fluorobenzyl)oxy](tert-butyl)dimethylsilane (Reference Compound 3)

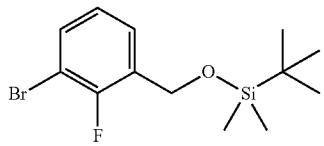 [SMILES: CC(C)(C)[Si](C)(C)OCc1cccc(Br)c1F]

(Tert-butyl)dimethylsilyl chloride 22 g (0.15 mol) and imidazole 14 g (0.21 mol) were added to a THF (200 mL) solution of (3-bromo-2-fluorophenyl)methanol 25 g (0.12 mol). The mixture was stirred at room temperature for 5 hours and was allowed to stand at room temperature for 2 days. After the completion of the reaction, water was added to the reaction mixture and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent; hexane:ethyl acetate) to give the title compound 35 g (0.11 mol, yield 92%) as colorless oil.

Mass spectrum (CI, m/z): 319,321[M+1]$^+$.

$^1$H-NMR spectrum (400 MHz, DMSO-d$_6$) δ: 7.65-7.59 (m, 1H), 7.48-7.42 (m, 1H), 7.22-7.15 (m, 1H), 4.78 (s, 2H), 0.90 (s, 9H), 0.09 (s, 6H).

Reference Example 4

Tert-butyl{[2-fluoro-3-(4,4,5,5-tetramethyl-1,3,2-dioxaborolan-2-yl)benzyl]oxy}dimethylsilane (Reference Compound 4)

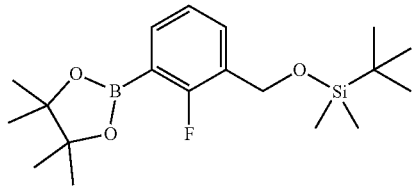 [SMILES: CC1(C)OB(c2cccc(CO[Si](C)(C)C(C)(C)C)c2F)OC1(C)C]

1,4-Dioxane (100 mL) solution of [(3-bromo-2-fluorobenzyl)oxy](tert-butyl)dimethylsilane 14.4 g (45.0 mmol) synthesized in the same manner as in Reference Example 3, bis(pinacolato)diborane 12.6 g (49.6 mmol) and potassium acetate 6.00 g (61.1 mmol) was degassed and purged with nitrogen. Next, [1,1'-bis(diphenylphosphino)ferrocene]palladium (II) dichloride 1.84 g (2.25 mmol) was added. Under a stream of argon, the mixture was stirred at 100° C. for 20 hours. After the completion of the reaction, the reaction mixture was filtered through Celite, water was added, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent; hexane: ethyl acetate) to give the title compound 9.64 g (26.3 mmol, yield 43%) as light yellow oil.

Mass spectrum (CI, m/z): 367[M+1]$^+$.

$^1$H-NMR spectrum (400 MHz, DMSO-d$_6$) δ: 7.60-7.52 (m, 2H), 7.25-7.17 (m, 1H), 4.74 (s, 2H), 1.29 (s, 12H), 0.90 (s, 9H), 0.09 (s, 6H).

Reference Example 5-1

5-(3-{[(Tert-butyldimethylsilyl)oxy]methyl}-2-fluorophenyl)-3-fluoro-2-(3-methoxyazetidin-1-yl)pyridine (Reference Compound 5-1)

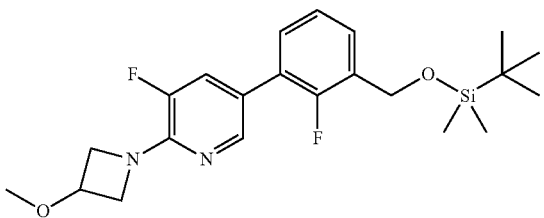 [SMILES: COC1CN(c2ncc(-c3cccc(CO[Si](C)(C)C(C)(C)C)c3F)cc2F)C1]

1,2-Dimethoxyethane (10 mL) suspension of 5-bromo-3-fluoro-2-(3-methoxyazetidin-1-yl)pyridine 297 mg (1.14 mmol) synthesized in the same manner as in Reference Example 2-1, tert-butyl{[2-fluoro-3-(4,4,5,5-tetramethyl-1,3,2-dioxaborolan-2-yl)benzyl]oxy}dimethylsilane 420 mg (1.15 mmol) synthesized in the same manner as in Reference Example 4 and 2 M aqueous sodium carbonate solution 1.45 mL (2.90 mmol) was degassed and purged with nitrogen. Next, tetrakis(triphenylphosphine)palladium (0) 131 mg (0.113 mmol) was added. Under a stream of argon, the mixture was stirred at 80° C. for 3 hours. After the completion of the reaction, water was added to the reaction mixture and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent; hexane:ethyl acetate) to give the title compound 399 mg (0.949 mmol, yield 83%) as yellow oil.

Mass spectrum (ESI, m/z): 421 [M+1]$^+$.

$^1$H-NMR spectrum (400 MHz, DMSO-d$_6$) δ:8.14-8.09 (m, 1H), 7.69-7.61 (m, 1H), 7.49-7.38 (m, 2H), 7.32-7.23 (m, 1H), 4.80 (s, 2H), 4.39-4.28 (m, 3H), 3.97-3.89 (m, 2H), 3.26 (s, 3H), 0.91 (s, 9H), 0.11 (s, 6H).

Reference Example 5-2

5-(3-{[(Tert-butyldimethylsilyl)oxy]methyl}-2-fluorophenyl)-3-fluoro-2-[3-(methoxy-d$_3$)azetidin-1-yl]pyridine (Reference Compound 5-2)

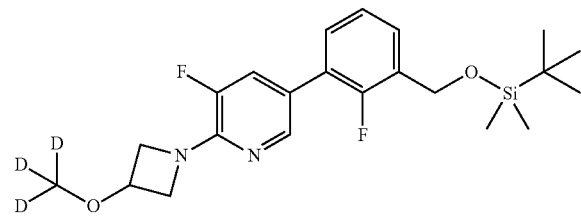 [SMILES: [2H]C([2H])([2H])OC1CN(c2ncc(-c3cccc(CO[Si](C)(C)C(C)(C)C)c3F)cc2F)C1]

1,4-Dioxane (15 mL)-water (7 mL) suspension of 5-bromo-3-fluoro-2-[3-(methoxy-d$_3$)azetidin-1-yl]pyridine 298 mg (1.13 mmol) synthesized in the same manner as in Reference Example 2-2, tert-butyl{[2-fluoro-3-(4,4,5,5-tetramethyl-1,3,2-dioxaborolan-2-yl)benzyl]oxy}dimethylsilane 480 mg (1.31 mmol) synthesized in the same manner as in Reference Example 4 and sodium carbonate 355 mg (3.35 mmol) was degassed and purged with nitrogen. Next, tetrakis(triphenylphosphine)palladium (0) 67 mg (0.058 mmol) was added. Under a stream of argon, the mixture was stirred at 80° C. for 4 hours. After the completion of the reaction, water was added to the reaction mixture and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent; hexane:ethyl acetate) to give the title compound 464 mg (1.10 mmol, yield 97%) as colorless oil.

Mass spectrum (ESI, m/z): 424[M+1]$^+$.

$^1$H-NMR spectrum (400 MHz, DMSO-d$_6$) δ:8.13-8.09 (m, 1H), 7.70-7.61 (m, 1H), 7.48-7.39 (m, 2H), 7.31-7.25 (m, 1H), 4.80 (s, 2H), 4.37-4.28 (m, 3H), 3.98-3.89 (m, 2H), 0.91 (s, 9H), 0.11 (s, 6H).

Reference Example 5-3

5-(3-{[(Tert-butyldimethylsilyl)oxy]methyl}-2-fluorophenyl)-2-(3-ethoxyazetidin-1-yl)-3-fluoropyridine (Reference Compound 5-3)

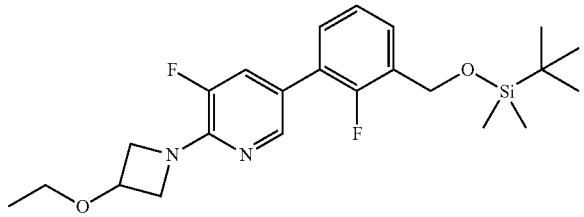 [SMILES: CCOC1CN(c2ncc(-c3cccc(CO[Si](C)(C)C(C)(C)C)c3F)cc2F)C1]

The reaction was performed by the method described in Reference Example 5-2, except that 5-bromo-3-fluoro-2-[3-(methoxy-d$_3$)azetidin-1-yl]pyridine was replaced by 5-bromo-2-(3-ethoxyazetidin-1-yl)-3-fluoropyridine synthesized in the same manner as in Reference Example 2-3. Consequently, the title compound (yield 98%) was obtained as colorless oil.

Mass spectrum (ESI, m/z): 435[M+1]$^+$.

$^1$H-NMR spectrum (400 MHz, DMSO-d$_6$) δ:8.13-8.09 (m, 1H), 7.69-7.61 (m, 1H), 7.50-7.39 (m, 2H), 7.32-7.24 (m, 1H), 4.80 (s, 2H), 4.48-4.39 (m, 1H), 4.37-4.28 (m, 2H), 3.98-3.87 (m, 2H), 3.46 (q, J=7.0 Hz, 2H), 1.15 (t, J=7.0 Hz, 3H), 0.91 (s, 9H), 0.11 (s, 6H).

Reference Example 5-4

5-(3-{[(Tert-butyldimethylsilyl)oxy]methyl}-2-fluorophenyl)-3-fluoro-2-[3-(2-fluoroethoxy)azetidin-1-yl]pyridine (Reference Compound 5-4)

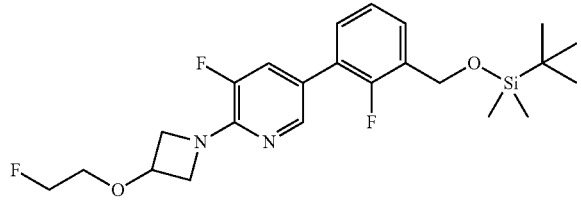 [SMILES: CC(C)(C)[Si](C)(C)OCc1cccc(-c2cnc(N3CC(OCCF)C3)c(F)c2)c1F]

The reaction was performed by the method described in Reference Example 5-2, except that 5-bromo-3-fluoro-2-[3-(methoxy-d$_3$)azetidin-1-yl]pyridine was replaced by 5-bromo-2-(3-ethoxyazetidin-1-yl)-3-fluoropyridine synthesized in the same manner as in Reference Example 2-4. Consequently, the title compound (yield 86%) was obtained as colorless oil.

Mass spectrum (ESI, m/z): 453[M+1]$^+$.

$^1$H-NMR spectrum (400 MHz, DMSO-d$_6$) δ:8.16-8.09 (m, 1H), 7.71-7.61 (m, 1H), 7.51-7.40 (m, 2H), 7.33-7.23 (m, 1H), 4.80 (s, 2H), 4.64-4.59 (m, 1H), 4.55-4.46 (m, 2H), 4.38-4.28 (m, 2H), 3.99-3.92 (m, 2H), 3.76-3.60 (m, 2H), 0.91 (s, 9H), 0.11 (s, 6H).

Reference Example 5-5

5-(3-{[(Tert-butyldimethylsilyl)oxy]methyl}-2-fluorophenyl)-3-fluoro-2-(3-propoxyazetidin-1-yl)pyridine (Reference Compound 5-5)

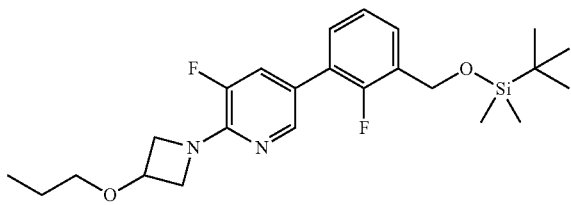 [SMILES: CCCOC1CN(c2ncc(-c3cccc(CO[Si](C)(C)C(C)(C)C)c3F)cc2F)C1]

The reaction was performed by the method described in Reference Example 5-2, except that 5-bromo-3-fluoro-2-[3-(methoxy-d₃)azetidin-1-yl]pyridine was replaced by 5-bromo-3-fluoro-2-(3-propoxyazetidin-1-yl)pyridine synthesized in the same manner as in Reference Example 2-5. Consequently, the title compound (yield 91%) was obtained as colorless oil.

Mass spectrum (ESI, m/z): 449[M+1]⁺.

¹H-NMR spectrum (400 MHz, DMSO-d₆) δ:8.14-8.09 (m, 1H), 7.69-7.61 (m, 1H), 7.47-7.40 (m, 2H), 7.32-7.24 (m, 1H), 4.80 (s, 2H), 4.47-4.38 (m, 1H), 4.36-4.27 (m, 2H), 3.97-3.86 (m, 2H), 3.39-3.28 (m, 2H), 1.54 (sext, J=7.1 Hz, 2H), 0.93-0.86 (m, 12H), 0.11 (s, 6H).

Reference Example 5-6

5-(3-{[(Tert-butyldimethylsilyl)oxy]methyl}-2-fluorophenyl)-3-fluoro-2-(3-isopropoxyazetidin-1-yl)pyridine (Reference Compound 5-6)

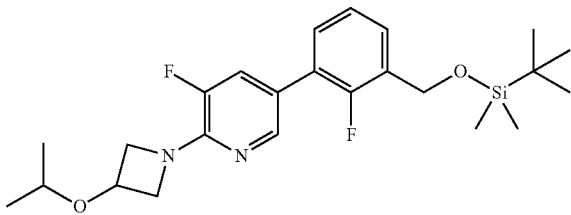 [SMILES: CC(C)OC1CN(c2ncc(-c3cccc(CO[Si](C)(C)C(C)(C)C)c3F)cc2F)C1]

The reaction was performed by the method described in Reference Example 5-2, except that 5-bromo-3-fluoro-2-[3-(methoxy-d₃)azetidin-1-yl]pyridine was replaced by 5-bromo-3-fluoro-2-(3-isopropoxyazetidin-1-yl)pyridine synthesized in the same manner as in Reference Example 8. Consequently, the title compound (yield 96%) was obtained as colorless oil Mass spectrum (ESI, m/z): 449[M+1]⁺.

¹H-NMR spectrum (400 MHz, DMSO-d₆) δ:8.13-8.09 (m, 1H), 7.70-7.61 (m, 1H), 7.49-7.39 (m, 2H), 7.32-7.24 (m, 1H), 4.80 (s, 2H), 4.57-4.47 (m, 1H), 4.38-4.30 (m, 2H), 3.94-3.84 (m, 2H), 3.65 (sep, J=6.1 Hz, 1H), 1.11 (d, J=6.1 Hz, 6H), 0.91 (s, 9H), 0.11 (s, 6H).

Reference Example 5-7

5-(3-{[(Tert-butyldimethylsilyl)oxy]methyl}-2-fluorophenyl)-3-fluoro-2-{3-[(tetrahydropyran-2-yl)oxy]azetidin-1-yl}pyridine (Reference Compound 5-7)

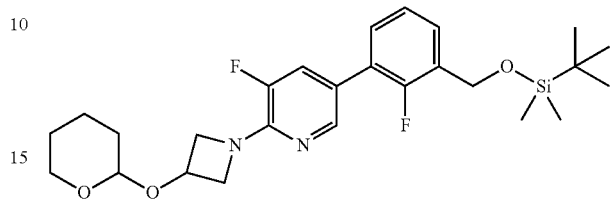

The reaction was performed by the method described in Reference Example 5-1, except that 5-bromo-3-fluoro-2-(3-methoxyazetidin-1-yl)pyridine was replaced by 5-bromo-3-fluoro-2-{3-[(tetrahydropyran-2-yl)oxy]azetidin-1-yl}pyridine synthesized in the same manner as in Reference Example 9. Consequently, the title compound (quantitative yield) was obtained as light yellow oil.

¹H-NMR spectrum (400 MHz, CDCl₃) δ:8.15-8.08 (m, 1H), 7.51-7.43 (m, 1H), 7.43-7.35 (m, 1H), 7.31-7.23 (m, 1H), 7.23-7.14 (m, 1H), 4.88-4.82 (m, 2H), 4.76-4.65 (m, 2H), 4.48-4.38 (m, 2H), 4.21-4.07 (m, 2H), 3.96-3.82 (m, 1H), 3.61-3.48 (m, 1H), 1.94-1.42 (m, 6H), 0.96 (s, 9H), 0.13 (s, 6H).

Reference Example 5-8

2-(Azetidin-1-yl)-5-(3-{[(tert-butyldimethylsilyl)oxy]methyl}-2-fluorophenyl)-3-fluoropyridine (Reference Compound 5-8)

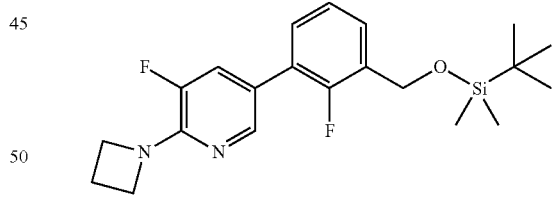

The reaction was performed by the method described in Reference Example 5-2, except that 5-bromo-3-fluoro-2-[3-(methoxy-d₃)azetidin-1-yl]pyridine was replaced by 2-(azetidin-1-yl)-5-bromo-3-fluoropyridine synthesized in the same manner as in Reference Example 10-1. Consequently, the title compound (yield 71%) was obtained as a white solid.

Mass spectrum (ESI, m/z): 391[M+1]⁺.

¹H-NMR spectrum (400 MHz, DMSO-d₆) δ:8.14-8.07 (m, 1H), 7.67-7.58 (m, 1H), 7.50-7.39 (m, 2H), 7.31-7.23 (m, 1H), 4.80 (s, 2H), 4.22-4.06 (m, 4H), 2.43-2.24 (m, 2H), 0.91 (s, 9H), 0.11 (s, 6H).

Reference Example 5-9

5-(3-{[(Tert-butyldimethylsilyl)oxy]methyl}-2-fluorophenyl)-3-fluoro-2-(3-fluoroazetidin-1-yl)pyridine (Reference Compound 5-9)

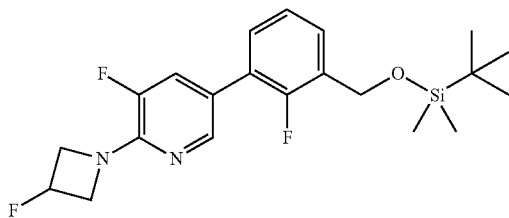 [SMILES: CC(C)(C)[Si](C)(C)OCc1cccc(-c2cnc(N3CC(F)C3)c(F)c2)c1F]

The reaction was performed by the method described in Reference Example 5-2, except that 5-bromo-3-fluoro-2-[3-(methoxy-d₃)azetidin-1-yl]pyridine was replaced by 5-bromo-3-fluoro-2-(3-fluoroazetidin-1-yl)pyridine synthesized in the same manner as in Reference Example 11-1. Consequently, the title compound (yield 63%) was obtained as light yellow oil. Mass spectrum (ESI, m/z): 409[M+1]$^+$.

$^1$H-NMR spectrum (400 MHz, DMSO-d$_6$) δ:8.17-8.11 (m, 1H), 7.72-7.66 (m, 1H), 7.50-7.40 (m, 2H), 7.33-7.25 (m, 1H), 5.71-5.38 (m, 1H), 4.81 (s, 2H), 4.56-4.37 (m, 2H), 4.27-4.11 (m, 2H), 0.91 (s, 9H), 0.11 (s, 6H).

Reference Example 5-10

5-(3-{[(Tert-butyldimethylsilyl)oxy]methyl}-2-fluorophenyl)-2-(3,3-difluoroazetidin-1-yl)-3-fluoropyridine (Reference Compound 5-10)

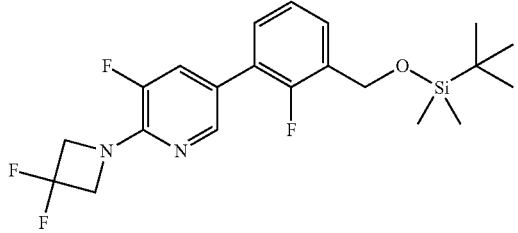 [SMILES: CC(C)(C)[Si](C)(C)OCc1cccc(-c2cnc(N3CC(F)(F)C3)c(F)c2)c1F]

The reaction was performed by the method described in Reference Example 5-2, except that 5-bromo-3-fluoro-2-[3-(methoxy-d₃)azetidin-1-yl]pyridine was replaced by 5-bromo-2-(3,3-difluoroazetidin-1-yl)-3-fluoropyridine synthesized in the same manner as in Reference Example 11-2. Consequently, the title compound (yield 75%) was obtained as light yellow oil.

Reference Example 5-11

5-(3-{[(Tert-butyldimethylsilyl)oxy]methyl}-2-fluorophenyl)-3-fluoro-2-(3-methylazetidin-1-yl)pyridine (Reference Compound 5-11)

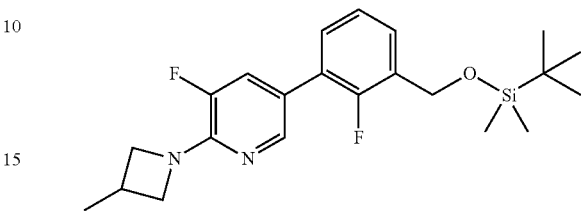

The reaction was performed by the method described in Reference Example 5-2, except that 5-bromo-3-fluoro-2-[3-(methoxy-d₃)azetidin-1-yl]pyridine was replaced by 5-bromo-3-fluoro-2-(3-methylazetidin-1-yl)pyridine synthesized in the same manner as in Reference Example 10-2. Consequently, the title compound (yield 86%) was obtained as light yellow oil. Mass spectrum (ESI, m/z): 405[M+1]$^+$.

$^1$H-NMR spectrum (400 MHz, DMSO-d$_6$) δ:8.12-8.08 (m, 1H), 7.65-7.58 (m, 1H), 7.48-7.39 (m, 2H), 7.31-7.24 (m, 1H), 4.80 (s, 2H), 4.28-4.20 (m, 2H), 3.74-3.67 (m, 2H), 2.88-2.77 (m, 1H), 1.25 (d, J=6.8 Hz, 3H), 0.91 (s, 9H), 0.11 (s, 6H).

Reference Example 5-12

5-(3-{[(Tert-butyldimethylsilyl)oxy]methyl}-2-fluorophenyl)-2-(3,3-dimethylazetidin-1-yl)-3-fluoropyridine (Reference Compound 5-12)

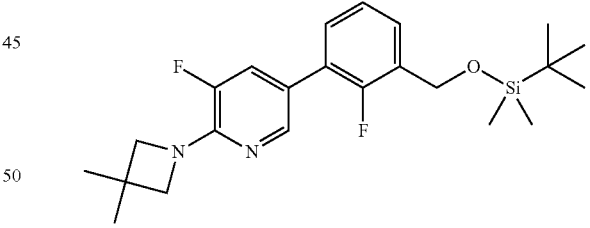

The reaction was performed by the method described in Reference Example 5-2, except that 5-bromo-3-fluoro-2-[3-(methoxy-d₃)azetidin-1-yl]pyridine was replaced by 5-bromo-2-(3,3-dimethylazetidin-1-yl)-3-fluoropyridine synthesized in the same manner as in Reference Example 10-3. Consequently, the title compound (yield 75%) was obtained as light yellow oil.

Mass spectrum (ESI, m/z): 419 [M+1]$^+$.

$^1$H-NMR spectrum (400 MHz, DMSO-d$_6$) δ:8.13-8.06 (m, 1H), 7.65-7.56 (m, 1H), 7.48-7.38 (m, 2H), 7.34-7.22 (m, 1H), 4.80 (s, 2H), 3.85-3.79 (m, 4H), 1.30 (s, 6H), 0.91 (s, 9H), 0.11 (s, 6H).

Reference Example 5-13

5-(3-{[(Tert-butyldimethylsilyl)oxy]methyl}-2-fluorophenyl)-3-fluoro-2-{3-methyl-3-[(tetrahydropyran-2-yl)oxy]azetidin-1-yl}pyridine (Reference Compound 5-13)

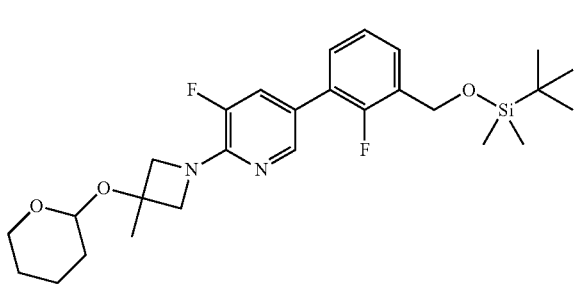 [SMILES: CC1(OC2CCCCO2)CN(c2ncc(-c3cccc(CO[Si](C)(C)C(C)(C)C)c3F)cc2F)C1]

The reaction was performed by the method described in Reference Example 5-2, except that 5-bromo-3-fluoro-2-[3-(methoxy-d₃)azetidin-1-yl]pyridine was replaced by 5-bromo-3-fluoro-2-{3-methyl-3-[(tetrahydropyran-2-yl)oxy]azetidin-1-yl}pyridine synthesized in the same manner as in Reference Example 14. Consequently, the title compound (yield 90%) was obtained as light yellow oil.

Mass spectrum (ESI, m/z): 505[M+1]⁺.

¹H-NMR spectrum (400 MHz, DMSO-d₆) δ:8.17-8.07 (m, 1H), 7.70-7.60 (m, 1H), 7.51-7.39 (m, 2H), 7.33-7.22 (m, 1H), 4.87-4.83 (m, 1H), 4.80 (s, 2H), 4.20-4.07 (m, 2H), 4.01-3.91 (m, 2H), 3.89-3.80 (m, 1H), 3.50-3.40 (m, 1H), 1.89-1.27 (m, 9H), 0.91 (s, 9H), 0.11 (s, 6H).

Reference Example 5-14

6-[5-(3-{[(Tert-butyldimethylsilyl)oxy]methyl}-2-fluorophenyl)-3-fluoropyridin-2-yl]-2-oxa-6-azaspiro[3.3]heptane (Reference Compound 5-14)

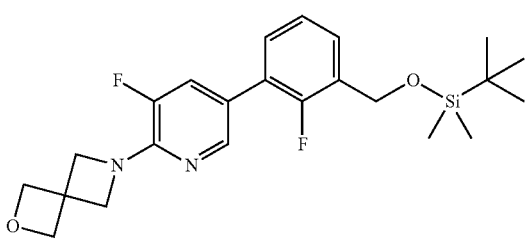 [SMILES: CC(C)(C)[Si](C)(C)OCc1cccc(-c2cnc(N3CC4(COC4)C3)c(F)c2)c1F]

The reaction was performed by the method described in Reference Example 5-2, except that 5-bromo-3-fluoro-2-[3-(methoxy-d₃)azetidin-1-yl]pyridine was replaced by 6-(5-bromo-3-fluoropyridin-2-yl)-2-oxa-6-azaspiro[3.3]heptane synthesized in the same manner as in Reference Example 10-4. Consequently, the title compound (yield 71%) was obtained as light yellow oil.

Mass spectrum (ESI, m/z): 433[M+1]⁺.

¹H-NMR spectrum (400 MHz, DMSO-d₆) δ:8.13-8.09 (m, 1H), 7.68-7.61 (m, 1H), 7.48-7.40 (m, 2H), 7.31-7.24 (m, 1H), 4.80 (s, 2H), 4.73 (s, 4H), 4.32-4.26 (m, 4H), 0.91 (s, 9H), 0.10 (s, 6H).

Reference Example 6-1

{2-Fluoro-3-[5-fluoro-6-(3-methoxyazetidin-1-yl)pyridin-3-yl]phenyl}methanol (Reference Compound 6-1)

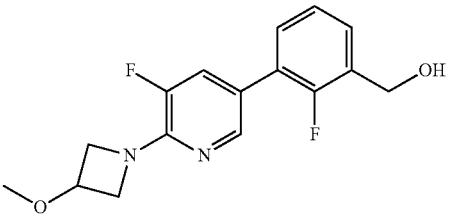 [SMILES: COC1CN(c2ncc(-c3cccc(CO)c3F)cc2F)C1]

1 M tetrabutylammonium fluoride/THF solution 1.2 mL (1.2 mmol) was added to a THF (8 mL) solution of 5-(3-{[(tert-butyldimethylsilyl)oxy]methyl}-2-fluorophenyl)-3-fluoro-2-(3-methoxyazetidin-1-yl)pyridine 399 mg (0.949 mmol) synthesized in the same manner as in Reference Example 5-1, and the mixture was stirred at room temperature for 2 hours. After the completion of the reaction, the reaction mixture was concentrated under reduced pressure. The concentrated residue was purified by silica gel column chromatography (eluting solvent; hexane:ethyl acetate) to give the title compound 280 mg (0.914 mmol, yield 96%) as a white solid.

¹H-NMR spectrum (400 MHz, DMSO-d₆) δ:8.14-8.08 (m, 1H), 7.70-7.62 (m, 1H), 7.50-7.37 (m, 2H), 7.30-7.22 (m, 1H), 5.32 (t, J=5.7 Hz, 1H), 4.60 (d, J=5.7 Hz, 2H), 4.39-4.24 (m, 3H), 3.98-3.89 (m, 2H), 3.26 (s, 3H).

Reference Example 6-2

(2-Fluoro-3-{5-fluoro-6-[3-(methoxy-d₃)azetidin-1-yl]pyridin-3-yl}phenyl)methanol (Reference Compound 6-2)

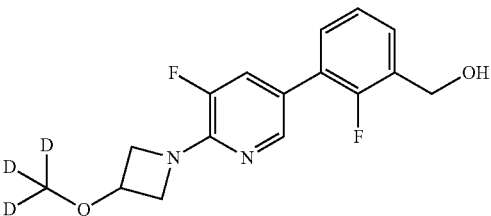 [SMILES: [2H]C([2H])([2H])OC1CN(c2ncc(-c3cccc(CO)c3F)cc2F)C1]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-3-fluoro-2-[3-(methoxy-d₃)azetidin-1-yl]pyridine synthesized in the same manner as in Reference Example 5-2. Consequently, the title compound (yield 91%) was obtained as a white solid.

Mass spectrum (ESI, m/z): 310[M+1]⁺.

¹H-NMR spectrum (400 MHz, DMSO-d₆) δ:8.15-8.08 (m, 1H), 7.71-7.60 (m, 1H), 7.49-7.38 (m, 2H), 7.30-7.21 (m, 1H), 5.32 (t, J=4.8 Hz, 1H), 4.60 (d, J=4.8 Hz, 2H), 4.40-4.24 (m, 3H), 3.99-3.87 (m, 2H).

Reference Example 6-3

{3-[6-(3-Ethoxyazetidin-1-yl)-5-fluoropyridin-3-yl]-2-fluorophenyl}methanol (Reference Compound 6-3)

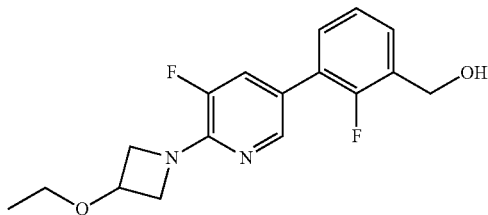 [SMILES: CCOC1CN(c2ncc(-c3cccc(CO)c3F)cc2F)C1]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-2-(3-ethoxyazetidin-1-yl)-3-fluoropyridine synthesized in the same manner as in Reference Example 5-3. Consequently, the title compound (yield 94%) was obtained as colorless oil.

Mass spectrum (ESI, m/z): 321[M+1]$^+$.

$^1$H-NMR spectrum (400 MHz, DMSO-d$_6$) δ:8.13-8.09 (m, 1H), 7.70-7.62 (m, 1H), 7.50-7.37 (m, 2H), 7.29-7.22 (m, 1H), 5.33 (br s, 1H), 4.60 (br s, 2H), 4.47-4.39 (m, 1H), 4.37-4.28 (m, 2H), 3.98-3.85 (m, 2H), 3.46 (q, J=7.0 Hz, 2H), 1.15 (t, J=7.0 Hz, 3H).

Reference Example 6-4

(2-Fluoro-3-{5-fluoro-6-[3-(2-fluoroethoxy)azetidin-1-yl]pyridin-3-yl}phenyl)methanol (Reference Compound 6-4)

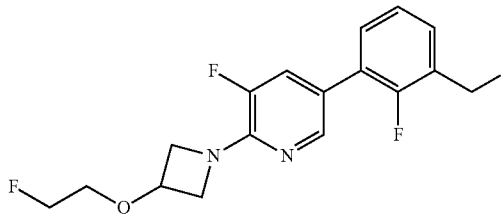

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluoro-2-[3-(2-fluoroethoxy)azetidin-1-yl]pyridine synthesized in the same manner as in Reference Example 5-4. Consequently, the title compound (yield 94%) was obtained as colorless oil.

Mass spectrum (ESI, m/z): 339[M+1]$^+$.

$^1$H-NMR spectrum (400 MHz, DMSO-d$_6$) δ:8.13-8.11 (m, 1H), 7.70-7.62 (m, 1H), 7.51-7.38 (m, 2H), 7.31-7.22 (m, 1H), 5.34 (t, J=5.3 Hz, 1H), 4.66-4.56 (m, 3H), 4.55-4.47 (m, 2H), 4.38-4.29 (m, 2H), 3.99-3.91 (m, 2H), 3.76-3.61 (m, 2H).

Reference Example 6-5

{2-Fluoro-3-[5-fluoro-6-(3-propoxyazetidin-1-yl)pyridin-3-yl]phenyl}methanol (Reference Compound 6-5)

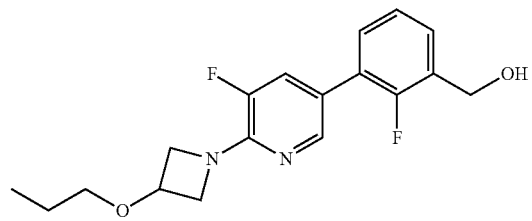 [SMILES: CCCOC1CN(c2ncc(-c3cccc(CO)c3F)cc2F)C1]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-3-fluoro-2-(3-propoxyazetidin-1-yl)pyridine synthesized in the same manner as in Reference Example 5-5. Consequently, the title compound (yield 94%) was obtained as colorless oil.

Mass spectrum (ESI, m/z): 335[M+1]$^+$.

$^1$H-NMR spectrum (400 MHz, DMSO-d$_6$) δ:8.14-8.09 (m, 1H), 7.70-7.61 (m, 1H), 7.51-7.37 (m, 2H), 7.31-7.21 (m, 1H), 5.38-5.29 (m, 1H), 4.59 (br s, 2H), 4.46-4.39 (m, 1H), 4.36-4.28 (m, 2H), 3.96-3.87 (m, 2H), 3.41-3.29 (m, 2H), 1.54 (sext, J=7.3 Hz, 2H), 0.89 (t, J=7.3 Hz, 3H).

Reference Example 6-6

{2-Fluoro-3-[5-fluoro-6-(3-isopropoxyazetidin-1-yl)pyridin-3-yl]phenyl}methanol (Reference Compound 6-6)

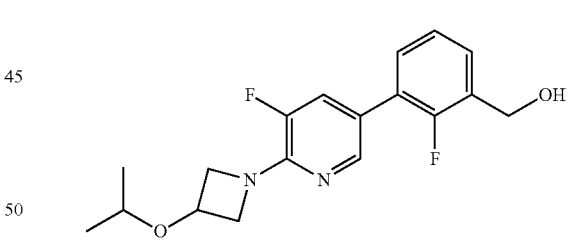

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-3-fluoro-2-(3-isopropoxyazetidin-1-yl)pyridine synthesized in the same manner as in Reference Example 5-6. Consequently, the title compound (yield 82%) was obtained as colorless oil.

Mass spectrum (ESI, m/z): 335[M+1]$^+$.

$^1$H-NMR spectrum (400 MHz, DMSO-d$_6$) δ:8.14-8.08 (m, 1H), 7.70-7.60 (m, 1H), 7.48-7.39 (m, 2H), 7.30-7.20 (m, 1H), 5.33 (br s, 1H), 4.63-4.57 (m, 2H), 4.56-4.48 (m, 1H), 4.37-4.30 (m, 2H), 3.95-3.85 (m, 2H), 3.65 (sep, J=6.1 Hz, 1H), 1.11 (d, J=6.1 Hz, 6H).

Reference Example 6-7

[2-Fluoro-3-(5-fluoro-6-{3-[(tetrahydropyran-2-yl)oxy]azetidin-1-yl}pyridin-3-yl)phenyl]methanol (Reference Compound 6-7)

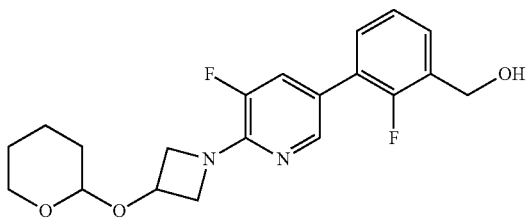 [SMILES: OCc1cccc(-c2cnc(N3CC(OC4CCCCO4)C3)c(F)c2)c1F]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-3-fluoro-2-{3-[(tetrahydropyran-2-yl)oxy]azetidin-1-yl}pyridine synthesized in the same manner as in Reference Example 5-7. Consequently, the title compound (yield 94%) was obtained as light yellow oil.

$^1$H-NMR spectrum (400 MHz, CDCl$_3$) δ:8.14-8.09 (m, 1H), 7.45-7.37 (m, 2H), 7.35-7.29 (m, 1H), 7.23-7.17 (m, 1H), 4.86-4.79 (m, 2H), 4.78-4.65 (m, 2H), 4.50-4.35 (m, 2H), 4.25-4.05 (m, 2H), 3.94-3.85 (m, 1H), 3.60-3.51 (m, 1H), 1.91-1.50 (m, 6H).

Reference Example 6-8

{3-[6-(Azetidin-1-yl)-5-fluoropyridin-3-yl]-2-fluorophenyl}methanol (Reference Compound 6-8)

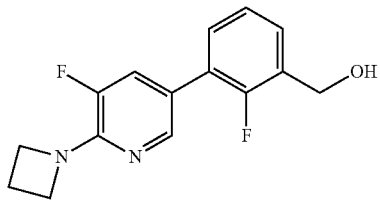 [SMILES: OCc1cccc(-c2cnc(N3CCC3)c(F)c2)c1F]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 2-(azetidin-1-yl)-5-(3-{[(tert-butyldimethylsilyl)oxy]methyl}-2-fluorophenyl)-3-fluoropyridine synthesized in the same manner as in Reference Example 5-8. Consequently, the title compound (yield 88%) was obtained as a white solid.

Mass spectrum (ESI, m/z): 277[M+1]$^+$.

$^1$H-NMR spectrum (400 MHz, DMSO-d$_6$) δ:8.14-8.07 (m, 1H), 7.66-7.58 (m, 1H), 7.49-7.38 (m, 2H), 7.30-7.21 (m, 1H), 5.30 (br s, 1H), 4.59 (br s, 2H), 4.25-3.99 (m, 4H), 2.45-2.28 (m, 2H).

Reference Example 6-9

{2-Fluoro-3-[5-fluoro-6-(3-fluoroazetidin-1-yl)pyridin-3-yl]phenyl}methanol (Reference Compound 6-9)

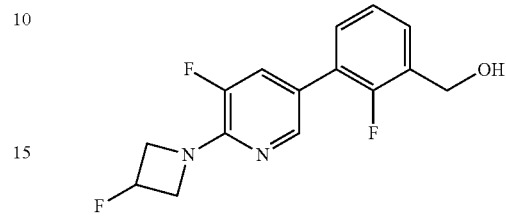

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-3-fluoro-2-(3-fluoroazetidin-1-yl)pyridine synthesized in the same manner as in Reference Example 5-9. Consequently, the title compound (yield 84%) was obtained as colorless oil.

Mass spectrum (ESI, m/z): 295[M+1]$^+$.

$^1$H-NMR spectrum (400 MHz, DMSO-d$_6$) δ:8.16-8.11 (m, 1H), 7.75-7.65 (m, 1H), 7.52-7.38 (m, 2H), 7.30-7.19 (m, 1H), 5.67-5.41 (m, 1H), 5.32 (br s, 1H), 4.63-4.57 (m, 2H), 4.53-4.39 (m, 2H), 4.25-4.10 (m, 2H).

Reference Example 6-10

{3-[6-(3,3-Difluoroazetidin-1-yl)-5-fluoropyridin-3-yl]-2-fluorophenyl}methanol (Reference Compound 6-10)

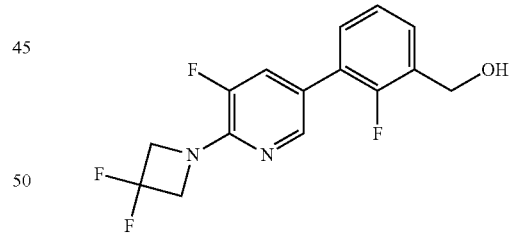

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-2-(3,3-difluoroazetidin-1-yl)-3-fluoropyridine synthesized in the same manner as in Reference Example 5-10. Consequently, the title compound (yield 83%) was obtained as a white solid.

Mass spectrum (ESI, m/z): 313[M+1]$^+$.

$^1$H-NMR spectrum (400 MHz, DMSO-d$_6$) δ:8.22-8.15 (m, 1H), 7.82-7.73 (m, 1H), 7.53-7.39 (m, 2H), 7.32-7.23 (m, 1H), 5.34 (br s, 1H), 4.64-4.50 (m, 6H).

Reference Example 6-11

(2-Fluoro-3-(5-fluoro-6-(3-methylazetidin-1-yl)pyridin-3-yl)phenyl)methanol (Reference Compound 6-11)

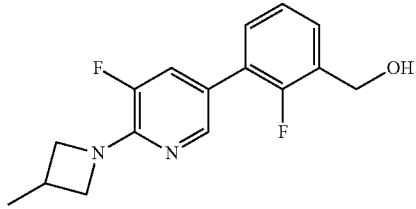 [SMILES: CC1CN(c2ncc(-c3cccc(CO)c3F)cc2F)C1]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-3-fluoro-2-(3-methylazetidin-1-yl)pyridine synthesized in the same manner as in Reference Example 5-11. Consequently, the title compound (yield 94%) was obtained as colorless oil.

Mass spectrum (ESI, m/z): 291[M+1]$^+$.

$^1$H-NMR spectrum (400 MHz, DMSO-d$_6$) δ:8.13-8.04 (m, 1H), 7.66-7.56 (m, 1H), 7.48-7.36 (m, 2H), 7.29-7.21 (m, 1H), 5.31 (br s, 1H), 4.59 (br s, 2H), 4.31-4.18 (m, 2H), 3.74-3.65 (m, 2H), 2.90-2.75 (m, 1H), 1.25 (d, J=6.9 Hz, 3H).

Reference Example 6-12

{3-[6-(3,3-Dimethylazetidin-1-yl)-5-fluoropyridin-3-yl]-2-fluorophenyl}methanol (Reference Compound 6-12)

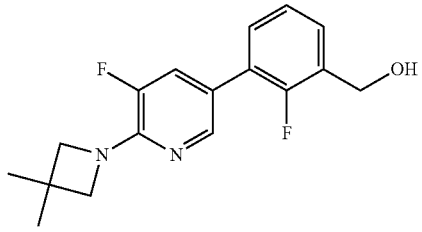 [SMILES: CC1(C)CN(c2ncc(-c3cccc(CO)c3F)cc2F)C1]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-2-(3,3-dimethylazetidin-1-yl)-3-fluoropyridine synthesized in the same manner as in Reference Example 5-12. Consequently, the title compound (quantitative yield) was obtained as colorless oil.

Mass spectrum (ESI, m/z): 305[M+1]$^+$.

$^1$H-NMR spectrum (400 MHz, DMSO-d$_6$) δ:8.12-8.06 (m, 1H), 7.67-7.57 (m, 1H), 7.50-7.36 (m, 2H), 7.29-7.21 (m, 1H), 5.31 (br s, 1H), 4.59 (br s, 2H), 3.85-3.77 (m, 4H), 1.30 (s, 6H).

Reference Example 6-13

[2-Fluoro-3-(5-fluoro-6-{3-methyl-3-[(tetrahydropyran-2-yl)oxy]azetidin-1-yl}pyridin-3-yl)phenyl]methanol (Reference Compound 6-13)

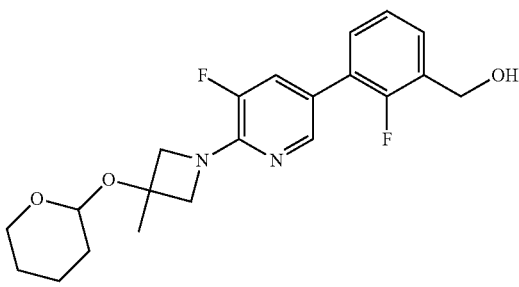 [SMILES: CC1(OC2CCCCO2)CN(c2ncc(-c3cccc(CO)c3F)cc2F)C1]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 5-(3-{[(tert-butyldimethylsilyl)oxy]methyl}-2-fluorophenyl)-3-fluoro-2-{3-methyl-3-[(tetrahydropyran-2-yl)oxy]azetidin-1-yl}pyridine synthesized in the same manner as in Reference Example 5-13. Consequently, the title compound (yield 85%) was obtained as colorless oil.

Reference Example 6-14

{2-Fluoro-3-[5-fluoro-6-(2-oxa-6-azaspiro[3.3]heptan-6-yl)pyridin-3-yl]phenyl}methanol (Reference Compound 6-14)

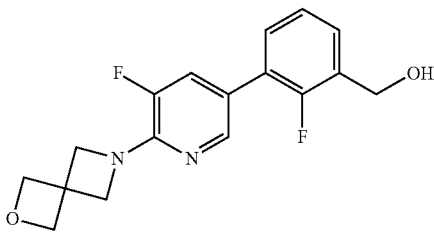 [SMILES: OCc1cccc(-c2cnc(N3CC4(COC4)C3)c(F)c2)c1F]

The reaction was performed by the method described in Reference Example 6-1, except that 5-(3-{[(tert-butyldimethylsilyl)oxy]methyl}-2-fluorophenyl)-3-fluoro-2-(3-methoxyazetidin-1-yl)pyridine was replaced by 6-[5-(3-{[(tert-butyldimethylsilyl)oxy]methyl}-2-fluorophenyl)-3-fluoropyridin-2-yl]-2-oxa-6-azaspiro[3.3]heptane synthesized in the same manner as in Reference Example 5-14. Consequently, the title compound (yield 94%) was obtained as colorless oil.

Mass spectrum (ESI, m/z): 319[M+1]$^+$.

$^1$H-NMR spectrum (400 MHz, DMSO-d$_6$) δ:8.14-8.09 (m, 1H), 7.68-7.61 (m, 1H), 7.49-7.36 (m, 2H), 7.30-7.22 (m, 1H), 5.41-5.23 (m, 1H), 4.73 (s, 4H), 4.63-4.51 (m, 2H), 4.33-4.23 (m, 4H).

Reference Example 7

2-Fluoroethyl methanesulfonate (Reference Compound 7)

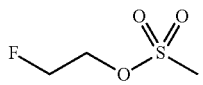

At 0° C., triethylamine 1.81 mL (13.0 mmol) was added to a methylene chloride (5 mL) solution of 2-fluoromethanol 0.500 mL (8.66 mmol). Next, a solution of methanesulfonyl chloride 0.740 mL (9.56 mmol) in methylene chloride 5 mL was added thereto dropwise at 0° C. The mixture was stirred for 1 hour and was stirred at room temperature for 2 hours. After the completion of the reaction, water was added to the reaction mixture and followed by extraction with methylene chloride. The organic layer was washed with water, dried over anhydrous magnesium sulfate, and filtered. The filtrate was concentrated under reduced pressure. The concentrated residue was dried under reduced pressure to give a crude product 1.25 g including the title compound as yellow oil.

Reference Example 8

5-Bromo-3-fluoro-2-(3-methoxyazetidin-1-yl)pyridine (Reference Compound 8)

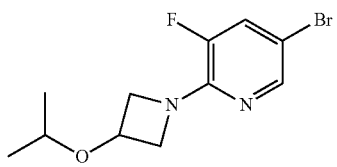 [SMILES: CC(C)OC1CN(c2ncc(Br)cc2F)C1]

Silver oxide 2.81 g (12.1 mmol) and 2-iodopropane 2.02 mL (20.2 mmol) were added to an acetonitrile (10 mL) solution of 1-(5-bromo-3-fluoropyridin-2-yl)azetidin-3-ol 1.00 g (4.05 mmol) synthesized in the same manner as in Reference Example 1, and the mixture was stirred at room temperature for 4 days. After the completion of the reaction, the reaction mixture was filtered. The filtrate was concentrated under reduced pressure. The concentrated residue was purified by silica gel column chromatography (eluting solvent; hexane:ethyl acetate) to give the title compound 583 mg (2.02 mmol, yield 50%) as colorless oil.

Mass spectrum (ESI, m/z): 289,291[M+1]$^+$.

$^1$H-NMR spectrum (400 MHz, DMSO-d$_6$) δ:8.04-8.00 (m, 1H), 7.82-7.76 (m, 1H), 4.52-4.46 (m, 1H), 4.31-4.24 (m, 2H), 3.85-3.80 (m, 2H), 3.63 (sep, J=6.1 Hz, 1H), 1.10 (d, J=6.1 Hz, 6H).

Reference Example 9

5-Bromo-3-fluoro-2-{3-[(tetrahydropyran-2-yl)oxy]azetidin-1-yl}pyridine (Reference Compound 9)

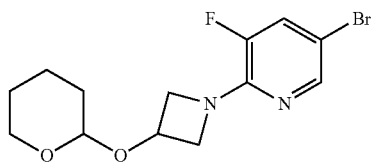 [SMILES: Fc1cc(Br)cnc1N1CC(OC2CCCCO2)C1]

3,4-dihydro-2H-pyran 0.18 mL (1.99 mmol) and pyridinium p-toluenesulfonate 61 mg (0.243 mmol) were added to a methylene chloride (8 mL) solution of 1-(5-bromo-3-fluoropyridin-2-yl)azetidin-3-ol 300 mg (1.21 mmol) synthesized in the same manner as in Reference Example 1, and the mixture was stirred at room temperature for 16 hours. After the completion of the reaction, a saturated aqueous sodium bicarbonate solution was added to the reaction mixture, and followed by extraction with methylene chloride. The organic layer was washed with brine, dried over anhydrous magnesium sulfate, and filtered. The filtrate was concentrated under reduced pressure. The concentrated residue was purified by silica gel column chromatography (eluting solvent; hexane:ethyl acetate) to give the title compound 310 mg (0.936 mmol, yield 77%) as colorless oil.

$^1$H-NMR spectrum (400 MHz, CDCl$_3$) δ: 7.99-7.95 (m, 1H), 7.32-7.27 (m, 1H), 4.73-4.63 (m, 2H), 4.41-4.30 (m, 2H), 4.16-4.00 (m, 2H), 3.92-3.83 (m, 1H), 3.59-3.48 (m, 1H), 1.96-1.42 (m, 6H).

Reference Example 10-1

2-(Azetidin-1-yl)-5-bromo-3-fluoropyridine (Reference Compound 10-1)

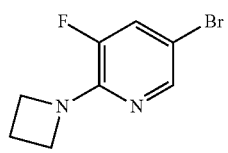

Azetidine hydrochloride 289 mg (3.09 mmol) and triethylamine 0.90 mL (6.46 mmol) were added to an ethanol (6 mL) solution of 5-bromo-2,3-difluoropyridine 300 mg (1.55 mmol), and the mixture was stirred at 50° C. for 2 hours. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent; hexane:ethyl acetate) to give the title compound 342 mg (1.48 mmol, yield 96%) as a white solid.

Mass spectrum (ESI, m/z): 231,233[M+1]$^+$.

$^1$H-NMR spectrum (400 MHz, DMSO-d$_6$) δ:8.02-7.98 (m, 1H), 7.79-7.72 (m, 1H), 4.18-3.96 (m, 4H), 2.44-2.23 (m, 2H).

Reference Example 10-2

5-Bromo-3-fluoro-2-(3-methylazetidin-1-yl)pyridine (Reference Compound 10-2)

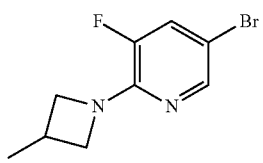

The reaction was performed by the method described in Reference Example 10-1, except that the azetidine hydrochloride was replaced by 3-methylazetidine hydrochloride. Consequently, the title compound (quantitative yield) was obtained as colorless oil.

Mass spectrum (ESI, m/z): 245,247[M+1]$^+$.

$^1$H-NMR spectrum (400 MHz, DMSO-d$_6$) δ:8.03-7.97 (m, 1H), 7.80-7.71 (m, 1H), 4.23-4.11 (m, 2H), 3.67-3.60 (m, 2H), 2.86-2.74 (m, 1H), 1.22 (d, J=6.9 Hz, 3H).

Reference Example 10-3

5-Bromo-2-(3,3-dimethylazetidin-1-yl)-3-fluoropyridine (Reference Compound 10-3)

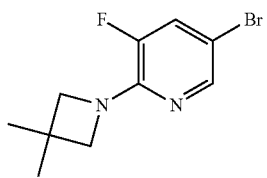

The reaction was performed by the method described in Reference Example 10-1, except that the azetidine hydrochloride was replaced by 3,3-dimethylazetidine hydrochloride. Consequently, the title compound (quantitative yield) was obtained as colorless oil.

Mass spectrum (ESI, m/z): 259,261[M+1]$^+$.

Reference Example 10-4

6-(5-Bromo-3-fluoropyridin-2-yl)-2-oxa-6-azaspiro[3.3]heptane (Reference Compound 10-4)

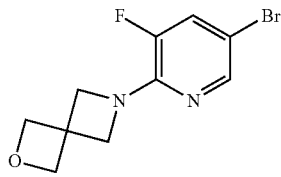 [SMILES: Fc1cc(Br)cnc1N1CC2(COC2)C1]

The reaction was performed by the method described in Reference Example 10-1, except that the azetidine hydrochloride was replaced by 2-oxa-6-azaspiro[3,3]heptane oxalate. Consequently, the title compound (yield 47%) was obtained as a white solid.

Mass spectrum (ESI, m/z): 273,275[M+1]$^+$.

$^1$H-NMR spectrum (400 MHz, DMSO-d$_6$) δ:8.04-8.00 (m, 1H), 7.83-7.76 (m, 1H), 4.71 (s, 4H), 4.26-4.20 (m, 4H).

Reference Example 11-1

5-Bromo-3-fluoro-2-(3-fluoroazetidin-1-yl)pyridine (Reference Compound 11-1)

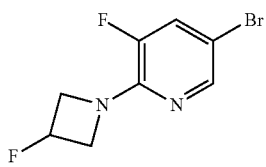 [SMILES: Fc1cc(Br)cnc1N1CC(F)C1]

3-Fluoroazetidine hydrochloride 230 mg (2.06 mmol) and cesium carbonate weighing 1.0 g (3.07 mmol) were added to an N-methylpyrrolidone (6 mL) solution of 5-bromo-2,3-difluoropyridine 200 mg (1.03 mmol), and the mixture was stirred at 80° C. for 2 hours. After the completion of the reaction, water was added to the reaction mixture, and followed by extraction with ethyl acetate. The organic layer was washed with brine, dried over anhydrous magnesium sulfate, and filtered. The filtrate was concentrated under reduced pressure. The concentrated residue was purified by silica gel column chromatography (eluting solvent; hexane:ethyl acetate) to give the title compound 252 mg (1.01 mmol, yield 98%) as colorless oil.

Mass spectrum (ESI, m/z): 249,251[M+1]$^+$.

$^1$H-NMR spectrum (400 MHz, DMSO-d$_6$) δ:8.08-8.04 (m, 1H), 7.88-7.81 (m, 1H), 5.67-5.33 (m, 1H), 4.51-4.28 (m, 2H), 4.22-3.95 (m, 2H).

Reference Example 11-2

5-Bromo-2-(3,3-difluoroazetidin-1-yl)-3-fluoropyridine (Reference Compound 11-2)

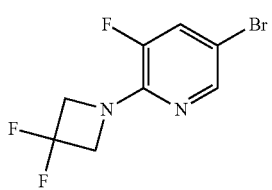 [SMILES: Fc1cc(Br)cnc1N1CC(F)(F)C1]

The reaction was performed by the method described in Reference Example 11-1, except that the 3-fluoroazetidine hydrochloride was replaced by 3,3-difluoroazetidine hydrochloride. Consequently, the title compound (yield 78%) was obtained as colorless oil.

Mass spectrum (ESI, m/z): 267,269[M+1]$^+$.

$^1$H-NMR spectrum (400 MHz, DMSO-d$_6$) δ:8.15-8.08 (m, 1H), 7.99-7.90 (m, 1H), 4.62-4.37 (m, 4H).

Reference Example 12

1-(5-Bromo-3-fluoropyridin-2-yl)azetidin-3-one (Reference Compound 12)

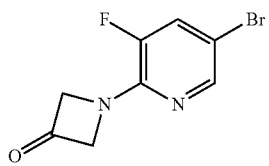 [SMILES: O=C1CN(c2ncc(Br)cc2F)C1]

Azadol 40 mg (0.261 mmol) and iodobenzene diacetate 1.80 g (5.59 mmol) were added to a methylene chloride (10 mL) solution of 1-(5-bromo-3-fluoropyridin-2-yl)azetidin-3-ol 1.00 g (4.05 mmol) synthesized in the same manner as in Reference Example 1, and the mixture was stirred at room temperature for 22 hours. After the completion of the reaction, a saturated aqueous sodium bicarbonate solution and sodium thiosulfate were added to the reaction mixture, and the mixture was stirred for 1 hour and extracted with ethyl acetate. The organic layer was washed with a saturated aqueous sodium bicarbonate solution, dried over anhydrous magnesium sulfate, and filtered. The filtrate was concentrated under reduced pressure. TBME and hexane were added to the concentrated residue, and the mixture was stirred at room temperature. The solid was collected by filtration to give the title compound 504 mg (2.06 mmol, yield 51%) as a white solid.

$^1$H-NMR spectrum (400 MHz, DMSO-$d_6$) δ:8.16-8.12 (m, 1H), 7.99-7.90 (m, 1H), 4.95-4.91 (m, 4H).

Reference Example 13

1-(5-Bromo-3-fluoropyridin-2-yl)-3-methylazetidin-3-ol (Reference Compound 13)

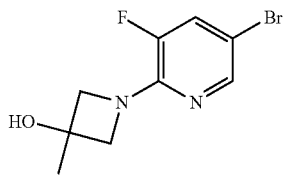

At 0° C., 1 M methyl magnesium bromide THF solution 4.90 mL (4.90 mmol) was added dropwise to a THF (10 mL) solution of 1-(5-bromo-3-fluoropyridin-2-yl)azetidin-3-one 1.0 g (4.08 mmol) synthesized in the same manner as in Reference Example 12, and the mixture was stirred at room temperature for 1 hour. After the completion of the reaction, saturated aqueous ammonium chloride solution was added to the reaction mixture, and followed by extraction with ethyl acetate. The organic layer was washed with water, dried over anhydrous magnesium sulfate, and filtered.

The filtrate was concentrated under reduced pressure. The concentrated residue was purified by silica gel column chromatography (eluting solvent; hexane:ethyl acetate) to give the title compound 990 mg (3.79 mmol, yield 93%) as colorless oil. Mass spectrum (ESI, m/z): 261,263[M+1]$^+$.

$^1$H-NMR spectrum (400 MHz, DMSO-$d_6$) δ:8.04-8.00 (m, 1H), 7.81-7.76 (m, 1H), 5.61 (br s, 1H), 3.94-3.87 (m, 4H), 1.44 (s, 3H).

Reference Example 14

5-Bromo-3-fluoro-2-{3-methyl-3-[(tetrahydropyran-2-yl)oxy]azetidin-1-yl}pyridine (Reference Compound 14)

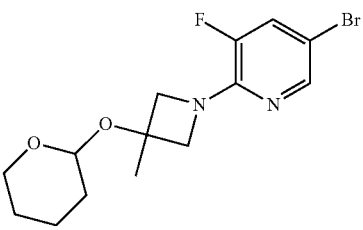 [SMILES: CC1(OC2CCCCO2)CN(c2ncc(Br)cc2F)C1]

3,4-dihydro-2H-pyran 0.2 mL (2.21 mmol) and pyridinium p-toluenesulfonate 33 mg (0.131 mmol) were added to a THF (6 mL) solution of 1-(5-bromo-3-fluoropyridin-2-yl)-3-methylazetidin-3-ol 340 mg (1.30 mmol) synthesized in the same manner as in Reference Example 13, and the mixture was stirred at 50° C. for 7 hours. After the completion of the reaction, water was added to the reaction mixture, and followed by extraction with ethyl acetate. The organic layer was washed with water, dried over anhydrous magnesium sulfate, and filtered. The filtrate was concentrated under reduced pressure. The concentrated residue was purified by silica gel column chromatography (eluting solvent; hexane:ethyl acetate) to give the title compound 396 mg (1.15 mmol, yield 88%) as colorless oil.

Mass spectrum (ESI, m/z): 345,347[M+1]$^+$.

$^1$H-NMR spectrum (400 MHz, DMSO-$d_6$) δ:8.05-8.00 (m, 1H), 7.84-7.76 (m, 1H), 4.95-4.76 (m, 1H), 4.14-4.00 (m, 2H), 3.96-3.78 (m, 3H), 3.48-3.40 (m, 1H), 1.89-1.26 (m, 9H).

Test Example 1

Human VAP-1 Enzyme Inhibition Test

This test was conducted by modifying the method of P. H. Yu et al. (Diabetologia 40 1243 (1997)). Human VAP-1 enzyme (R&D Systems, Inc.) was pre-incubated in a 96-well plate with the compound dissolved in dimethylsulfoxide at room temperature for 20 minutes. Next, in a solution to the final volume of 200 μL, the enzyme reaction solution was incubated with $^{14}$C-benzylamine (final concentration 100 μM) at 37° C. for 1 hour. The reaction was terminated by the addition of 100 μL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[VAP-1 enzyme activity after treatment with the compound]/[VAP-1 enzyme activity in the presence of dimethylsulfoxide alone without the compound]}×100  [Math. 1]

In this test, the compounds of the present invention showed excellent human VAP-1 inhibitory activity. For example, inhibition ratio of 50% or over was attained by the compounds, each 30 nM, of Examples 1, 2, 3, 4, 6, 8, 9, 10, 11, 12, 13, 15 and 16.

Test Example 2

Human Plasma VAP-1 Inhibition Test

This test was conducted by modifying the method of P. H. Yu et al. (Diabetologia 40 1243 (1997)). Human blood was collected from a healthy donor in a heparin tube, and was centrifuged at 3000 rpm and 4° C. for 10 minutes to get plasma. The plasma was pre-incubated in a 96-well microplate with the compound dissolved in dimethylsulfoxide and Pargyline (final concentration 100 µM) at room temperature for 20 minutes. Next, in a solution to the final volume of 200 µL, the plasma reaction solution was incubated with $^{14}$C-benzylamine (final concentration 50 µM) at 37° C. for 1 hour. The reaction was terminated by the addition of 100 µL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[VAP-1 activity after treatment with the compound]/[VAP-1 activity in the presence of dimethylsulfoxide alone without the compound]}×100     [Math. 2]

Test Example 3

Rat Plasma VAP-1 Inhibition Test

This test was conducted by modifying the method of P. H. Yu et al. (Diabetologia 40 1243 (1997)). Blood was collected from 7-12 week old SD male rats in heparin tubes, and was centrifuged at 3000 rpm and 4° C. for 10 minutes to get plasma. The plasma was pre-incubated in a 96-well microplate with the compound dissolved in dimethylsulfoxide and Pargyline (final concentration 100 µM) at room temperature for 20 minutes. Next, in a solution to the final volume of 200 µL, the plasma reaction solution was incubated with $^{14}$C-benzylamine (final concentration 2.5 µM) at 37° C. for 3 hours. The reaction was terminated by the addition of 100 µL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[VAP-1 activity after treatment with the compound]/[VAP-1 activity in the presence of dimethylsulfoxide alone without the compound]}×100     [Math. 3]

Test Example 4

(Ex Vivo) Rat Plasma VAP-1 Inhibition Test after Oral Administration of the Compound The compound was orally administered (0.3-10 mg/kg) to 7-12 week old SD male rats in the non-fasting state. Under anesthesia, the blood was collected in heparin tubes from the jugular vein before the administration and 3, 8 and 24 hours after the administration. The blood was centrifuged at 14000 rpm for 10 minutes to get plasma. The VAP-1 enzyme activity in the plasma was measured by radiochemical enzyme assay.

The radiochemical enzyme assay was conducted by modifying the method of P. H. Yu et al. (Diabetologia 40 1243 (1997)). $^{14}$C-benzylamine (2.5 µM) was added to the obtained plasma, and was incubated at 37° C. for 3 hours. The reaction was terminated by the addition of 100 µL of 2 M citric acid solution to the reaction solution. The oxidative product was extracted using a toluene/ethyl acetate mixture and the radioactivity was measured with a liquid scintillation counter. The inhibition ratio of the compound was calculated using the following equation.

Inhibition ratio={1−[Plasma VAP-1 activity after administration of the compound]/[Plasma VAP-1 activity before administration]}×100     [Math. 4]

In this test, the compounds of the present invention showed excellent VAP-1 inhibitory activity. For example, inhibition ratio of 50% or over was attained 3 hours after the administration of the compounds, each at a dose of 0.3 mg/kg, of Examples 1, 2, 3, 4, 6, 8, 9, 10, 11, 12, 13, 15 and 16.

Test Example 5

Effect on Albuminuria of Diabetic Rats

Diabetes is induced by intravenous injection of 50 mg/mL/kg streptozotocin (STZ) in 2 mM citric acid buffer solution (pH 4.5) into 7 to 8 week old (weighing 180 to 250 g) SD rats. At the same time, normal rats are injected with the same amount of 2 mM citric acid buffer solution (pH 4.5) as control. The blood glucose level is measured by an enzyme electrode method. On the fourth day after the STZ injection, rats with a blood glucose level above 350 mg/dL are classified as a diabetic model. The compound is administered daily for 4 weeks from the day of the STZ injection. After the treatment with the compound for 4 weeks, urine is collected for 24 hours using a metabolic cage, and the albumin concentration in the urine is measured.

Test Example 6

Effect on Livers in Non-Alcoholic Steatohepatitis (NASH) Models

This study is conducted using NASH model mice/STAM (registered trademark) model mice (Medical Molecular Morphology, 46, 141 (2013)) from Stelic Institute & Co., Inc.

Fourteen-day-pregnant $C_{57}$BL6J/JcL mice (CLEA Japan, Inc.) are fed and allowed to give the birth. Two-day-old mice are subcutaneously injected with streptozotocin (SIGMA-ALDRICH JAPAN) in physiological saline (Japanese Pharmacopoeia, Otsuka Pharmaceutical Co., Ltd.) one time to their backs. After 4 weeks of age, the mice are fed with high fat diet (High Fat Diet 32 (sterilized by radiation, CLEA Japan, Inc.) until the end of the experimental.

The compound is orally administered daily from 5- or 6-week-old. At 9- or 11-week-old, the animals are sacrificed under anesthesia. The livers are collected and their wet weights are measured. Paraffin sections or frozen sections are prepared from part of the livers, and are histopathologically examined, and the NAFLD activity score is measured. Further, RNA is extracted from the part of the livers, and the expression of fibrosis marker gene is measured by a quantitative PCR method. The results are statistically analyzed using EXSUS or Prism 4 (manufactured by GraphPad Software).

Test Example 7

Cytotoxicity Inhibition Test in Human Normal Glomerular Microvascular Endothelial Cells Human normal glomerular microvascular endothelial cells are plated at 6000 cells/well in a collagen-coated 96-well culture plate. After one day of culture, the medium at each well is completely removed by aspiration and replaced with 50 µL of the compound solution diluted with the basal medium. The basal medium containing 0.1% DMSO is added to control wells. Subsequently, the plate is incubated in $CO_2$ incubator for 30 minutes. Fifty microliters of 2 mM methylamine diluted with the basal medium is added (final concentration 1 mM) to each negative control well (0% inhibition) as well as the compound-containing well, and 50 µL of the basal medium is added to each positive control well (100% inhibition). The plate is incubated in $CO_2$ incubator for 2 days. Ten microliters of CCK-8 is added to each well and the mixtures are incubated in a plate incubator at 37° C. for approximately 2 hours after stirring with a plate shaker. The absorbance of the mixtures at 450 nm is measured with a multiplate reader. The cytotoxicity inhibition ratio of the compound is calculated from the following equation.

Inhibition ratio={[Average absorbance of the compound-containing wells]−[Average absorbance of negative control wells]}/{[Average absorbance of positive control wells]−[Average absorbance of negative control wells]}×100    [Math. 5]

Test Example 8

Cytotoxicity Inhibition Test in Human Normal Hepatic Sinusoid-Like Microvascular Endothelial Cells Human normal hepatic sinusoid-like microvascular endothelial cells are plated at 6000 cells/well in a collagen-coated 96-well culture plate. After one day of culture, the medium at each well is completely removed by aspiration and replaced with 50 µL of the compound solution diluted with the basal medium. The basal medium containing 0.1% DMSO is added to control wells. Subsequently, the plate is incubated in $CO_2$ incubator for 30 minutes. Fifty microliters of 2 mM methylamine diluted with the basal medium is added (final concentration 1 mM) to each negative control well (0% inhibition) as well as the compound-containing well, and 50 µL of the basal medium is added to each positive control well (100% inhibition). The plate is incubated in $CO_2$ incubator for 2 days. Ten microliters of CCK-8 is added to each well and the mixtures are incubated in a plate incubator at 37° C. for approximately 2 hours after stirring with a plate shaker. The absorbance of the mixtures at 450 nm is measured with a multiplate reader. The cytotoxicity inhibition ratio of the compound is calculated from the following equation.

Inhibition ratio={[Average absorbance of the compound-containing wells]−[Average absorbance of negative control wells]}/{[Average absorbance of positive control wells]−[Average absorbance of negative control wells]}×100    [Math. 6]

Test Example 9

Rat Pharmacokinetic (PK) Study (Concentration of Compound in Plasma after Oral Administration)

Seven to eight week old SD rats (weighing 180 to 250 g) were orally administered with a suspension of the compound in 0.5 W/V % methylcellulose 400 solution. Under anesthesia, the blood was collected from the jugular vein in EDTA tubes at 0.25, 0.5, 1, 2, 4, 6, 8 and 24 hours after the administration of the compound. The blood was centrifuged at 4° C. and 6000 g for 3 minutes to give plasma. Acetonitrile was added to the plasma, and the mixture was stirred with a shaker at 750 rpm for 3 minutes and was deproteinized by centrifugation at 3700 rpm for 2 minutes. The obtained sample was analyzed by LC/MS under the following conditions.

The concentration of the compound in the plasma at each blood sampling time was determined by an internal standard method, and AUC all (Area Under Curve) was calculated by a trapezoidal method.

The following LC and MS systems were used for measurement.

LC: CBM 30 series manufactured by Shimadzu Corporation
  Column: Phenomenex Kinetex $C_{18}$ (50×2.1 mm, 2.6 µm)
  Column temperature: 40° C.
  Flow rate: 0.3 mL/min
  Mobile phase A: 0.1% aqueous formic acid solution, mobile phase B: 0.1% formic acid, 50% acetonitrile/methanol mixture
  Gradients: 0-2 min: A/B=90/10-10/90, 2-3 min: A/B=10/90, 3-3.01 min: A/B=10/90-90/10
MS: 3200 manufactured by SCIEX
  Ionization: ESI
  Mode: positive In this study, the compounds of the present invention showed excellent PK. For example, 1000 ngh/mL or higher AUC was attained by the compounds of Examples 8, 15 and 16 at a dose of 3 mg/kg, and the amount of metabolites found in the blood was small.

Test Example 10

Cytochrome P450 (CYP) Metabolism Test

The reaction solution for metabolic stability measurement was prepared by mixing 2 mg protein/mL human recombinant CYP enzyme 3A4, 2D6, 2C9, 2C19, 1A2 or 2C8, 1 mg/mL glucose 6-phosphate (G-6-P) as a cofactor, 0.4 unit/mL glucose-6-phosphate dehydrogenase (G-6-P-DH), 0.665 mg/mL magnesium chloride ($MgCl_2$) and 1 mg/mL nicotinamide adenine dinucleotide (NADP+Na) into 1 mL of 100 mmol/L potassium phosphate buffer (pH 7.4) so that the final concentrations would be the concentrations described above. The human recombinant CYP enzyme used herein was obtained from Cypex Ltd. (UK) via Nosan Co., Ltd.

The reaction solution was pre-incubated at 37° C. for 5 minutes, and the reaction was initiated by adding the compound in a final concentration of 5 µmon. 100 Microliter portions were collected from the reaction system at 0, 5, 10, 15, 20 and 30 minutes after the start of metabolic reaction, and the reaction was terminated by adding the portion to 300 µL methanol. After the completion of the reaction, the sample was subjected to post treatments such as deproteinization and analyzed by UV-HPLC as described below.

Analysis Method

The peak area of the compound was calculated using Lab Solution Software (Shimadzu Corporation), and the residual ratio (%) of the compound at each incubation time was determined using the following equation.

Residual ratio (%)=[Peak area at incubation time]/[Peak area at 0 minutes]×100    [Math. 7]

Next, the residual amount (nmol/mL) of the compound at each incubation time was determined using the following equation.

Residual amount (nmol/mL)=[Initial concentration in reaction solution (5 nmol/mL)]×residual ratio/100    [Math. 8]

Lastly, a graph was drawn on Excel which plotted the reaction time on the abscissa and the residual amount on the ordinate, and the slope in the time range in which linearity was observed was determined as the elimination rate (nmol/min/200 pmol-CYP).

The LC system used is as follows.

LC: LC20 HPLC system manufactured by Shimadzu Corporation

Column: Phenomenex Kinetex C18 (100×2.1 mm, 2.6 µm)

Column temperature: 40° C.

Flow rate: 0.25 mL/min

Mobile phase A: 0.1% aqueous formic acid solution, mobile phase B: 0.1% formic acid, 50% acetonitrile/methanol mixture Gradients: 0-3 min: A/B=90/10, 3-11 min: 90/10-5/95, 11-15 min: A/B=5/95, 15-15.1 min: A/B=5/95-90/10

Measurement UV wavelengths: 200 to 350 nm

In this study, the compounds of the invention showed excellent metabolic stability. For example, the compounds of Examples 8, 15 and 16 attained an elimination rate of not more than 0.030 nmol/min/200 pmol-CYP with all kinds of CYP.

INDUSTRIAL APPLICABILITY

The compounds of the present invention of the general formula (I) or pharmacologically acceptable salts thereof have high VAP-1 inhibitory activity and excellent pharmacokinetic characteristics, and are therefore useful for the treatment of diseases that are prevented, alleviated and/or remedied by inhibiting VAP-1, typically, nonalcoholic fatty liver diseases such as nonalcoholic steatohepatitis; inflammatory diseases such as atopic dermatitis and psoriasis; diabetic complications such as diabetic neuropathy, diabetic retinopathy (in particular, diabetic macular edema) and diabetic nephropathy; vascular diseases such as atherosclerosis: heart diseases such as myocardial infarction; and metabolic disorders such as obesity.

The invention claimed is:
1. A compound of

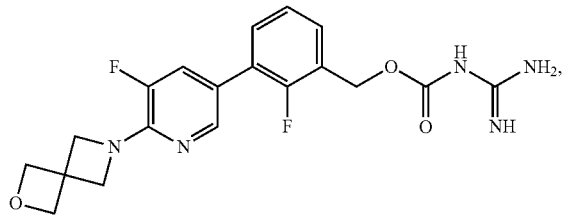 [SMILES: N=C(N)NC(=O)OCc1cccc(-c2cnc(N3CC4(COC4)C3)c(F)c2)c1F]

or a pharmacologically acceptable salt thereof.

2. The compound according to claim 1 or a pharmacologically acceptable salt thereof, wherein the pharmacologically acceptable salt is a salt of an organic acid.

3. The compound according to claim 1 or a pharmacologically acceptable salt thereof, wherein the pharmacologically acceptable salt is a salt of a dicarboxylic acid.

4. A pharmaceutical composition comprising the compound of claim 1, or a pharmacologically acceptable salt thereof, and at least one type of pharmacologically acceptable additive.

5. A method for treating or alleviating diabetic nephropathy by inhibiting VAP-1, comprising administering a therapeutically effective amount of the compound of claim 1 or a pharmacologically acceptable salt thereof, to a patient in need thereof.

6. A method for treating or alleviating non-alcoholic steatohepatitis by inhibiting VAP-1, comprising administering a therapeutically effective amount of the compound according to claim 1 or a pharmacologically acceptable salt thereof, to a patient in need thereof.

* * * * *